(12) United States Patent  
Schaller et al.

(10) Patent No.: US 8,591,583 B2  
(45) Date of Patent: Nov. 26, 2013

(54) DEVICES FOR TREATING THE SPINE

(75) Inventors: Laurent Schaller, Los Altos, CA (US); Timothy McGrath, Fremont, CA (US); Ryan Connolly, Menlo Park, CA (US); David Needleman, San Carlos, CA (US); Steven Golden, Menlo Park, CA (US); John Ashley, San Francisco, CA (US); James Lee, San Mateo, CA (US); Jeffrey Emery, Emerald Hills, CA (US); J. Brook Burley, Mountain View, CA (US); Larry T. Khoo, Studio City, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 1426 days.

(21) Appl. No.: 12/034,853

(22) Filed: Feb. 21, 2008

(65) Prior Publication Data

US 2008/0234827 A1 Sep. 25, 2008

Related U.S. Application Data

(63) Continuation-in-part of application No. 11/464,782, filed on Aug. 15, 2006, now Pat. No. 7,785,368, and a continuation-in-part of application No. 11/464,790, filed on Aug. 15, 2006, now Pat. No. 7,666,226, and a continuation-in-part of application No. 11/464,793, filed on Aug. 15, 2006, now Pat. No. 7,666,227, and a continuation-in-part of application No. 11/464,807, filed on Aug. 15, 2006, now Pat. No. 8,057,544, and a continuation-in-part of application No. 11/464,812, filed on Aug. 15, 2006, now Pat. No. 7,670,374, and a continuation-in-part of application No. 11/464,815, filed on Aug. 15, 2006, now Pat. No. 7,670,375.

(60) Provisional application No. 60/708,691, filed on Aug. 16, 2005, provisional application No. 60/738,432, filed on Nov. 21, 2005, provisional application No. 60/784,185, filed on Mar. 21, 2006, provisional application No. 60/890,868, filed on Feb. 21, 2007, provisional application No. 60/936,974, filed on Jun. 22, 2007.

(51) Int. Cl.  
*A61F 2/44* (2006.01)  
*A61B 17/88* (2006.01)

(52) U.S. Cl.  
USPC ........ 623/17.11; 623/17.16; 606/90; 606/279

(58) Field of Classification Search  
USPC ........................ 623/17.11–17.16; 606/279, 90  
See application file for complete search history.

(56) References Cited

U.S. PATENT DOCUMENTS

| 1,965,653 | A | 7/1934 | Kennedy |
| 3,091,237 | A | 5/1963 | Skinner |

(Continued)

FOREIGN PATENT DOCUMENTS

| DE | 197 10 392 C1 * | 7/1999 | ............... A61F 2/44 |
| DE | 19710392 C1 | 7/1999 | |

(Continued)

OTHER PUBLICATIONS

USPTO Notice of Allowance and Fee(s) Due of Dec. 23, 2009 for U.S. Appl. No. 11/464,790.

(Continued)

*Primary Examiner* — Eduardo C Robert  
*Assistant Examiner* — Julianna N Harvey  
(74) *Attorney, Agent, or Firm* — Cook Alex Ltd.

(57) ABSTRACT

Various features of spinal implants and systems and methods for implanting the same with or between tissue layers in the human body.

86 Claims, 25 Drawing Sheets

(56) References Cited

U.S. PATENT DOCUMENTS

| | | | |
|---|---|---|---|
| 3,112,743 A | 12/1963 | Cochran et al. |
| 3,648,294 A | 3/1972 | Shahrestani |
| 3,800,788 A | 4/1974 | White |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 4,262,676 A | 4/1981 | Jamshidi |
| 4,274,163 A | 6/1981 | Malcom et al. |
| 4,312,337 A | 1/1982 | Donohue |
| 4,313,434 A | 2/1982 | Segal |
| 4,399,814 A | 8/1983 | Pratt, Jr. et al. |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,630,616 A | 12/1986 | Tretinyak |
| 4,665,906 A | 5/1987 | Jervis |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,743,256 A | 5/1988 | Brantigan |
| 4,772,287 A | 9/1988 | Ray et al. |
| 4,834,069 A | 5/1989 | Umeda |
| 4,838,282 A | 6/1989 | Strasser et al. |
| 4,863,476 A | 9/1989 | Shepperd |
| 4,878,915 A | 11/1989 | Brantigan |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,898,577 A | 2/1990 | Badger et al. |
| 4,904,261 A | 2/1990 | Dove et al. |
| 4,941,466 A | 7/1990 | Romano |
| 4,961,740 A | 10/1990 | Ray et al. |
| 4,969,888 A | 11/1990 | Scholten et al. |
| 5,015,247 A | 5/1991 | Michelson |
| 5,015,255 A | 5/1991 | Kuslich |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,071,435 A | 12/1991 | Fuchs et al. |
| 5,098,435 A | 3/1992 | Stednitz et al. |
| 5,102,413 A | 4/1992 | Poddar |
| 5,108,404 A | 4/1992 | Scholten et al. |
| 5,122,130 A | 6/1992 | Keller |
| 5,123,926 A | 6/1992 | Pisharodi |
| 5,147,366 A | 9/1992 | Arroyo et al. |
| 5,163,989 A | 11/1992 | Campbell et al. |
| 5,171,280 A | 12/1992 | Baumgartner |
| 5,176,683 A | 1/1993 | Kimsey et al. |
| 5,176,692 A | 1/1993 | Wilk et al. |
| 5,183,052 A | 2/1993 | Terwilliger |
| 5,192,327 A | 3/1993 | Brantigan |
| 5,228,441 A | 7/1993 | Lundquist |
| 5,242,448 A | 9/1993 | Pettine et al. |
| 5,242,879 A | 9/1993 | Abe et al. |
| 5,257,632 A | 11/1993 | Turkel et al. |
| 5,263,953 A | 11/1993 | Bagby |
| 5,285,795 A | 2/1994 | Ryan et al. |
| 5,303,718 A | 4/1994 | Krajicek |
| 5,306,308 A | 4/1994 | Gross et al. |
| 5,306,310 A | 4/1994 | Siebels |
| 5,322,505 A | 6/1994 | Krause et al. |
| 5,330,429 A | 7/1994 | Noguchi et al. |
| 5,331,975 A | 7/1994 | Bonutti |
| 5,361,752 A | 11/1994 | Moll et al. |
| 5,383,932 A | 1/1995 | Wilson et al. |
| 5,385,151 A | 1/1995 | Scarfone et al. |
| 5,423,816 A | 6/1995 | Lin |
| 5,423,817 A | 6/1995 | Lin |
| 5,423,850 A | 6/1995 | Berger |
| 5,431,658 A | 7/1995 | Moskovich |
| 5,441,538 A | 8/1995 | Bonutti |
| 5,454,365 A | 10/1995 | Bonutti |
| 5,454,827 A | 10/1995 | Aust et al. |
| 5,462,563 A | 10/1995 | Shearer et al. |
| 5,468,245 A | 11/1995 | Vargas, III |
| 5,480,400 A | 1/1996 | Berger |
| 5,484,437 A | 1/1996 | Michelson |
| 5,509,923 A | 4/1996 | Middleman et al. |
| 5,514,143 A | 5/1996 | Bonutti et al. |
| 5,514,153 A | 5/1996 | Bonutti |
| 5,522,398 A | 6/1996 | Goldenberg et al. |
| 5,522,790 A | 6/1996 | Moll et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,538,009 A | 7/1996 | Byrne et al. |
| 5,540,711 A | 7/1996 | Kieturakis et al. |
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,593,409 A | 1/1997 | Michelson |
| 5,601,556 A | 2/1997 | Pisharodi |
| 5,601,572 A | 2/1997 | Middleman et al. |
| 5,632,746 A | 5/1997 | Middleman et al. |
| 5,645,597 A | 7/1997 | Krapiva |
| 5,665,122 A | 9/1997 | Kambin |
| 5,669,926 A | 9/1997 | Aust et al. |
| 5,674,295 A | 10/1997 | Ray et al. |
| 5,681,263 A | 10/1997 | Flesch |
| 5,693,100 A | 12/1997 | Pisharodi |
| 5,695,513 A | 12/1997 | Johnson et al. |
| 5,700,239 A | 12/1997 | Yoon |
| 5,702,453 A | 12/1997 | Rabbe et al. |
| 5,702,454 A | 12/1997 | Baumgartner |
| 5,716,416 A | 2/1998 | Lin |
| 5,741,253 A | 4/1998 | Michelson |
| 5,749,879 A | 5/1998 | Middleman et al. |
| 5,755,797 A | 5/1998 | Baumgartner |
| 5,756,127 A | 5/1998 | Grisoni et al. |
| 5,766,252 A * | 6/1998 | Henry et al. ............... 623/17.16 |
| 5,772,661 A | 6/1998 | Michelson |
| 5,782,832 A | 7/1998 | Larsen et al. |
| 5,788,703 A | 8/1998 | Mittelmeier et al. |
| 5,807,275 A | 9/1998 | Jamshidi |
| 5,820,628 A | 10/1998 | Middleman et al. |
| 5,823,979 A | 10/1998 | Mezo |
| 5,824,093 A | 10/1998 | Ray et al. |
| 5,827,289 A | 10/1998 | Reiley et al. |
| 5,836,948 A | 11/1998 | Zucherman et al. |
| 5,848,986 A | 12/1998 | Lundquist et al. |
| 5,851,212 A | 12/1998 | Zirps et al. |
| 5,860,977 A | 1/1999 | Zucherman et al. |
| 5,865,848 A | 2/1999 | Baker |
| 5,904,690 A | 5/1999 | Middleman et al. |
| 5,919,235 A * | 7/1999 | Husson et al. ............. 623/17.16 |
| 5,925,074 A | 7/1999 | Gingras et al. |
| 5,961,554 A | 10/1999 | Janson et al. |
| 5,972,015 A | 10/1999 | Scribner et al. |
| 5,976,186 A | 11/1999 | Bao et al. |
| 5,980,522 A | 11/1999 | Koros et al. |
| 6,012,494 A | 1/2000 | Balazs |
| 6,015,436 A | 1/2000 | Schonhoffer |
| 6,019,793 A | 2/2000 | Perren et al. |
| 6,030,401 A | 2/2000 | Marino |
| 6,033,406 A | 3/2000 | Mathews |
| 6,033,412 A | 3/2000 | Losken et al. |
| 6,039,740 A | 3/2000 | Olerud |
| 6,045,552 A | 4/2000 | Zucherman et al. |

| | | | |
|---|---|---|---|
| 6,048,342 A | 4/2000 | Zucherman et al. | |
| 6,048,346 A | 4/2000 | Reiley et al. | |
| 6,048,360 A | 4/2000 | Khosravi et al. | |
| 6,066,154 A | 5/2000 | Reiley et al. | |
| 6,068,630 A | 5/2000 | Zucherman et al. | |
| 6,073,051 A | 6/2000 | Sharkey et al. | |
| 6,083,225 A | 7/2000 | Winslow et al. | |
| 6,090,143 A | 7/2000 | Meriwether et al. | |
| 6,096,080 A * | 8/2000 | Nicholson et al. | 623/17.16 |
| 6,102,950 A | 8/2000 | Vaccaro | |
| 6,110,210 A | 8/2000 | Norton et al. | |
| 6,113,640 A | 9/2000 | Tormala et al. | |
| 6,119,044 A | 9/2000 | Kuzma | |
| 6,123,705 A | 9/2000 | Michelson | |
| 6,126,660 A | 10/2000 | Dietz | |
| 6,127,597 A | 10/2000 | Beyar et al. | |
| 6,159,211 A | 12/2000 | Boriani et al. | |
| 6,159,244 A | 12/2000 | Suddaby | |
| 6,165,218 A | 12/2000 | Husson et al. | |
| 6,174,337 B1 | 1/2001 | Keenan | |
| 6,179,873 B1 | 1/2001 | Zientek | |
| 6,187,048 B1 | 2/2001 | Milner et al. | |
| 6,190,414 B1 | 2/2001 | Young et al. | |
| 6,193,757 B1 | 2/2001 | Foley et al. | |
| 6,197,033 B1 | 3/2001 | Haid, Jr. et al. | |
| D439,980 S | 4/2001 | Reiley et al. | |
| 6,217,579 B1 | 4/2001 | Koros | |
| 6,221,082 B1 | 4/2001 | Marino et al. | |
| 6,224,603 B1 | 5/2001 | Marino | |
| 6,235,030 B1 | 5/2001 | Zucherman et al. | |
| 6,235,043 B1 | 5/2001 | Reiley et al. | |
| 6,238,491 B1 | 5/2001 | Davidson et al. | |
| 6,241,734 B1 | 6/2001 | Scribner et al. | |
| 6,248,110 B1 | 6/2001 | Reiley et al. | |
| 6,251,140 B1 | 6/2001 | Marino et al. | |
| 6,261,289 B1 | 7/2001 | Levy | |
| 6,264,695 B1 | 7/2001 | Stoy | |
| 6,267,763 B1 | 7/2001 | Castro | |
| 6,280,447 B1 * | 8/2001 | Marino et al. | 606/88 |
| 6,280,456 B1 | 8/2001 | Scribner et al. | |
| 6,280,475 B1 | 8/2001 | Bao et al. | |
| 6,290,724 B1 | 9/2001 | Marino | |
| D449,691 S | 10/2001 | Reiley et al. | |
| 6,296,647 B1 | 10/2001 | Robioneck et al. | |
| 6,312,443 B1 | 11/2001 | Stone | |
| 6,364,828 B1 | 4/2002 | Yeung et al. | |
| 6,368,325 B1 | 4/2002 | McKinley et al. | |
| 6,387,130 B1 | 5/2002 | Stone et al. | |
| 6,402,750 B1 | 6/2002 | Atkinson et al. | |
| 6,419,641 B1 | 7/2002 | Mark et al. | |
| 6,419,705 B1 | 7/2002 | Erickson | |
| 6,423,071 B1 | 7/2002 | Lawson | |
| 6,423,083 B2 | 7/2002 | Reiley et al. | |
| 6,423,089 B1 | 7/2002 | Gingras et al. | |
| 6,425,887 B1 | 7/2002 | McGuckin et al. | |
| 6,425,919 B1 | 7/2002 | Lambrecht | |
| 6,428,541 B1 | 8/2002 | Boyd et al. | |
| 6,436,140 B1 | 8/2002 | Liu et al. | |
| 6,440,138 B1 | 8/2002 | Reiley et al. | |
| 6,451,019 B1 | 9/2002 | Zucherman et al. | |
| 6,468,279 B1 | 10/2002 | Reo | |
| 6,478,805 B1 | 11/2002 | Marino et al. | |
| 6,482,235 B1 | 11/2002 | Lambrecht et al. | |
| 6,485,518 B1 | 11/2002 | Cornwall et al. | |
| D467,657 S | 12/2002 | Scribner | |
| 6,488,710 B2 | 12/2002 | Besselink | |
| 6,491,626 B1 | 12/2002 | Stone et al. | |
| 6,491,695 B1 | 12/2002 | Roggenbuck | |
| 6,498,421 B1 | 12/2002 | Oh et al. | |
| 6,500,178 B2 | 12/2002 | Zucherman et al. | |
| 6,500,205 B1 | 12/2002 | Michelson | |
| 6,508,839 B1 | 1/2003 | Lambrecht et al. | |
| 6,511,471 B2 | 1/2003 | Rosenman et al. | |
| 6,512,958 B1 | 1/2003 | Swoyer et al. | |
| D469,871 S | 2/2003 | Sand | |
| 6,520,991 B2 | 2/2003 | Huene | |
| D472,323 S | 3/2003 | Sand | |
| 6,530,930 B1 | 3/2003 | Marino et al. | |
| 6,533,791 B1 | 3/2003 | Betz et al. | |
| 6,533,797 B1 | 3/2003 | Stone et al. | |
| 6,540,747 B1 | 4/2003 | Marino | |
| 6,554,833 B2 | 4/2003 | Levy et al. | |
| 6,558,390 B2 | 5/2003 | Cragg | |
| 6,562,074 B2 | 5/2003 | Gerbec et al. | |
| 6,575,919 B1 | 6/2003 | Reiley et al. | |
| 6,575,979 B1 | 6/2003 | Cragg | |
| 6,576,016 B1 | 6/2003 | Hochshuler et al. | |
| 6,579,291 B1 | 6/2003 | Keith et al. | |
| 6,582,431 B1 | 6/2003 | Ray | |
| 6,582,433 B2 | 6/2003 | Yun | |
| 6,595,998 B2 | 7/2003 | Johnson et al. | |
| 6,599,294 B2 | 7/2003 | Fuss et al. | |
| 6,602,293 B1 | 8/2003 | Biermann et al. | |
| 6,607,530 B1 | 8/2003 | Carl et al. | |
| 6,607,544 B1 | 8/2003 | Boucher et al. | |
| 6,610,094 B2 | 8/2003 | Husson | |
| 6,613,054 B2 | 9/2003 | Scribner et al. | |
| 6,620,196 B1 | 9/2003 | Trieu | |
| 6,623,505 B2 | 9/2003 | Scribner et al. | |
| D482,787 S | 11/2003 | Reiss | |
| 6,641,587 B2 | 11/2003 | Scribner et al. | |
| 6,645,213 B2 | 11/2003 | Sand et al. | |
| 6,648,917 B2 | 11/2003 | Gerbec et al. | |
| D483,495 S | 12/2003 | Sand | |
| 6,656,178 B1 | 12/2003 | Veldhuizen et al. | |
| 6,656,180 B2 | 12/2003 | Stahurski | |
| 6,660,037 B1 | 12/2003 | Husson et al. | |
| 6,663,647 B2 | 12/2003 | Reiley et al. | |
| 6,666,890 B2 | 12/2003 | Michelson | |
| 6,666,891 B2 | 12/2003 | Boehm, Jr. et al. | |
| 6,676,663 B2 | 1/2004 | Higueras et al. | |
| 6,676,665 B2 | 1/2004 | Foley et al. | |
| 6,682,561 B2 | 1/2004 | Songer et al. | |
| 6,685,742 B1 | 2/2004 | Jackson | |
| 6,689,125 B1 | 2/2004 | Keith et al. | |
| 6,689,168 B2 | 2/2004 | Lieberman | |
| 6,692,563 B2 | 2/2004 | Zimmermann | |
| 6,706,070 B1 | 3/2004 | Wagner et al. | |
| 6,716,216 B1 | 4/2004 | Boucher et al. | |
| 6,716,247 B2 | 4/2004 | Michelson | |
| 6,716,957 B2 | 4/2004 | Tunc | |
| 6,719,761 B1 | 4/2004 | Reiley et al. | |
| 6,719,773 B1 | 4/2004 | Boucher et al. | |
| 6,723,128 B2 | 4/2004 | Uk | |
| 6,726,691 B2 | 4/2004 | Osorio et al. | |
| D490,159 S | 5/2004 | Sand | |
| 6,740,093 B2 | 5/2004 | Hochschuler et al. | |
| D492,032 S | 6/2004 | Muller et al. | |
| 6,749,560 B1 | 6/2004 | Konstorum et al. | |
| 6,755,841 B2 | 6/2004 | Fraser et al. | |
| D492,775 S | 7/2004 | Doelling et al. | |
| D493,533 S | 7/2004 | Blain | |
| 6,758,673 B2 | 7/2004 | Fromovich et al. | |
| 6,764,514 B1 | 7/2004 | Li et al. | |
| D495,417 S | 8/2004 | Doelling et al. | |
| 6,773,460 B2 | 8/2004 | Jackson | |
| 6,780,151 B2 | 8/2004 | Grabover et al. | |
| 6,783,530 B1 | 8/2004 | Levy | |
| 6,793,679 B2 | 9/2004 | Michelson | |
| 6,796,983 B2 | 9/2004 | Zucherman et al. | |
| 6,805,695 B2 | 10/2004 | Keith et al. | |
| 6,805,697 B1 | 10/2004 | Helm et al. | |
| 6,808,537 B2 | 10/2004 | Michelson | |
| 6,814,736 B2 | 11/2004 | Reiley et al. | |
| 6,814,756 B1 | 11/2004 | Michelson | |
| 6,821,298 B1 | 11/2004 | Jackson | |
| 6,830,589 B2 | 12/2004 | Erickson | |
| 6,835,205 B2 | 12/2004 | Atkinson et al. | |
| 6,835,206 B2 | 12/2004 | Jackson | |
| 6,840,944 B2 | 1/2005 | Suddaby | |
| 6,852,126 B2 | 2/2005 | Ahlgren | |
| 6,852,129 B2 | 2/2005 | Gerbec et al. | |
| 6,863,668 B2 | 3/2005 | Gillespie et al. | |
| 6,863,672 B2 | 3/2005 | Reiley et al. | |
| 6,863,673 B2 | 3/2005 | Gerbec et al. | |
| 6,866,682 B1 | 3/2005 | An et al. | |
| 6,881,228 B2 | 4/2005 | Zdeblick et al. | |

| | | |
|---|---|---|
| 6,883,520 B2 | 4/2005 | Lambrecht et al. |
| 6,887,248 B2 | 5/2005 | McKinley et al. |
| 6,893,466 B2 | 5/2005 | Trieu |
| 6,899,716 B2 | 5/2005 | Cragg |
| 6,899,719 B2 | 5/2005 | Reiley et al. |
| D506,828 S | 6/2005 | Layne et al. |
| 6,905,512 B2 | 6/2005 | Paes et al. |
| 6,908,506 B2 | 6/2005 | Zimmermann |
| 6,921,403 B2 | 7/2005 | Cragg et al. |
| 6,923,810 B1 | 8/2005 | Michelson |
| 6,923,813 B2 | 8/2005 | Phillips et al. |
| 6,923,814 B1 | 8/2005 | Hildebrand et al. |
| 6,929,647 B2 | 8/2005 | Cohen |
| 6,945,973 B2 | 9/2005 | Bray |
| 6,952,129 B2 | 10/2005 | Lin et al. |
| 6,962,606 B2 | 11/2005 | Michelson |
| 6,964,674 B1 | 11/2005 | Matsuura et al. |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,415 B1 | 3/2006 | McKay |
| 7,018,453 B2 | 3/2006 | Klein et al. |
| 7,029,498 B2 | 4/2006 | Boehm et al. |
| 7,044,954 B2 | 5/2006 | Reiley et al. |
| 7,048,694 B2 | 5/2006 | Mark et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,220,281 B2 | 5/2007 | Lambrecht et al. |
| 7,223,227 B2 | 5/2007 | Pflueger |
| 7,226,481 B2 | 6/2007 | Kuslich |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,322,962 B2 | 1/2008 | Forrest |
| 7,383,639 B2 | 6/2008 | Malandain |
| 7,485,134 B2 | 2/2009 | Simonson |
| 7,608,083 B2 | 10/2009 | Lee et al. |
| 7,637,905 B2 | 12/2009 | Saadat et al. |
| 7,828,807 B2 | 11/2010 | LeHuec et al. |
| 8,187,327 B2 | 5/2012 | Edidin et al. |
| 8,236,029 B2 | 8/2012 | Siegal |
| 2001/0011174 A1 | 8/2001 | Reiley et al. |
| 2001/0016741 A1 | 8/2001 | Burkus et al. |
| 2002/0016583 A1 | 2/2002 | Cragg |
| 2002/0026195 A1 | 2/2002 | Layne et al. |
| 2002/0026244 A1 | 2/2002 | Trieu |
| 2002/0045942 A1 | 4/2002 | Ham |
| 2002/0068974 A1 | 6/2002 | Kuslich et al. |
| 2002/0077700 A1 | 6/2002 | Varga et al. |
| 2002/0082584 A1 | 6/2002 | Rosenman et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1* | 8/2002 | Steinberg ................ 623/17.12 |
| 2002/0156482 A1 | 10/2002 | Scribner et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1* | 12/2002 | Johnson et al. ................ 606/90 |
| 2002/0183778 A1 | 12/2002 | Reiley et al. |
| 2002/0191487 A1 | 12/2002 | Sand |
| 2003/0018390 A1 | 1/2003 | Husson |
| 2003/0032963 A1 | 2/2003 | Reiss et al. |
| 2003/0040796 A1 | 2/2003 | Ferree |
| 2003/0045937 A1 | 3/2003 | Ginn |
| 2003/0050644 A1 | 3/2003 | Boucher et al. |
| 2003/0069593 A1 | 4/2003 | Tremulis et al. |
| 2003/0074075 A1 | 4/2003 | Thomas, Jr. et al. |
| 2003/0108588 A1 | 6/2003 | Chen et al. |
| 2003/0130664 A1 | 7/2003 | Boucher et al. |
| 2003/0171812 A1 | 9/2003 | Grunberg et al. |
| 2003/0187445 A1 | 10/2003 | Keith et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin, Jr. |
| 2003/0208136 A1 | 11/2003 | Mark et al. |
| 2003/0220648 A1 | 11/2003 | Osorio et al. |
| 2003/0220695 A1 | 11/2003 | Sevrain |
| 2003/0229372 A1 | 12/2003 | Reiley et al. |
| 2003/0233096 A1 | 12/2003 | Osorio et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas, Jr. et al. |
| 2004/0024465 A1 | 2/2004 | Lambrecht et al. |
| 2004/0034343 A1 | 2/2004 | Gillespie et al. |
| 2004/0034429 A1 | 2/2004 | Lambrecht et al. |
| 2004/0049203 A1 | 3/2004 | Scribner et al. |
| 2004/0059333 A1 | 3/2004 | Carl et al. |
| 2004/0059339 A1 | 3/2004 | Roehm, III et al. |
| 2004/0059418 A1 | 3/2004 | McKay et al. |
| 2004/0064144 A1 | 4/2004 | Johnson et al. |
| 2004/0073308 A1 | 4/2004 | Kuslich et al. |
| 2004/0082953 A1 | 4/2004 | Petit |
| 2004/0087947 A1 | 5/2004 | Lim et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray, III et al. |
| 2004/0098131 A1 | 5/2004 | Bryan et al. |
| 2004/0102774 A1 | 5/2004 | Trieu |
| 2004/0106940 A1 | 6/2004 | Shaolian et al. |

| | | |
|---|---|---|
| 2004/0111161 A1 | 6/2004 | Trieu |
| 2004/0117019 A1 | 6/2004 | Trieu et al. |
| 2004/0133124 A1 | 7/2004 | Bates et al. |
| 2004/0133229 A1 | 7/2004 | Lambrecht et al. |
| 2004/0133280 A1 | 7/2004 | Trieu |
| 2004/0138748 A1 | 7/2004 | Boyer, II et al. |
| 2004/0153064 A1 | 8/2004 | Foley et al. |
| 2004/0153115 A1 | 8/2004 | Reiley et al. |
| 2004/0158206 A1 | 8/2004 | Aboul-Hosn et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0176775 A1 | 9/2004 | Burkus et al. |
| 2004/0186471 A1 | 9/2004 | Trieu |
| 2004/0186528 A1 | 9/2004 | Ries et al. |
| 2004/0186573 A1 | 9/2004 | Ferree |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220672 A1 | 11/2004 | Shadduck |
| 2004/0225296 A1 | 11/2004 | Reiss et al. |
| 2004/0225361 A1* | 11/2004 | Glenn et al. ............... 623/17.12 |
| 2004/0230191 A1 | 11/2004 | Frey et al. |
| 2004/0230309 A1* | 11/2004 | DiMauro et al. ........... 623/17.12 |
| 2004/0243229 A1 | 12/2004 | Vidlund et al. |
| 2004/0249377 A1 | 12/2004 | Kaes et al. |
| 2004/0254520 A1 | 12/2004 | Porteous et al. |
| 2004/0254644 A1 | 12/2004 | Taylor |
| 2004/0260300 A1 | 12/2004 | Gorensek et al. |
| 2004/0260397 A1 | 12/2004 | Lambrecht et al. |
| 2004/0267271 A9 | 12/2004 | Scribner et al. |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0033295 A1 | 2/2005 | Wisnewski |
| 2005/0033440 A1 | 2/2005 | Lambrecht et al. |
| 2005/0038517 A1* | 2/2005 | Carrison et al. ........... 623/17.16 |
| 2005/0043737 A1 | 2/2005 | Reiley et al. |
| 2005/0043796 A1 | 2/2005 | Grant et al. |
| 2005/0054948 A1* | 3/2005 | Goldenberg ................. 600/567 |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080488 A1 | 4/2005 | Schultz |
| 2005/0085912 A1 | 4/2005 | Arnin et al. |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0107880 A1 | 5/2005 | Shimp et al. |
| 2005/0113918 A1 | 5/2005 | Messerli et al. |
| 2005/0113919 A1 | 5/2005 | Cragg et al. |
| 2005/0113928 A1 | 5/2005 | Cragg et al. |
| 2005/0118228 A1 | 6/2005 | Trieu |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125066 A1 | 6/2005 | McAfee |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131536 A1 | 6/2005 | Eisermann et al. |
| 2005/0131540 A1 | 6/2005 | Trieu |
| 2005/0131541 A1 | 6/2005 | Trieu |
| 2005/0137602 A1 | 6/2005 | Assell et al. |
| 2005/0142211 A1 | 6/2005 | Wenz |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154463 A1 | 7/2005 | Trieu |
| 2005/0165406 A1 | 7/2005 | Assell et al. |
| 2005/0171539 A1 | 8/2005 | Braun et al. |
| 2005/0171552 A1 | 8/2005 | Johnson et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197707 A1 | 9/2005 | Trieu et al. |
| 2005/0216018 A1 | 9/2005 | Sennett |
| 2005/0216087 A1 | 9/2005 | Zucherman et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251149 A1 | 11/2005 | Wenz |
| 2005/0251260 A1 | 11/2005 | Gerber et al. |
| 2005/0261684 A1 | 11/2005 | Shaolian et al. |
| 2005/0261695 A1 | 11/2005 | Cragg et al. |
| 2005/0261781 A1 | 11/2005 | Sennett et al. |
| 2005/0273166 A1 | 12/2005 | Sweeney |
| 2005/0273173 A1 | 12/2005 | Gordon |
| 2005/0278023 A1 | 12/2005 | Zwirkoski |
| 2005/0278027 A1 | 12/2005 | Hyde, Jr. |
| 2005/0278029 A1 | 12/2005 | Trieu |
| 2005/0283244 A1 | 12/2005 | Gordon et al. |
| 2005/0287071 A1 | 12/2005 | Wenz |
| 2006/0004456 A1 | 1/2006 | McKay |
| 2006/0009779 A1 | 1/2006 | Collins et al. |
| 2006/0030850 A1 | 2/2006 | Keegan et al. |
| 2006/0030943 A1 | 2/2006 | Peterman |
| 2006/0036241 A1 | 2/2006 | Siegal |
| 2006/0036259 A1 | 2/2006 | Carl et al. |
| 2006/0036261 A1 | 2/2006 | McDonnell |
| 2006/0036273 A1 | 2/2006 | Siegal |
| 2006/0058807 A1 | 3/2006 | Landry et al. |
| 2006/0058880 A1 | 3/2006 | Wysocki et al. |
| 2006/0064171 A1 | 3/2006 | Trieu |
| 2006/0064172 A1 | 3/2006 | Trieu |
| 2006/0069439 A1 | 3/2006 | Zucherman et al. |
| 2006/0069440 A1 | 3/2006 | Zucherman et al. |
| 2006/0085002 A1 | 4/2006 | Trieu et al. |
| 2006/0085009 A1 | 4/2006 | Truckai et al. |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100706 A1 | 5/2006 | Shadduck et al. |
| 2006/0106397 A1 | 5/2006 | Lins |
| 2006/0106459 A1 | 5/2006 | Truckai et al. |
| 2006/0122704 A1 | 6/2006 | Vresilovic et al. |
| 2006/0129244 A1 | 6/2006 | Ensign |
| 2006/0136064 A1 | 6/2006 | Sherman |

| | | |
|---|---|---|
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0155379 A1 | 7/2006 | Heneveld, Sr. et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen, III et al. |
| 2006/0173545 A1 | 8/2006 | Cauthen, III et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195191 A1 | 8/2006 | Sweeney, II et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0241663 A1 | 10/2006 | Rice et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1* | 12/2006 | Segal et al. ................ 623/17.12 |
| 2006/0293662 A1 | 12/2006 | Boyer, II et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010889 A1 | 1/2007 | Francis |
| 2007/0032703 A1 | 2/2007 | Sankaran et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093899 A1 | 4/2007 | Dutoit et al. |
| 2007/0093906 A1 | 4/2007 | Hudgins et al. |
| 2007/0123986 A1 | 5/2007 | Schaller |
| 2007/0135922 A1 | 6/2007 | Trieu |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0179612 A1 | 8/2007 | Johnson et al. |
| 2007/0179615 A1 | 8/2007 | Heinz et al. |
| 2007/0179616 A1 | 8/2007 | Braddock, Jr. et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0208426 A1 | 9/2007 | Trieu |
| 2007/0213717 A1 | 9/2007 | Trieu et al. |
| 2007/0219634 A1 | 9/2007 | Greenhalgh et al. |
| 2007/0233074 A1 | 10/2007 | Anderson et al. |
| 2007/0260255 A1 | 11/2007 | Haddock et al. |
| 2007/0270957 A1 | 11/2007 | Heinz |
| 2007/0282443 A1 | 12/2007 | Globerman et al. |
| 2008/0021557 A1 | 1/2008 | Trieu |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0051897 A1 | 2/2008 | Lopez et al. |
| 2008/0071356 A1 | 3/2008 | Greenhalgh et al. |
| 2008/0097611 A1 | 4/2008 | Mastrorio et al. |
| 2008/0125865 A1 | 5/2008 | Abdelgany |
| 2008/0140207 A1 | 6/2008 | Olmos et al. |
| 2008/0167657 A1 | 7/2008 | Greenhalgh |
| 2008/0177306 A1 | 7/2008 | Lamborne et al. |
| 2008/0195096 A1* | 8/2008 | Frei ................................ 606/60 |
| 2008/0195210 A1 | 8/2008 | Milijasevic et al. |
| 2008/0221687 A1 | 9/2008 | Viker |
| 2008/0229597 A1 | 9/2008 | Malandain |
| 2008/0243251 A1 | 10/2008 | Stad et al. |
| 2008/0281346 A1 | 11/2008 | Greenhalgh et al. |
| 2008/0281364 A1 | 11/2008 | Chirico et al. |
| 2009/0018524 A1 | 1/2009 | Greenhalgh et al. |
| 2009/0030423 A1 | 1/2009 | Puno |
| 2009/0048678 A1 | 2/2009 | Saal et al. |

FOREIGN PATENT DOCUMENTS

| | | |
|---|---|---|
| DE | 19710392 C1 | 7/1999 |
| DE | 202006005868 | 6/2006 |
| EP | 0529275 A2 | 3/1993 |
| EP | 0 621 020 A1 | 10/1994 |
| EP | 0743045 | 11/1996 |
| EP | 1 157 676 A1 | 4/2001 |
| EP | 1157676 A1 | 11/2001 |

(56) References Cited

FOREIGN PATENT DOCUMENTS

| | | |
|---|---|---|
| FR | 2712486 A1 | 5/1995 |
| FR | 2 913 331 | 12/2008 |
| WO | WO 93/04634 | 3/1993 |
| WO | 0044288 A1 | 3/2000 |
| WO | WO 00/67650 | 11/2000 |
| WO | WO 00/67651 | 11/2000 |
| WO | WO 01/10316 A1 | 2/2001 |
| WO | WO 02/17824 A2 | 3/2002 |
| WO | WO 02/30338 A1 | 4/2002 |
| WO | WO 02/43628 A1 | 6/2002 |
| WO | WO 02/47563 A1 | 6/2002 |
| WO | WO 02/071921 A2 | 9/2002 |
| WO | WO 03/007854 A1 | 1/2003 |
| WO | WO 03/020169 A2 | 3/2003 |
| WO | WO 03/022165 A1 | 3/2003 |
| WO | WO 03/028587 A2 | 4/2003 |
| WO | WO 03/059180 A2 | 7/2003 |
| WO | WO 03/101308 A1 | 12/2003 |
| WO | WO2004/034924 A2 | 4/2004 |
| WO | WO 2004/062505 A1 | 7/2004 |
| WO | WO 2004/082526 A2 | 9/2004 |
| WO | WO 2004/098420 A2 | 11/2004 |
| WO | WO 2004/108022 A1 | 12/2004 |
| WO | 2005/027734 A2 | 3/2005 |
| WO | WO 2005/032433 A2 | 4/2005 |
| WO | WO 2005/051246 A2 | 6/2005 |
| WO | WO 2005/081877 A2 | 9/2005 |
| WO | WO 2006/047645 A2 | 5/2006 |
| WO | WO 2006/060420 A1 | 6/2006 |
| WO | WO 2006/066228 A2 | 6/2006 |
| WO | WO 2006/072941 A2 | 7/2006 |
| WO | WO 2007/022194 | 2/2007 |
| WO | WO2007/067726 A2 | 6/2007 |

OTHER PUBLICATIONS

USPTO Supplemental Notice of Allowability of Dec. 31, 2009 for U.S. Appl. No. 11/464,790.
USPTO Notice of Allowance and Fee(s) Due of Dec. 23, 2009 for U.S. Appl. No. 11/464,793.
UPSTO Supplemental Notice of Allowability of Dec. 31, 2009 for U.S. Appl. No. 11/464,793.
USPTO Notice of Allowance and Fee(s) Due of Dec. 23, 2009 for U.S. Appl. No. 11/464,812.
USPTO Supplemental Notice of Allowability of Dec. 31, 2009 for U.S. Appl. No. 11/464,812.
USPTO Notice of Allowance and Fee(s) Due of Dec. 17, 2009 for U.S. Appl. No. 11/464,815.
USPTO Supplemental Notice of Allowability of Dec. 31, 2009 for U.S. Appl. No. 11/464,815.
Office Action from U.S. Appl. No. 11/464,807 dated Dec. 22, 2010, 9 pages.
John A. Carrino, Roxanne Chan and Alexander R. Vaccaro, "Vertebral Augmentation: Vertebroplasty and Kyphoplasty", Seminars in Roentgenology, vol. 39, No. 1 Jan. 2004: pp. 68-84.
Ajeya P. Joshi , M.D. and Paul A. Glazer, M.D., "Vertebroplasty: Current Concepts and Outlook", 2003, (9 pages), From: http://www.spineuniverse.com/displayarticle.php/article2076.html.
PCT Invitation to Pay Additional Fees (Form PCT/ISA/206), Re: International application No. PCT/US2006/031861 dated Jan. 15, 2007.
Annex to PCT Invitation to Pay Additional Fees, Re: International application No. PCT/US2006/031861 dated Jan. 15, 2007.
PCT Notification concerning transmittal of International Preliminary report on patentability and PCT Written Opinion of the International Searching Authority, PCT Application No. US2006/031861 dated Feb. 28, 2008.
USPTO Office Action of Apr. 1, 2010 for U.S. Appl. No. 11/464,807.
USPTO Office Action of Jun. 23, 2008 for U.S. Appl. No. 11/464,782.
USPTO Office Action of Oct. 29, 2008 for U.S. Appl. No. 11/464,782.
USPTO Office Action of May 21, 2009 for U.S. Appl. No. 11/464,782.
USPTO Office Action of Jun. 23, 2008 for U.S. Appl. No. 11/464,790.
USPTO Office Action of Oct. 31, 2008 for U.S. Appl. No. 11/464,790.
USPTO Office Action of Apr. 15, 2009 for U.S. Appl. No. 11/464,790.
USPTO Office Action of Jun. 23, 2008 for U.S. Appl. No. 11/464,793.
USPTO Office Action of Oct. 29, 2008 for U.S. Appl. No. 11/464,793.
USPTO Office Action of May 22, 2009 for U.S. Appl. No. 11/464,793.
USPTO Office Action of Aug. 19, 2009 for U.S. Appl. No. 11/464,807.
USPTO Office Action of Jun. 23, 2008 for U.S. Appl. No. 11/464,812.
USPTO Office Action of Oct. 29, 2008 for U.S. Appl. No. 11/464,812.
USPTO Office Action of May 12, 2009 for U.S. Appl. No. 11/464,812.
USPTO Office Action of Jun. 23, 2008 for U.S. Appl. No. 11/464,815.
USPTO Office Action of Oct. 29, 2008 for U.S. Appl. No. 11/464,815.
USPTO Office Action of May 12, 2009 for U.S. Appl. No. 11/464,815.
Notification of Transmittal of International Search Report, International Search Report and Written Opinion for PCT/US08/54590 dated Aug. 22, 2008.
Notification of Transmittal of International Search Report, International Search Report and Written Opinion for PCT/US08/54508 dated Aug. 27, 2008.
U.S. Appl. No. 60/689,570, filed Jun. 13, 2005; Inventor: Tzony Siegal; Title: Directional Drilling System.
Office Action issued in European Patent App. No. 06801545.2 dated May 30, 2011.
Translation of Office Action issued in Japanese Patent App. No. 2008-527067 dated May 13, 2011.
Office Action issued in Australian Patent App. No. 2006279558 dated Aug. 8, 2011.
U.S. Appl. No. 60/557,246, filed Mar. 29, 2004 entitled: Device and Methods to Reduce and Stabilize Broken Bones.
Office Action issued in Canadian Patent Application No. 2,617,872 dated Jul. 13, 2012.
Edeland, H.G., "Some Additional Suggestions for an Intervetebral Disc Prosthesis", J of BioMedical Engr., vol. 7(1) pp. 57-62, Jan. 1985.
Canadian Office Action dated Jan. 2, 2013, for Application No. 2,617,872, entitled: Spinal Tissue Distraction Devices.
USPTO Office Action of May 21, 2012 for U.S. Appl. No. 13/161,956.
USPTO Office Action of Jul. 12, 2012 for U.S. Appl. No. 13/162,021.
Japanese Office Action, mailing date Mar. 7, 2013, for Japanese Patent Application No. 2011-201882.
European search report, dated May 7, 2013, for Application No. 08730333.5-1506/2124777 PCT/US2008054508.

* cited by examiner

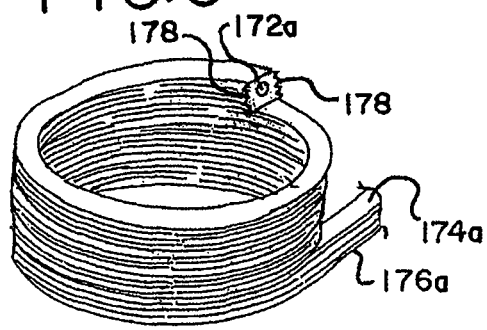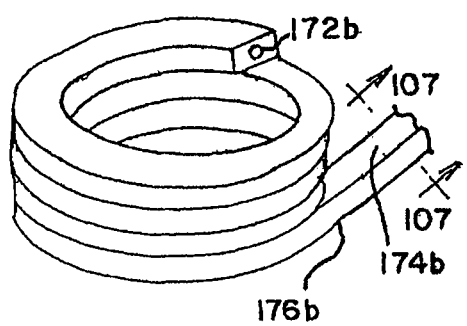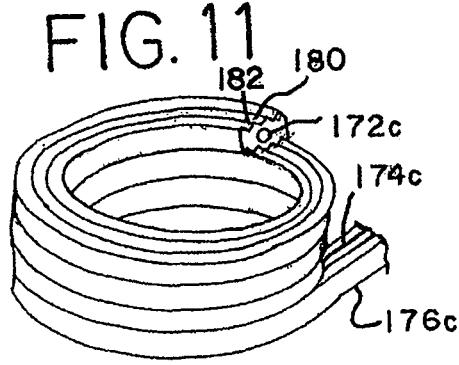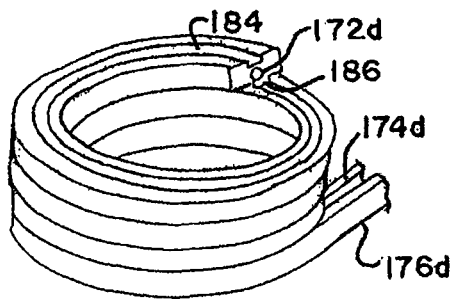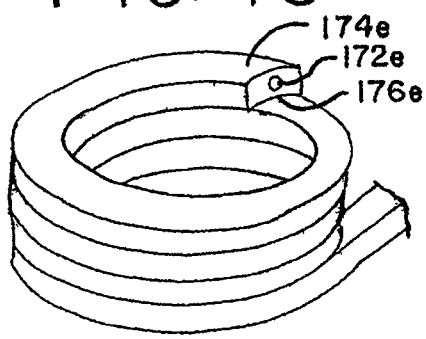

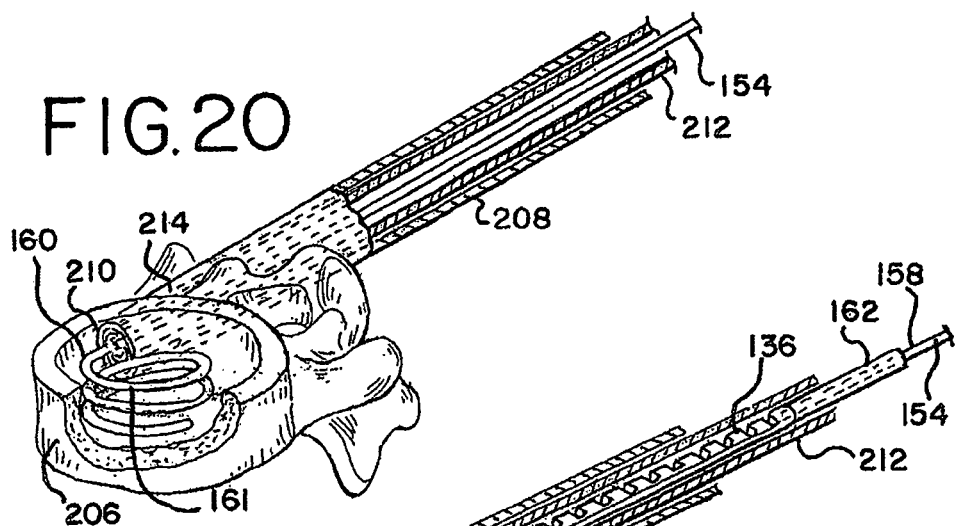
FIG. 20
FIG. 21
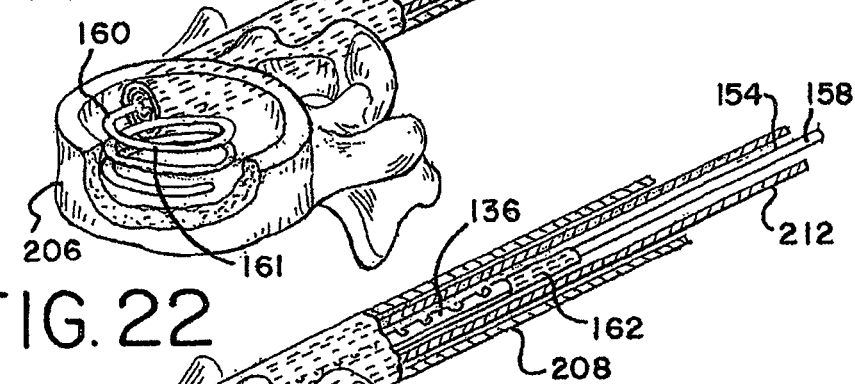
FIG. 22
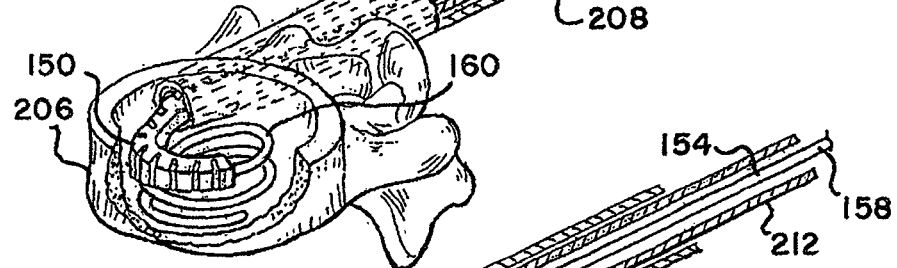
FIG. 23
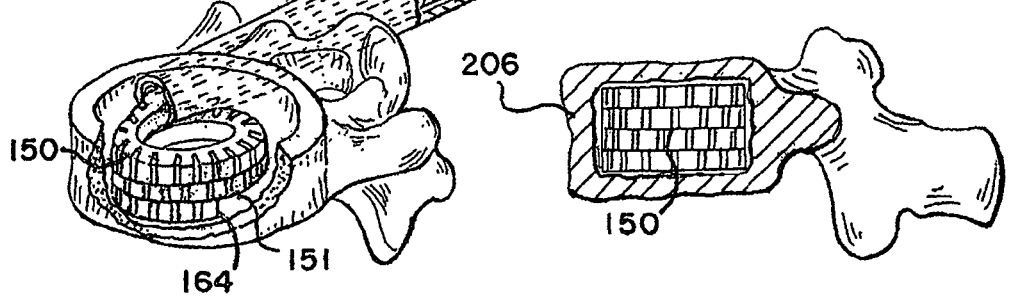
FIG. 24
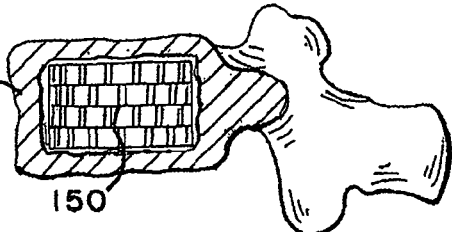

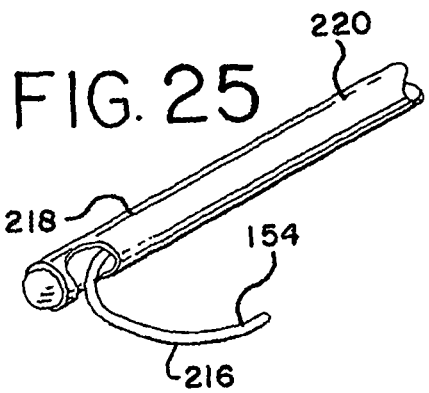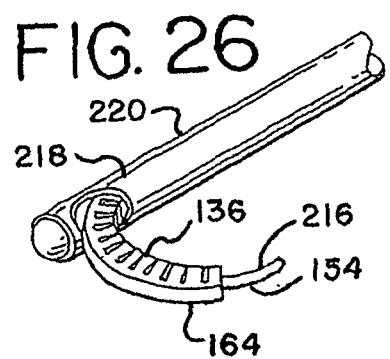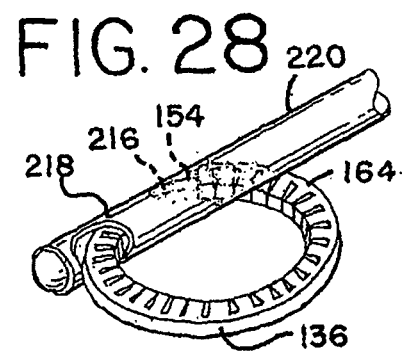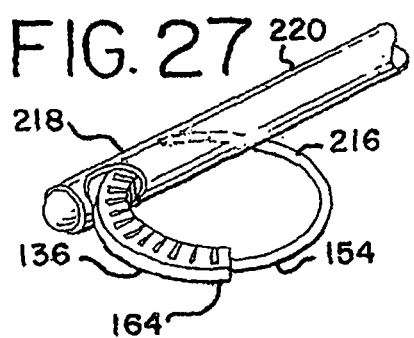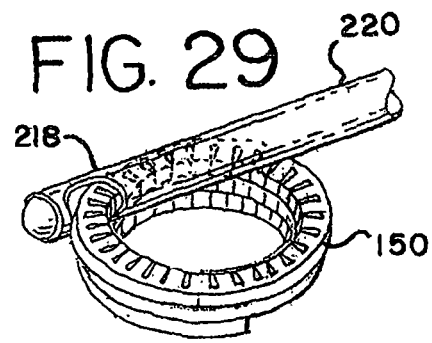

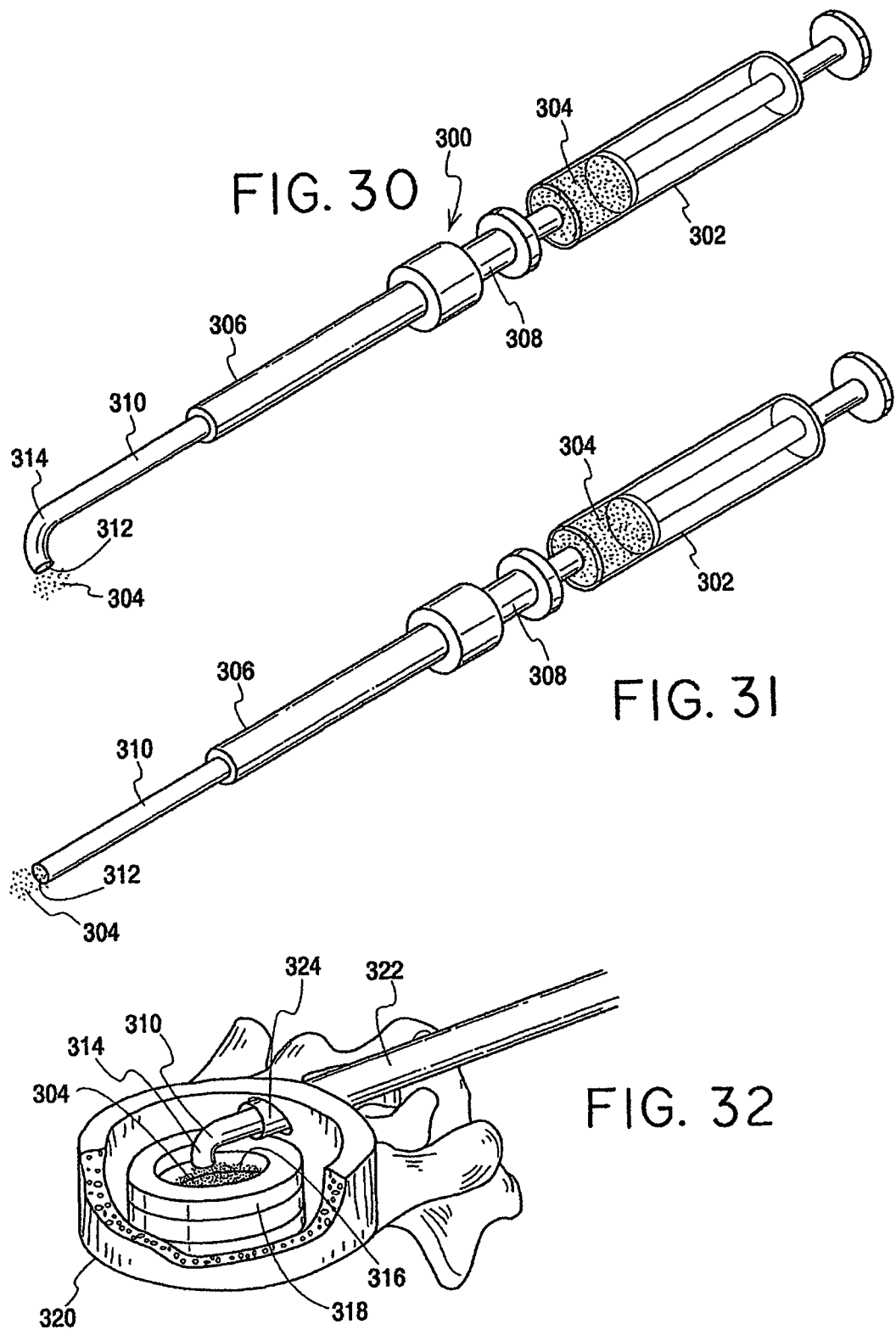

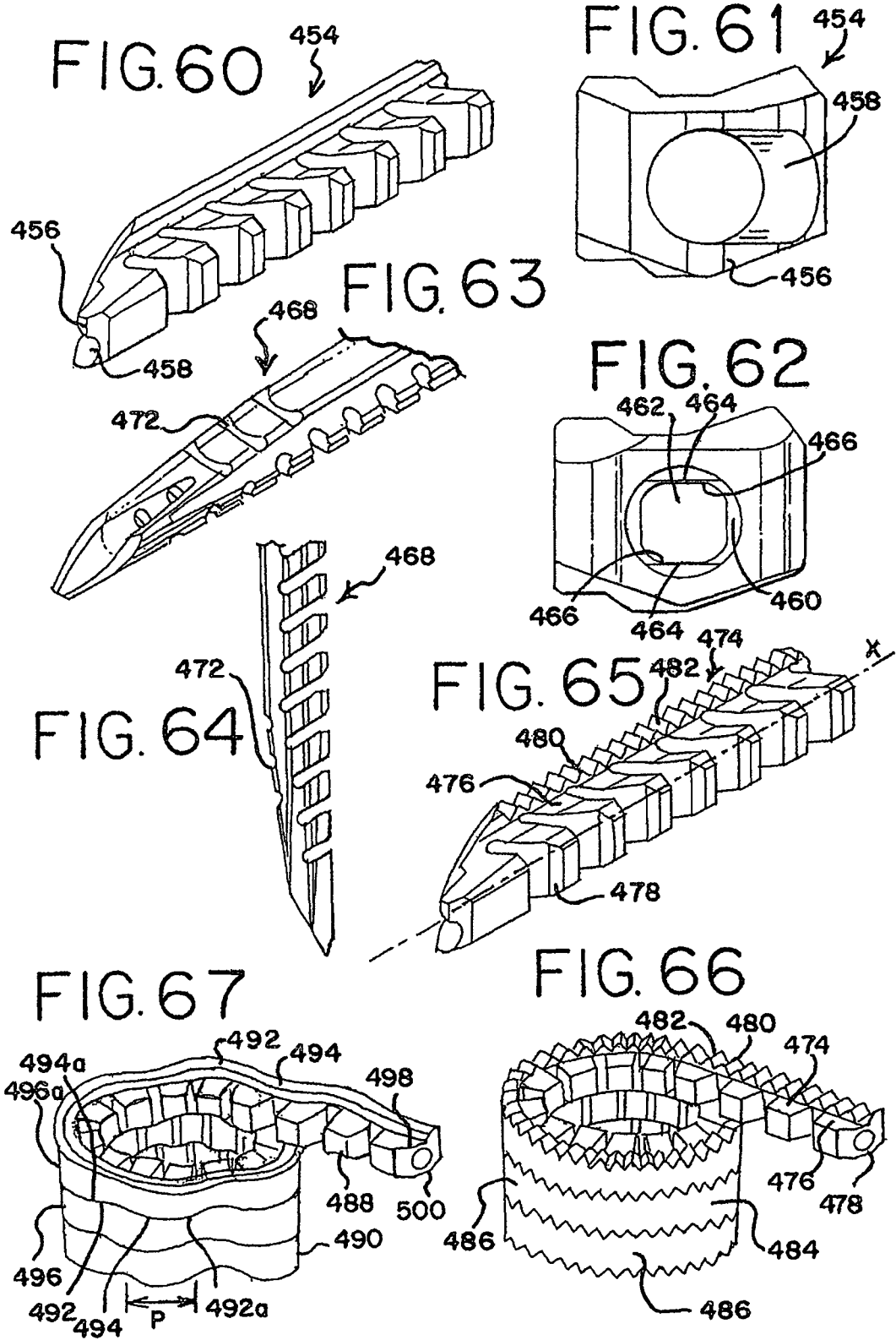

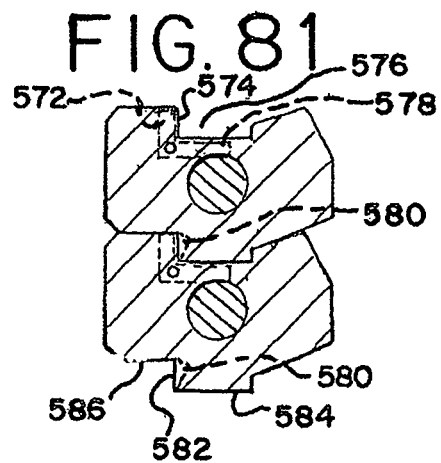
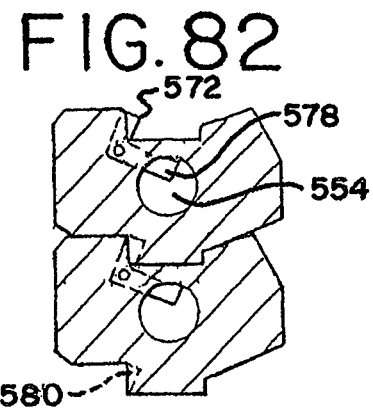
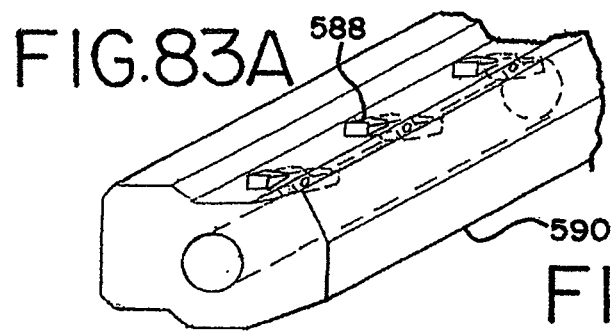
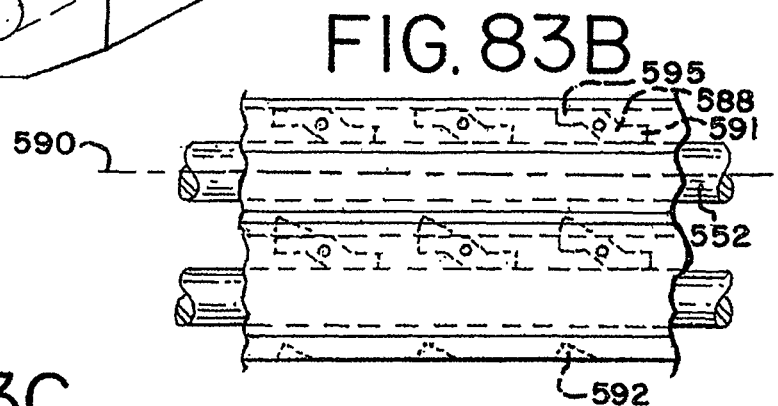
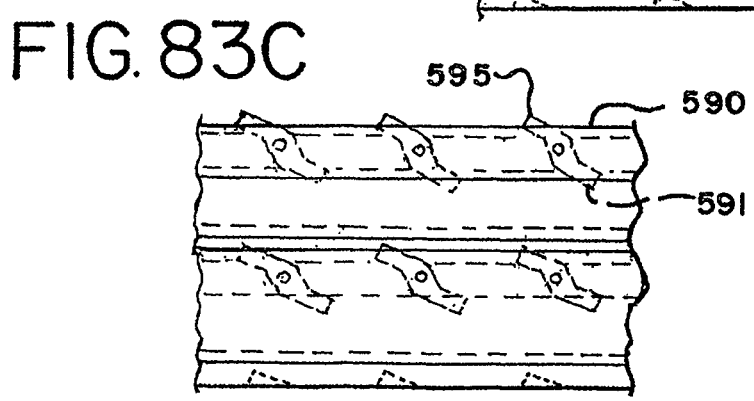

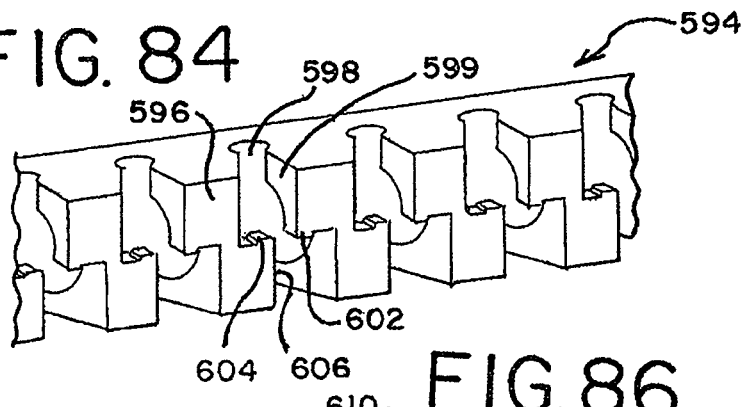
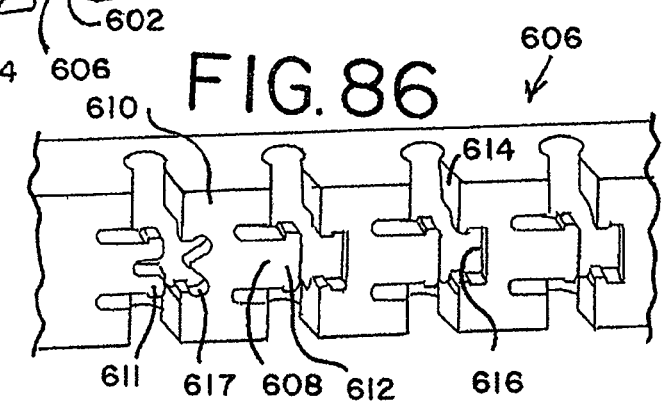
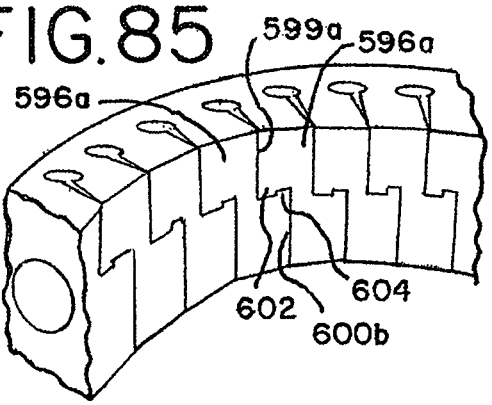
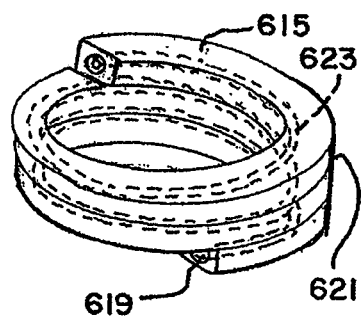
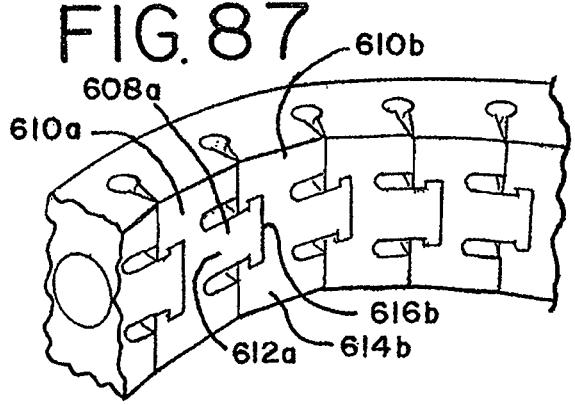

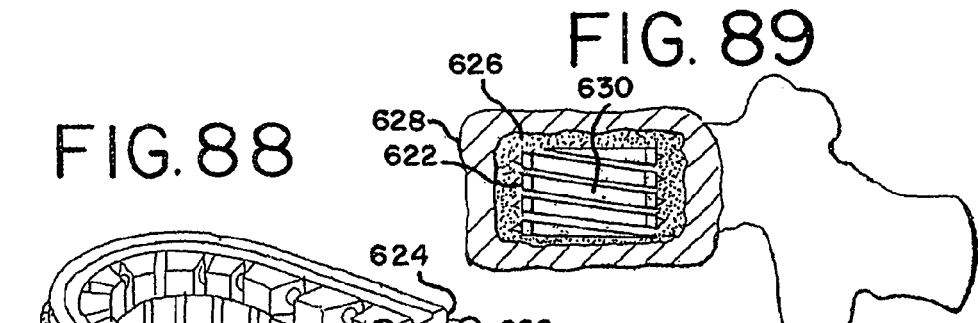
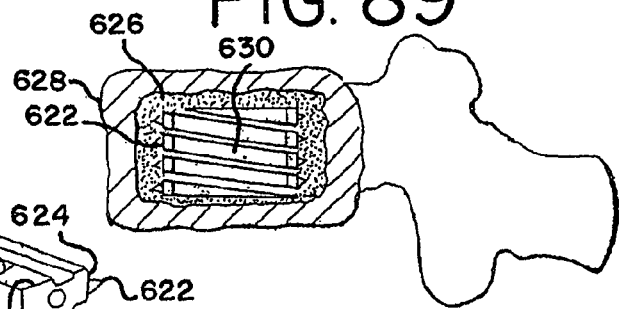
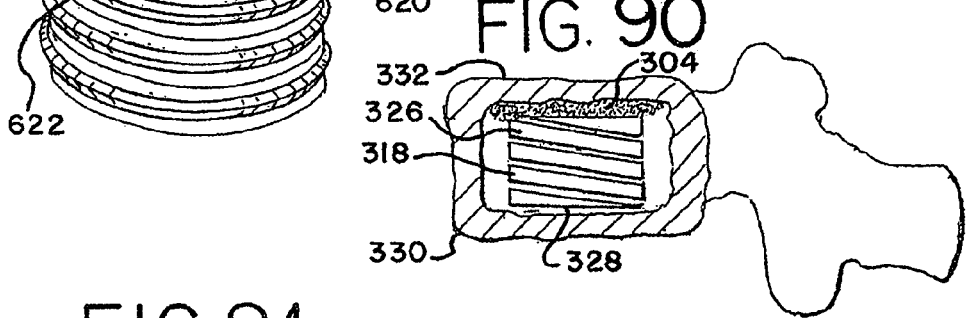
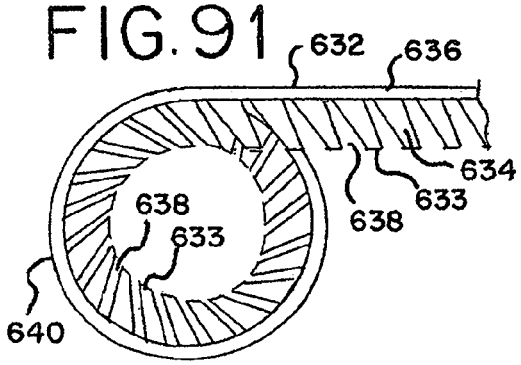
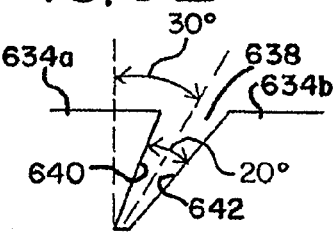
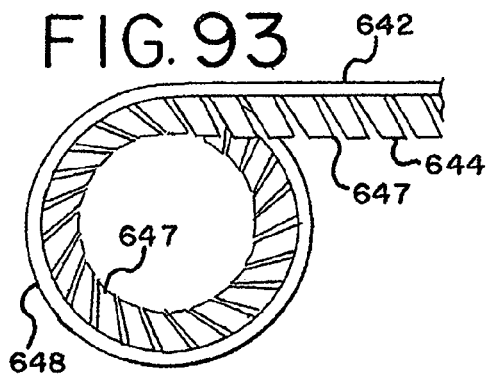
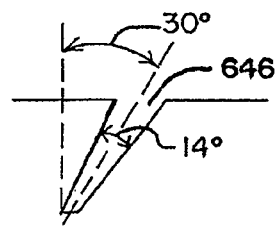

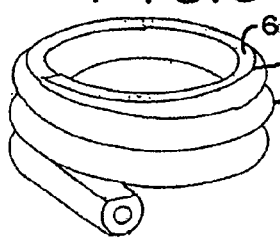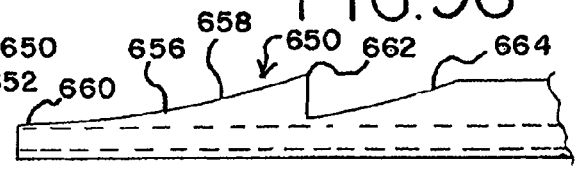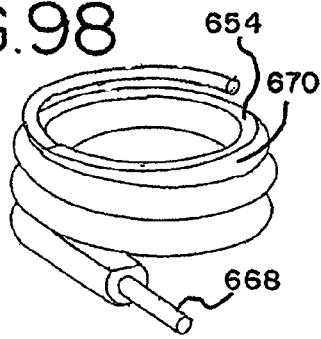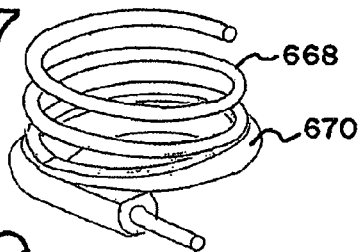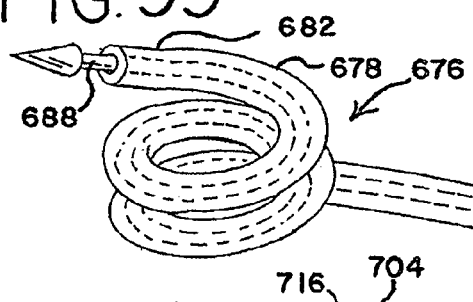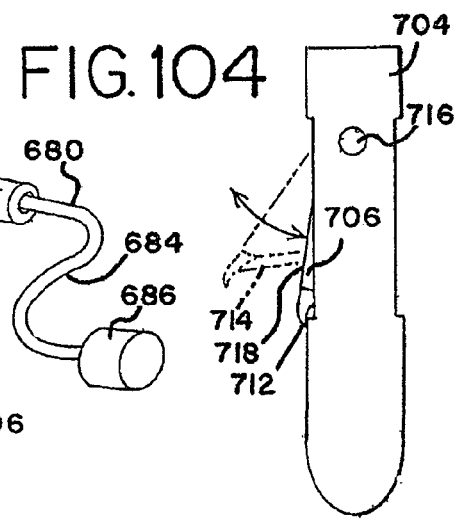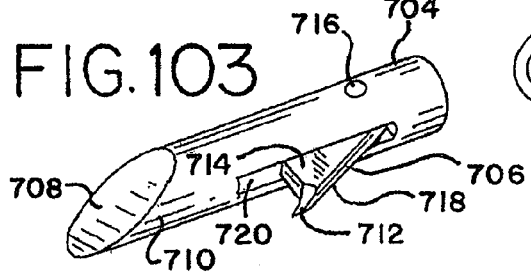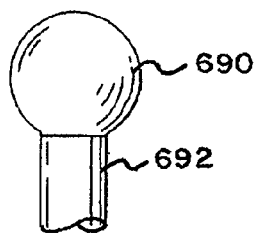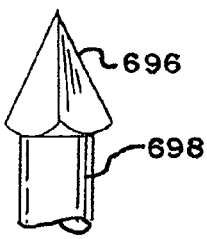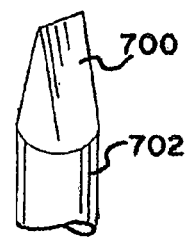

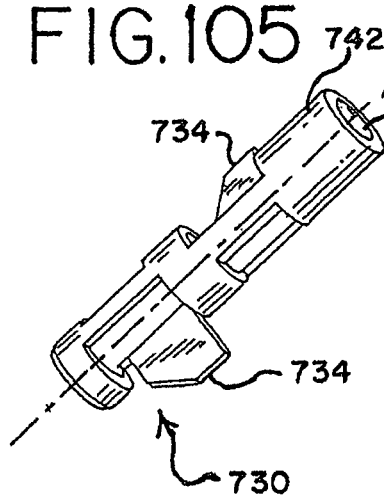
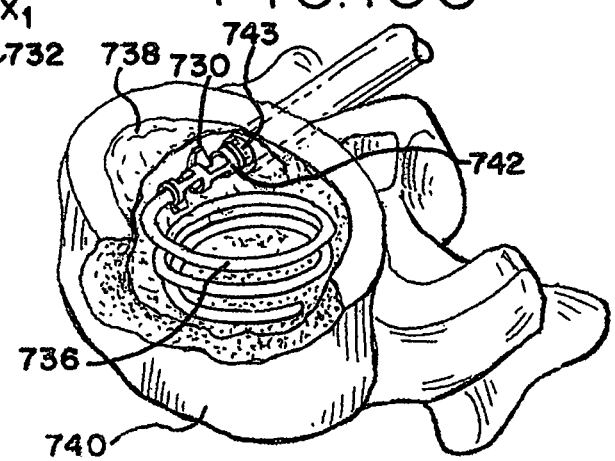
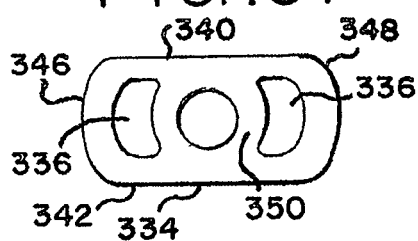
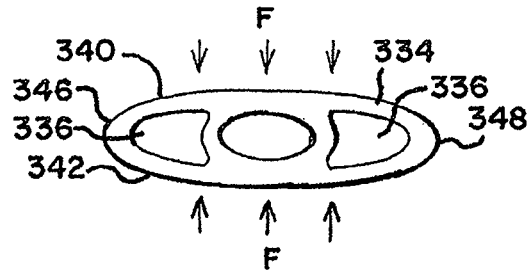
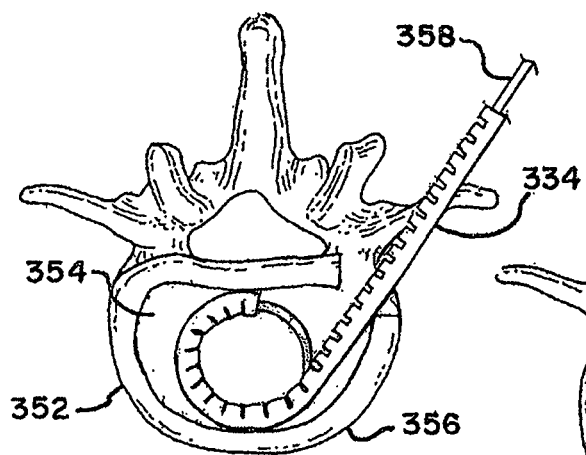
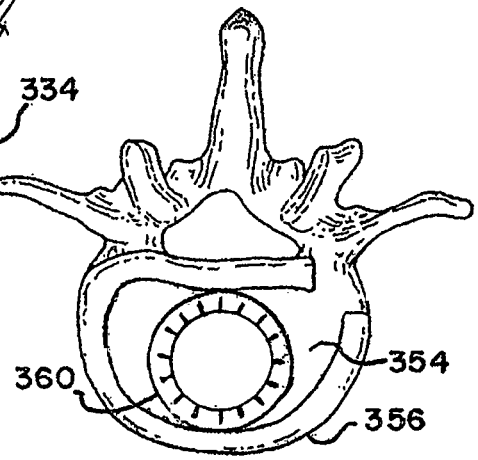

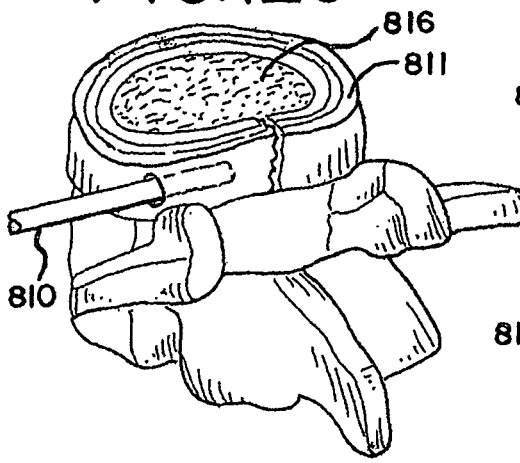
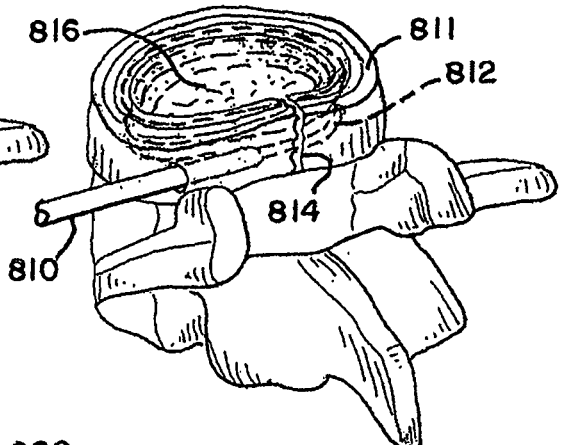
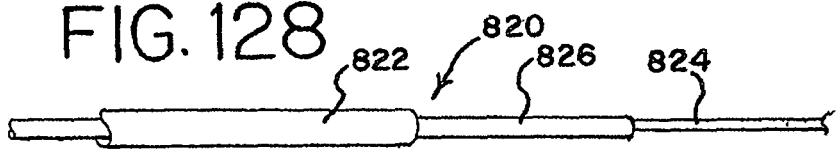
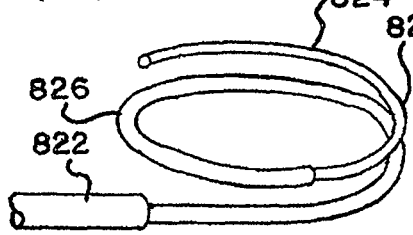
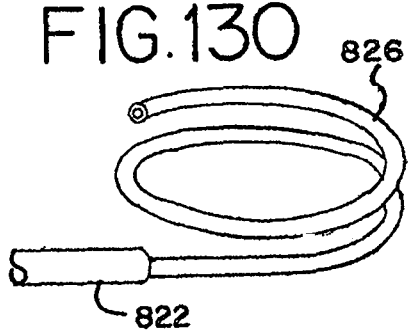
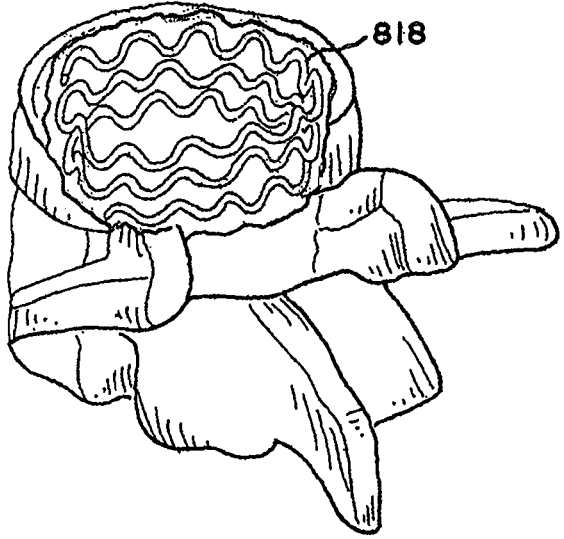

DEVICES FOR TREATING THE SPINE

The present application is a continuation-in-part of U.S. patent application Ser. No. 11/464,782, now U.S. Pat. No. 7,785,368 a continuation-in-part of U.S. patent application Ser. No. 11/464,790, now U.S. Pat. No. 7,666,266 a continuation-in-part of U.S. patent application Ser. No. 11/464,793, now U.S. Pat. No. 7,666,277 a continuation-in-part of U.S. patent application Ser. No. 11/464,807, now U.S. Pat. No. 8,057,544 a continuation-in-part of U.S. patent application Ser. No. 11/464,812, now U.S. Pat. No. 7,670,374 and a continuation-in-part of U.S. patent application Ser. No. 11/464,815, now U.S. Pat. No. 7,670,375 all of which were filed on Aug. 15, 2006, and claim the benefit of U.S. Provisional Application No. 60/708,691, filed Aug. 16, 2005, U.S. Provisional Application No. 60/738,432, filed Nov. 21, 2005 and U.S. Provisional Application No. 60/784,185, filed Mar. 21, 2006, all of the above are incorporated herein by reference. In addition to claiming the benefit of the filing dates of all of the above regular and provisional applications, the present application also claims the benefit of U.S. Provisional Patent Application No. 60/890,868, filed Feb. 21, 2007 and, U.S. Provisional Patent Application No. 60/936,974, filed Jun. 22, 2007, all of which are incorporated herein by reference.

FIELD OF THE INVENTION

The present subject matter generally relates to apparatus and methods employed in minimally invasive surgical procedures and more particularly to various aspects of apparatus and methods for separating and/or supporting tissue layers, especially in the spine.

BACKGROUND OF THE INVENTION

A variety of physical conditions involve two tissue surfaces that, for diagnosis or treatment of the condition, need to be separated or distracted or maintained in a separated condition from one another and then supported in a spaced-apart relationship. Such separation or distraction may be to gain exposure to selected tissue structures, to apply a therapeutic pressure to selected tissues, to return or reposition tissue structures to a more normal or original anatomic position and form, to deliver a drug or growth factor, to alter, influence or deter further growth of select tissues or to carry out other diagnostic or therapeutic procedures. Depending on the condition being treated, the tissue surfaces may be opposed or contiguous and may be bone, skin, soft tissue, or a combination thereof.

One such a condition that occurs in the orthopedic field is vertebral compression fractures. Vertebral compression fractures affect a significant part of the population, and add significant cost to the health care system. A vertebral compression fracture is a crushing or collapsing injury to one or more vertebrae. Vertebral fractures are generally but not exclusively associated with osteoporosis, metastasis, and/or trauma. Osteoporosis reduces bone density, thereby weakening bones and predisposing them to fracture. The osteoporosis-weakened vertebrae can collapse during normal activity and are also more vulnerable to injury from shock or other forces acting on the spine. In severe cases of osteoporosis, actions as simple as bending forward can be enough to cause a vertebral compression fracture. Vertebral compression fractures are the most common type of osteoporotic fractures according to the National Institute of Health.

The mechanism of such vertebral fractures is typically one of flexion with axial compression where even minor events can cause damage to the weakened bone. While the fractures may heal without intervention, the crushed bone may fail to heal adequately. Moreover, if the bones are allowed to heal on their own, the spine may be deformed to the extent the vertebrae were compressed by the fracture. Spinal deformity may lead to breathing and gastrointestinal complications, and adverse loading of adjacent vertebrae.

One technique used to treat vertebral compression fractures is injection of bone filler into the fractured vertebral body. This procedure is commonly referred to as percutaneous vertebroplasty. Vertebroplasty involves injecting bone filler (for example, bone cement, allograph material or autograph material) into the collapsed vertebra to stabilize and strengthen the crushed bone.

In vertebroplasty, physicians typically use one of two surgical approaches to access thoracic and lumbar vertebral bodies: transpedicular or extrapedicular. The transpedicular approach involves the placement of a needle or wire through the pedicle into the vertebral body, and the physician may choose to use either a unilateral access or bilateral transpedicular approach. The extrapedicular technique involves an entry point through the posterolateral corner of the vertebral body.

Regardless of the surgical approach, the physician generally places a small diameter guide wire or needle along the path intended for the bone filler delivery needle. The guide wire is advanced into the vertebral body under fluoroscopic guidance to the delivery point within the vertebra. The access channel into the vertebra may be enlarged to accommodate the delivery tube. In some cases, the delivery tube is placed directly into the vertebral body and forms its own opening. In other cases, an access cannula is placed over the guide wire and advanced into the vertebral body. After placement, the cannula is replaced with the delivery tube, which is passed over the guide wire or pin. In both cases, a hollow needle or similar tube is placed through the delivery tube into the vertebral body and used to deliver the bone filler into the vertebra.

In this procedure, the use of lower viscosity bone filler and higher injection pressures tend to disperse the bone filler throughout the vertebral body. However, such procedures dramatically increase the risk of bone filler extravasation from the vertebral body. The difficulty of controlling or stopping bone filler flow into injury-sensitive areas increases as the required pressure increases. Thus, caution must still be taken to prevent extravasation with the greatest attention given to preventing posterior extravasation because it may cause spinal cord trauma. Physicians typically use repeated fluoroscopic imaging to monitor bone filler propagation and to avoid flow into areas of critical concern. If a foraminal leak results, the patient may require surgical decompression and/or suffer paralysis.

Another type of treatment for vertebral fractures is known as Kyphoplasty. Kyphoplasty is a modified vertebral fracture treatment that uses one or two balloons, similar to angioplasty balloons, to attempt to reduce the fracture and, perhaps, restore some vertebral height prior to injecting the bone filler. One or two balloons are typically introduced into the vertebra via bilateral transpedicular cannula. The balloons are inflated to reduce the fracture. After the balloon(s) are deflated and removed, leaving a relatively empty cavity, bone cement is injected into the vertebra. In theory, inflation of the balloons may restore some vertebral height. However, in practice it is difficult to consistently attain meaningful and predictable height restoration. The inconsistent results may be due, in part, to the manner in which the balloon expands in a compressible media, such as the cancellous tissue within the vertebrae, and the structural orientation of the trabecular bone within the vertebra, although there may be additional factors as well.

Thus there is a need for devices and methods to treat the above mentioned diseases, in particular compression vertebral fractures.

Another location of the body where tissue separation is useful as a corrective treatment is in the spinal column. Developmental irregularities, trauma, tumors, stress and degenerative wear can cause defects in the spinal column for which surgical intervention is necessary. Some of the more common defects of the spinal column include vertebral compression fractures, degeneration or disruption of an intervertebral disk and intervertebral disk herniation. These and other pathologies of the spine are often treated with implants that can restore vertebral column height, immobilize or fuse adjacent vertebral bones, or function to provide flexibility and restore natural movement of the spinal column. Accordingly, different defects in the spinal column require different types of treatment, and the location and anatomy of the spine that requires corrective surgical procedures determines whether an immobilizing implantable device or a flexible implantable device is used for such treatment.

In a typical spinal corrective procedure involving distraction of tissue layers, damaged spinal tissue is removed or relocated prior to distraction. After the damaged tissue has been removed or relocated, adjacent spinal tissue layers, such as adjacent bone structures, are then distracted to separate and restore the proper distance between the adjacent tissue layers. Once the tissue layers have been separated by the proper distance, an immobilizing or flexible device, depending on the desired treatment, is implanted between the tissue layers. In the past, the implantable treatment devices have been relatively large cage-like devices that require invasive surgical techniques which require relative large incisions into the human spine. Such invasive surgical techniques often disrupt and disturb tissue surrounding the surgical site to the detriment of the patient.

Therefore, there remains a need for implantable treatment devices and methods that utilize minimally invasive procedures.

Such methods and devices may be particularly needed in the area of intervertebral or disk treatment. The intervertebral disk is divided into two distinct regions: the nucleus pulposus and the annulus fibrosus. The nucleus lies at the center of the disk and is surrounded and contained by the annulus. The annulus contains collagen fibers that form concentric lamellae that surround the nucleus and insert into the endplates of the adjacent vertebral bodies to form a reinforced structure. Cartilaginous endplates are located at the interface between the disk and the adjacent vertebral bodies.

The intervertebral disk is the largest avascular structure in the body. The cells of the disk receive nutrients and expel waste by diffusion through the adjacent vascularized endplates. The hygroscopic nature of the proteoglycan matrix secreted by cells of the nucleus operates to generate high intra-nuclear pressure. As the water content in the disk increases, the intra-nuclear pressure increases and the nucleus swells to increase the height of the disk. This swelling places the fibers of the annulus in tension. A normal disk has a height of about 10-15 mm.

There are many causes of disruption or degeneration of the intervertebral disk that can be generally categorized as mechanical, genetic and biochemical. Mechanical damage includes herniation in which a portion of the nucleus pulposus projects through a fissure or tear in the annulus fibrosus. Genetic and biochemical causes can result in changes in the extracellular matrix pattern of the disk and a decrease in biosynthesis of extracellular matrix components by the cells of the disk. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disk hydraulic pressure, and ultimately to a loss of disk height. This loss of disk height can cause the annulus to buckle with non-tensile loading and the annular lamellae to delaminate, resulting in annular fissures. Herniation may then occur as rupture leads to protrusion of the nucleus.

Proper disk height is necessary to ensure proper functionality of the intervertebral disk and spinal column. The disk serves several functions, although its primary function is to facilitate mobility of the spine. In addition, the disk provides for load bearing, load transfer and shock absorption between vertebral levels. The weight of the person generates a compressive load on the disks, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disk height can have both local and global effects. On the local (or cellular, level) decreased disk height results in increased pressure in the nucleus, which can lead to a decrease in cell matrix synthesis and an increase in cell necrosis and apoptosis. In addition, increases in intra-discal pressure create an unfavorable environment for fluid transfer into the disk, which can cause a further decrease in disk height.

Decreased disk height also results in significant changes in the global mechanical stability of the spine. With decreasing height of the disk, the facet joints bear increasing loads and may undergo hypertrophy and degeneration, and may even act as a source of pain over time. Increased stiffness of the spinal column and increased range of motion resulting from loss of disk height can lead to further instability of the spine, as well as back pain.

Radicular pain may result from a decrease in foraminal volume caused by decreased disk height. Specifically, as disk height decreases, the volume of the foraminal canal, through which the spinal nerve roots pass, decreases. This decrease may lead to spinal nerve impingement, with associated radiating pain and dysfunction Finally, adjacent segment loading increases as the disk height decreases at a given level. The disks that must bear additional loading are now susceptible to accelerated degeneration and compromise, which may eventually propagate along the destabilized spinal column.

In spite of all of these detriments that accompany decreases in disk height, where the change in disk height is gradual many of the ill effects may be "tolerable" to the spine and patient and may allow time for the spinal system to adapt to the gradual changes. However, the sudden decrease in disk volume caused by herniation which requires surgical removal of the disk or disk nucleus may increase the local and global problems noted above.

Many disk defects are treated through a surgical procedure, such as a discectomy in which the nucleus pulposus material is removed. During a total discectomy, a substantial amount (and usually all) of the volume of the nucleus pulposus is removed and immediate loss of disk height and volume can result. Even with a partial discectomy, loss of disk height can ensue. Discectomy alone is the most common spinal surgical treatment, frequently used to treat radicular pain resulting from nerve impingement by disk bulge or disk fragments contacting the spinal neural structures.

The discectomy may be followed by an implant procedure in which a prosthesis is introduced into the cavity left in the disk space when the nucleus material is removed. Thus far, the most common prosthesis is a mechanical device or a "cage" that is sized to restore the proper disk height and is configured for fixation between adjacent vertebrae. These mechanical solutions take on a variety of forms, including solid kidney-shaped implants, hollow blocks filled with bone growth material, push-in implants and threaded cylindrical cages.

A challenge in the use of a posterior procedure to install spinal prosthesis devices is that a device large enough to contact the end plates and expand the space between the end plates of the same or adjacent vertebra must be inserted through a limited space. In the case of procedures to increasing intervertebral spacing, the difficulties are further increased by the presence of posterior osteophytes, which may cause "fish mouthing" or concavity of the posterior end plates and result in very limited access to the disk. A further challenge in degenerative disk spaces is the tendency of the disk space to assume a lenticular shape, which requires a relatively larger implant than often is difficult to introduce without causing trauma to the nerve roots. The size of rigid devices that may safely be introduced into the disk space is thereby limited.

While cages of the prior art have been generally successful in promoting fusion and approximating proper disk height, typically these cages have been inserted from the posterior approach, and are therefore limited in size by the interval between the nerve roots. Further, it is generally difficult, if not impossible to implant from the posterior approach a cage that accounts for the natural lordotic curve of the lumber spine.

It is desirable to reduce potential trauma to the nerve roots and yet still allow restoration or maintenance of disk space height in procedures involving vertebrae fusion devices and disk replacement, containment of the nucleus of the disk or prevention of herniation of the nucleus of the disk. In general minimally invasive surgical techniques reduce surgical trauma, blood loss and pain. However, despite the use of minimally invasive techniques, the implantation of cage devices for treating the spine typically involves nerve root retraction, an inherently high risk procedure. It is therefore desirable to reduce the degree of invasiveness of the surgical procedures required to implant the device, which may also serve to permit reduction in the pain, trauma, and blood loss as well as the avoidance and/or reduction of the nerve root retraction.

In minimally invasive procedures, to monitor placement, it is useful that implant devices inserted into spinal tissue be detectable using fluoroscopic imaging systems. However if a device is visible using X-ray technology, then the device can interfere with the detection and monitoring of spinal tissues, such as bone growing into the disk space after a vertebral fusion procedure. Additional advances would also be useful in this area.

SUMMARY OF INVENTION

The present invention relates to various aspects of distraction systems and methods for separating, supporting or both separating and supporting tissue layers in the human body.

One aspect of the present disclosure relates to a spinal implant including a generally elongated member having a first configuration for insertion between spinal tissue layers and a second configuration in-situ in which the elongated member curves to form a distraction structure that engages and distracts spinal tissue. The elongated member has a first extent in a direction extending between the spinal tissue layers and the distraction structure has a second extent in the direction extending between the tissue layers. The second extent of the distraction structure is greater than the first extent of the elongated member.

Another aspect of the present disclosure relates to a spinal implant system including a guide member adapted for insertion into spinal tissue and a generally elongated member advanceable along the guide member. The guide member is adapted for guiding the elongated member to a location between spinal tissue layers and into a shape in-situ of a support structure that separates, supports or both separates and supports the spinal tissue layers.

Yet another aspect of the present disclosure relates to a spinal implant deployment system including a first cannula having a proximal end portion, a distal end portion and a passageway therethrough. The distal end portion of the first cannula includes an opening in communication with the passageway and is adapted for insertion into or between spinal tissue layers. The deployment system also includes a guide member that has a distal end portion that is advanceable through the passageway and the opening of the first cannula for deployment into or between spinal tissue layers. Additionally, the deployment system includes an elongated member adapted for advancement along the guide member and through the passageway and the opening of the first cannula for deployment into or between tissue layers. The elongated member is guided by the guide member to form a support structure in-situ wherein the support structure separates, supports (or both) and spinal tissue layers.

Yet a further aspect of the present invention relates to a spinal implant comprising an implantable member that is adapted for implantation into or between spinal tissues. The implantable member is comprised of a thermoplastic material and is substantially incompressible in a first direction and substantially flexible in a second direction that is generally perpendicular to the first direction.

Another aspect of the present disclosure relates to a device for treating an intervertebral disk comprising a guide member that is insertable into the intervertebral disk, preferably between the annulus and nucleus of the disk. The guide member has a pre-deployed configuration for insertion into the disk and a deployed configuration in which the guide member at least partially surrounds at least a portion of the nucleus. The device also includes at least one elongated member advanceable along the guide member and positionable within the disk.

Yet another aspect of the present disclosure relates to a device for treating an intervertebral disk comprising an elongated member that is insertable into an intervertebral disk, preferably between the annulus and nucleus of the disk. The elongated member has a pre-deployed configuration for insertion into the disk and a deployed configuration in which the elongated member forms a structure that at least partially surrounds the nucleus. The structure is adapted to substantially contain the nucleus within the annulus.

Yet a further aspect of the present disclosure is related to a device for treating an annulus of an intervertebral disk comprising an elongated member that is insertable into the annulus of an intervertebral disk. The elongated member has a pre-deployed configuration for insertion into the annulus and a deployed configuration in which the elongated member forms a support structure that supports the annulus.

Yet another aspect of the present invention relates to a device for delivering flowable material into spinal tissue. The device includes a delivery tube that has a proximal end portion and a distal end portion. The proximal end portion is adapted to be operatively connected to a supply of flowable material. The distal end portion of the delivery tube has a first linear pre-delivery configuration for insertion into spinal tissue and a second curved delivery configuration within the spinal tissue for the directional delivery of flowable material.

Yet a further aspect of the present disclosure relates to a method of treating the human spine comprising inserting at least the distal end portion of a guide member between tissue layers of the human spine. The configuration of the distal portion of the guide member is then changed in-situ to define a predetermined shape. An elongated member is then advanced over at least the distal end portion of the guide member so that the elongated member substantially assumes the predetermined shape of the distal end portion of the guide member to form a support structure between the tissue layers.

A further aspect of the present disclosure relates to a method of treating an intervertebral disk comprising inserting a distal end portion of a guide member into the intervertebral disk, preferably between an annulus and nucleus of the disk. The shape of the distal end portion of the guide member is then changed in-situ. A first generally elongated member is advanced over the distal end portion of guide member to a location within the disk and the first generally elongated member defines a containment structure that assists in substantially containing the nucleus within the annulus.

Another aspect of the present disclosure relates to a method of treating an intervertebral disk comprising inserting a generally elongated member into an intervertebral disk, preferably between the annulus and the nucleus of the disk. The configuration of the elongated member is then changed in-situ to define a structure that assists in substantially containing the nucleus within the annulus.

A further aspect of the present disclosure relates to a method of repairing an annulus of an intervertebral disk comprising inserting a generally elongated member into an annulus of an intervertebral disk. The configuration of the elongated member is then changed in-situ to define a coil-like structure that assists in substantially containing the nucleus within the annulus.

BRIEF DESCRIPTION OF THE FIGURES

In the course of this description, reference will be made to the accompanying drawings, wherein:

FIGS. 9-19 are perspective views of different embodiments of distraction devices and support structures formed therefrom, showing a variety of shapes and cross-sectional profiles;

FIG. 20 is a perspective view of a vertebra with the superior endplate removed to show the delivery of a guide member into the vertebral body;

FIG. 21 is a perspective view of the vertebra of FIG. 20 shown with a distraction device and pusher mounted on the guide member;

FIG. 22 is a perspective view of the vertebra of FIG. 20 shown with the distraction device partially advanced or deployed within the vertebral body;

FIG. 23 is a perspective view of the vertebra of FIG. 20 shown with the distraction device substantially fully deployed within the vertebral body;

FIG. 24 is a side cross-sectional view of the vertebra of FIG. 20, with the distraction device fully deployed within the vertebral body;

FIGS. 25-29 illustrate a method of incremental deployment of the distraction device;

FIG. 30 is a perspective view of one embodiment of a flowable material delivery device in a first configuration;

FIG. 31 is a perspective view of the flowable material delivery device of FIG. 30 in a second configuration;

FIG. 32 is a perspective view of vertebra having flowable material delivered therein;

FIGS. 43-64 are various illustrations of different embodiments of the distal end portion of a distraction device;

FIG. 65 is a perspective view of another embodiment of a distraction device;

FIG. 66 is a perspective view of a distraction device support structure that is defined by the distraction device of FIG. 65;

FIG. 67 is a perspective view of another embodiment of a distraction device and distraction device support structure;

FIG. 81 is a cross-sectional view of a support structure defined by another embodiment of a distraction device;

FIG. 82 is a cross-sectional view of the support structure of FIG. 81;

FIG. 83A is a perspective view of another embodiment of a distraction device;

FIG. 83B is a side view of the support structure defined by the distraction device of FIG. 83A;

FIG. 83C is a side view of the support structure of FIG. 83B;

FIG. 84 is a perspective view of another embodiment of a distraction device, shown with the teeth in an unlocked position;

FIG. 85 is a perspective view of the distraction device of FIG. 84, shown with the teeth in a locked position;

FIG. 86 is a perspective view of another embodiment of a distraction device, shown with the teeth in an unlocked position;

FIG. 87 is a perspective view of the distraction device of FIG. 86, shown with the teeth in a locked position;

FIG. 87A is a perspective view of another embodiment of a distraction device that includes a reinforcing member that assists in maintaining the distraction device in the shape of the support structure;

FIG. 88 is a perspective view of another embodiment of a distraction device and distraction device support structure;

FIG. 89 is a cross-sectional view of a vertebra shown with the distraction device of FIG. 88 defining a support structure therein;

FIG. 90 is a cross-sectional view of a vertebra shown with a distraction device support structure deployed therein and flowable material located on the superior side of the distraction device support structure;

FIG. 91 is a top view of another embodiment of a distraction device and distraction device support structure;

FIG. 92 is a schematic illustration of the relationship between the teeth of the distraction device of FIG. 91;

FIG. 93 is a top view of another embodiment of a distraction device and distraction device support structure;

FIG. 94 is a schematic illustration of the relationship between the teeth of the distraction device of FIG. 93;

FIG. 95 is a perspective view of another embodiment of a distraction device defining a distraction device support structure;

FIG. 96 is a side view of the distal end portion of the distraction device of FIG. 95;

FIG. 97 is a perspective view of the distraction device of FIG. 96, shown initially deployed over a guide member to form the distraction device support structure of FIG. 95;

FIG. 98 is a perspective view of the distraction device of FIG. 96, shown further deployed over the guide member to form the distraction device support structure of FIG. 95;

FIG. 99 is a perspective view of one embodiment of a guide member;

FIGS. 100-104 illustrate different embodiments of the distal end portion of the guide member;

FIG. 105 is a perspective view one embodiment of a cutting member which can be advanced along a guide member;

FIG. 106 is perspective view of a vertebra having the cutting member of FIG. 105 deployed therein;

FIG. 107 is a cross-sectional view of another embodiment of a distraction device;

FIG. 108 is a cross-sectional view of the distraction device of FIG. 107, shown in a compressed configuration;

FIG. 109 is a top cross-sectional view of the intervertebral disk, shown with a distraction device partially advanced over the guide member within the nucleus space;

FIG. 110 is a top cross-sectional view of the intervertebral disk of FIG. 109, shown with the distraction device defining a support structure within the nucleus space;

FIG. 126 is a perspective view of an intervertebral disk, shown with a deployment cannula deployed therein;

FIG. 127 is a perspective view of the intervertebral disk of FIG. 126, shown with an annulus repair device deployed within the annulus;

FIG. 128 is a perspective view of one embodiment of an annulus repair deployment system;

FIG. 129 is a perspective view of the deployments system of FIG. 128, shown in a coiled configuration;

FIG. 130 is a perspective view of the deployment system of FIG. 128, shown in coiled configuration;

FIG. 131 is a side view of another embodiment of the nucleus containment device; and FIG. 132 is a perspective view of the nucleus containment device of FIG. 131 deployed within an intervertebral disk.

DETAILED DESCRIPTION

The devices and methods of the present invention provide multiple features of spinal implants, such as distraction devices, distraction device support structures and deployment systems that can be used to actively separate tissue layers by engaging them and forcing them apart, or to support the separation of tissue layers separated by the distraction device itself or by other devices or processes or a combination of these.

As used herein, the terms "distraction device" and "distraction device support structure" are intended to have a general meaning and are not limited to devices that only actively separate tissue layers, only support tissue layers or only both actively separate and support tissue layers. For example, the distraction device and support structure in general can be used to actively separate layers of tissue and then be removed after such separation, or the distraction device and the support structure could be used to support layers of tissue that have been previously separated by a different device. Alternatively, the distraction device and support structure can be used to actively separate the layers of tissue and remain in place to support the layers of tissue in order to maintain such separation. Unless more specifically set forth in the claims, as used herein, "distraction device" and "distraction device support structure" encompasses any and all of these.

It should also be understood that various embodiments of the device, system and method of the present subject matter are illustrated for purposes of explanation in the treatment of vertebral compression fractures, height restoration of a diseased disk, vertebral fusion procedures, replacement of removed disks or vertebra, intervertebral disk nucleus containment or annulus fibrous repair. However, in its broader aspects, the various features of the present invention are not limited to these particular applications and may be used in connection with other tissue layers, such as soft tissue layers, although it has particular utility and benefit in treatment of vertebral conditions.

Figure 1:
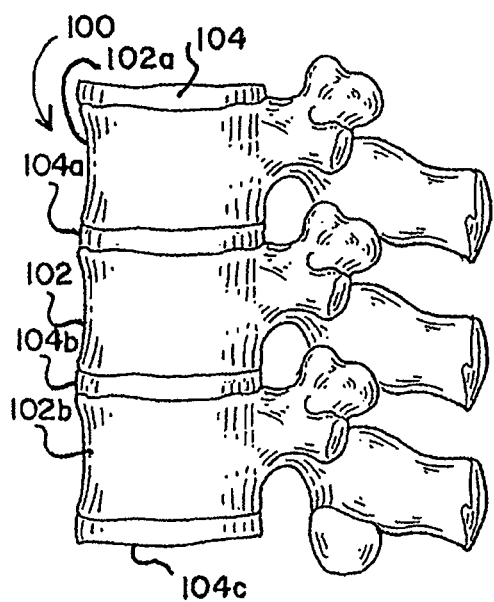
FIG. 1 is a partial side view of a normal human vertebral column.

FIG. 1 illustrates a section of a healthy vertebral (spinal) column, generally designated as 100, without injury. The vertebral column 100 includes adjacent vertebrae 102, 102a and 102b and intervertebral disks 104, 104a, 104b and 104c separating the adjacent vertebrae.

Figure 3:
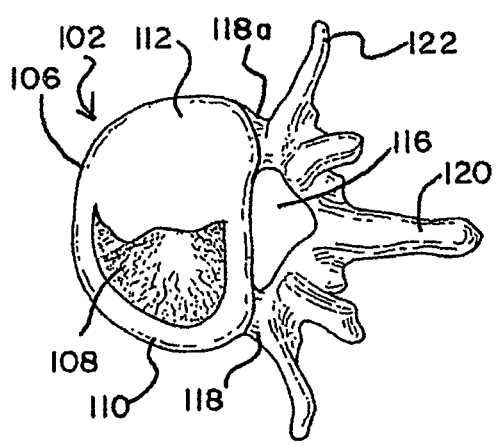
FIG. 3 is a top view of a vertebra with an endplate partially removed.
Figure 4:
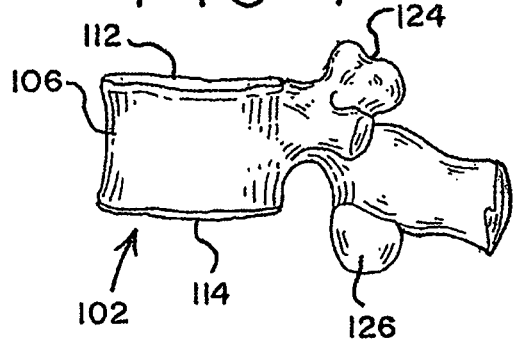
FIG. 4 is a side view of the vertebra of FIG. 3.

FIGS. 3 and 4 illustrate in more detail a normal vertebra and its attributes. The vertebra, generally designated as 102, includes a vertebral body 106 that is roughly cylindrically and comprised of inner cancellous bone 108 surrounded by the cortical rim 110, which is comprised of a thin layer of cortical compact bone. The cortical rim 110 can be weakened by osteoporosis and may be fractured due to excessive movement and/or loading. The body 106 of the vertebra is capped at the top by a superior endplate 112 and at the bottom by an inferior endplate 114, made of a cartilaginous layer. To the posterior (or rear) of the vertebral body 106 is the vertebral foramen 116, which contains the spinal cord (not shown). On either side of the vertebral foramen 116 are the pedicles 118, 118a, which lead to the spinal process 120. Other elements of the vertebra include the transverse process 122, the superior articular process 124 and the inferior articular process 126.

Figure 2:
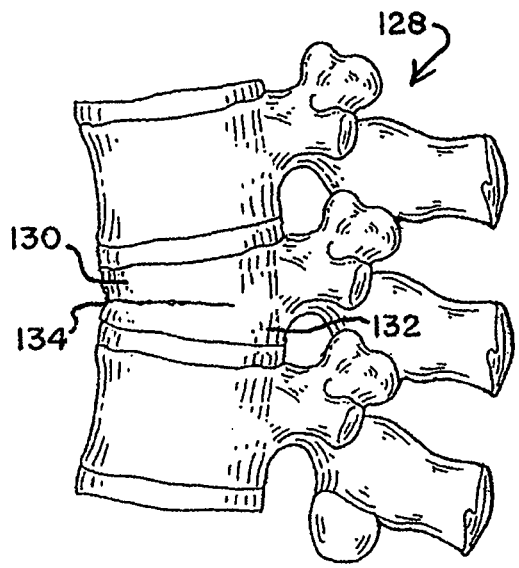
FIG. 2 is comparable to FIG. 1, but shows a vertebral compression fracture in one of the vertebral bodies.

FIG. 2 illustrates a damaged vertebral column, generally designated as 128, with a vertebral body 130 of a vertebra 132 suffering from a compression fracture 134. The vertebral body 130 suffering from the compression fraction 134 becomes typically wedge shaped and reduces the height of both the vertebra 132 and vertebral column 128 on the anterior (or front) side. As a result, this reduction of height can affect the normal curvature of the vertebral column 128.

Figure 5:
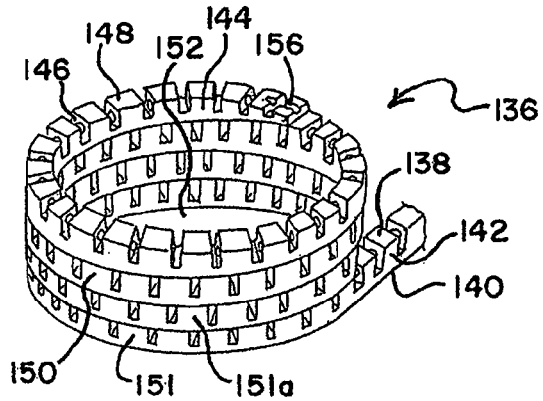
FIG. 5 is a perspective view of one embodiment of a distraction device support structure defined by an elongated member that has a coil-like or a spring configuration.

FIG. 5 illustrates one embodiment of a spinal implant or distraction device 136 in accordance with the present subject matter. In this embodiment, the distraction device 136 is comprised of an elongated member, such as a thread or ribbon, made from biocompatible materials that are suitable for long term implantation into human tissue in the treatment of degenerative tissue, trauma or metastatic conditions or where a tissue distraction device is needed. The biocompatible materials may be calcium phosphate, tricalcium phosphate, hydroxyapatite, polyetheretherketones (PEEK), nylon, Nitinol (NiTi) or any other suitable biocompatible material. The material may be solid or porous for tissue ingrowth, and may elute therapeutic or growth enhancing agents. One of the advantages of using biological or biocompatible material to treat vertebral compression fractures is that these elements have a more natural like substance. However, other materials could be used and still be within the scope of the present invention.

Figure 6:
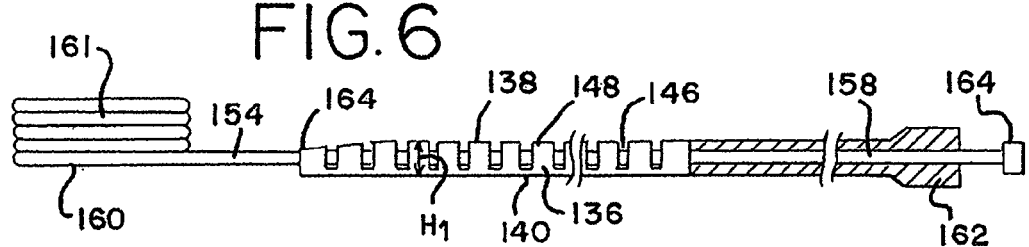
FIG. 6 is a partial cross-sectional side view one embodiment of a delivery system for deploying the distraction device of FIG. 5.

Referring to FIGS. 5 and 6, distraction device 136 or spinal implant has a generally rectangular cross-section defined by a top surface 138, a bottom surface 140 and first and second sidewalls 142 and 144. However, as described in more detail below, the distraction device can have a variety of shapes and profiles. Distraction device 136 also includes a plurality of alternating recesses or slots 146 and projections or teeth 148 spaced along the length of the distraction device. Furthermore, distraction device 136 is substantially rigid or incompressible in a first dimension or direction between the top surface 138 and bottom surface 140, and substantially flexible in a second dimension or direction that is generally perpendicular to the first dimension and extends along the length of the distraction device. As explained in more detail below, recesses 146 can facilitate flexibility of distraction device 136 in the second dimension.

When deployed between tissue layers, distraction device 136 curves or flexes to define a structure 150, such as a support structure, that has a multi-tiered arrangement, such as a scaffolding or platform, that serves to actively separate or support (or both) opposed tissue layers as shown in FIGS. 5, 8, 23 and 24. Referring to FIG. 5, distraction device 136, as deployed, has a helical, coil or spring-like configuration. As illustrated, the distraction device defines a helical configuration with a tight pitch forming an essentially hollow cylinder or cage. Each turn or winding 151 is wound on top of the pervious winding 151a to form a plurality of stacked windings or tiers in which top surface 138 and bottom surface 140 of distraction device 136 are in contact or have little or no spacing therebetween. Because distraction device 136 is substantially rigid in the first dimension between top and bottom surfaces 138, 140, in this deployed configuration, the distraction device forms a very stiff column or structure 150 along the axis of a center line of the coil or spring-like structure.

In one embodiment, structure 150 includes or defines an innerspace or resident volume 152. As used herein, "resident volume" refers generally to a structural characteristic of the support structure. The resident volume is a volume that is generally defined by the distraction device, when it is in the deployed configuration. The resident volume is not necessarily a volume completely enclosed by the distraction device and can be any volume generally defined by the distraction device. This term does not necessarily mean that the resident volume is an open or void volume or cavity and does not preclude a situation in which the resident volume is, at some point in time, filled with another material, such as bone filler, cement, therapeutic drugs or the like. It also does not preclude the resident volume from containing undisturbed human tissue that is located or remains within the resident volume during or after deployment of the distraction device, as will be explained in more detail below. For example, if the distraction device is employed to separate adjoining soft tissue layers, such as subcutaneous fat and underlying muscle tissue, the resident volume of the distraction device may be hollow or void of tissue after separation. On the other hand, if inserted into a vertebra having cancellous bone tissue therein, the resident volume will contain undisturbed bone tissue and no void or cavity is formed by the distraction device.

When distraction device 136 is comprised of a substantially rigid thermoplastic material, such as PEEK, the distraction device can be manufactured by machining a solid block or sheet of thermoplastic material to form the desired shape of the distraction device or elongated member. In other embodiments, the distraction device can be extruded or injection molded. After the distraction device has been formed from the thermoplastic material, the distraction device can be formed into and constrained in its deployed configuration and heat treated. The heat treatment reduces material stress caused by curving or flexing the distraction device into the deployed configuration. Such stress reduction reduces the potential risk of fractures or micro-cracks that may occur in the material of the distraction device as a result of flexing the distraction device. In one embodiment, for example, the distraction device is heat treated at 160° C. for a period of five minutes.

FIG. 6 illustrates distraction device 136 and one embodiment of a delivery system. In this embodiment, distraction device 136 is used in conjunction with a guide member 154, such as a guide wire or delivery track. Distraction device 136 includes a center bore or passageway 156 (shown in FIG. 5) that accepts guide member 154 for slidably mounting the distraction device onto the guide member. Prior to deployment, distraction device 136 preferably has a first generally linear pre-deployed configuration, as illustrated in FIG. 6.

Distraction device 136 should have sufficient flexibility to follow along the contour of the guide member 154. For example, distraction device 136 may be required to take on a generally linear shape for mounting guiding member for deployment into the treatment site and then may be required to flex or curve to form a generally coil or spring shape within the treatment site.

The guide wire 154 includes a proximal end portion 158 and a distal end portion 160. Distal end portion 160, in a deployed state, preferably defines a multi-tiered arrangement, scaffolding or platform, such as the illustrated coil or helical shape with a plurality of stacked windings 161, as shown in FIG. 6. The shape of distal end portion 160 of the guide member 154 in a deployed state may be predetermined. In one embodiment, at least the coil shaped distal end portion 160 of the guide member 154 is made of a shape memory material, such as a Nitinol or a polymer having shape memory characteristics, so that the guide member can be deformed into a generally straight configuration prior to or during deployment of the guide member into the treatment site, and then allowed to reform into its initial coil shape within the treatment site. With this arrangement, the guide member itself may act as an initial distraction device, contacting the endplates of the vertebra and forcing them apart. For that purpose, the guide member may also have a cross-sectional shape (e.g., oval) that tends to reduce contact force with endplates or to keep contact force within an acceptable range.

After the coiled distal end portion 160 of the guide wire has attained the desired positioned within the treatment site, distraction device 136 is advanced along guide member 154 by a pusher 162. As explained in more detail below, distal end portion 164 of distraction device 136 can be tapered, ramped or otherwise configured to facilitate insertion and passage of the distraction device through the bone and between the tissue layers to be distracted.

Figure 7:
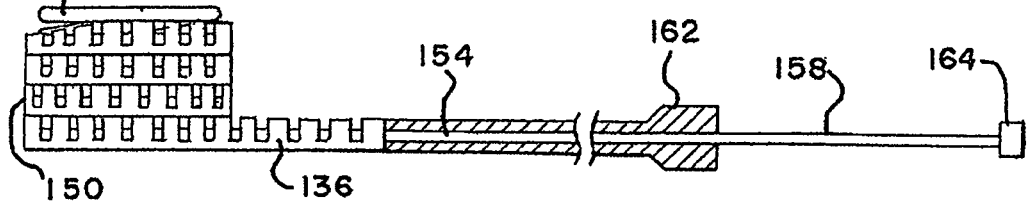
FIG. 7 is a partial cross-sectional side view of the distraction device delivery system of FIG. 6, shown with the distraction device partially advanced over a coiled section of a guide member.

A small knob 164 can be mounted at the proximal end portion 158 of the guide member 154 to provide a gripping portion. Knob 164 can be held in place as pusher 162 is advanced distally along the guide member 154, indicated by arrow D in FIG. 7. Optionally, the pusher can be advanced by a drive mechanism. Advancing the pusher 162 distally forces distraction device 136 to advance distally over the guide member 154. Distraction device 136 follows along guide member 154 into between tissue layers and substantially takes the shape of coiled distal end portion 160 of guide member 154 to form structure 150 having a multi-tiered arrangement or scaffolding. For example, in the illustrated embodiment, distraction device 136 winds into a coil shape as it passes over the coil-shaped distal end portion 160 of the guide member 154. Distraction device 136 winds upon on itself as many times as the number of windings 161 of the guide member to form a multi-tiered support structure or scaffolding, such as the coil or helical shaped structure 150.

Figure 8:
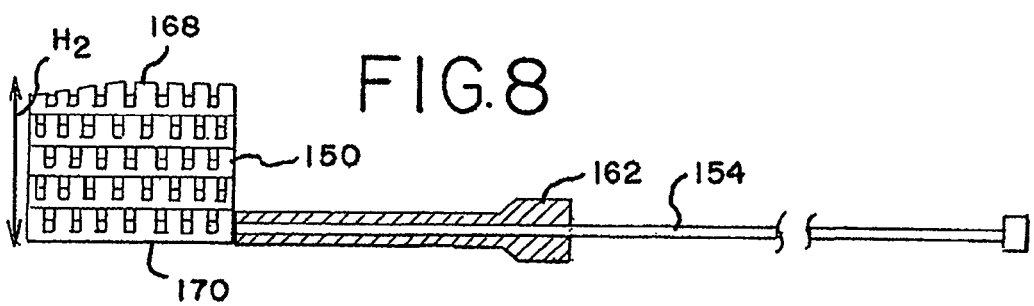
FIG. 8 is a partial cross-sectional side view of the distraction device delivery system of FIG. 6, shown with the distraction device substantially advanced over the coiled section of the guide member.

FIG. 8 illustrates a completed scaffolding or support structure 150 that is defined by the coiled distraction device 136. The height or extend of structure 150 is largely dependent on the height or extend of distraction device 136. Top surface 138 and bottom surface 140 of distraction device 136 are separated by a first dimension or distance $H_1$ (shown in FIG. 6), which defines the height or extend of the distraction device. Structure 150 has a top surface 168 and a bottom surface 170. Top surface 168 and bottom surface 170 are separated by a second dimension or distance $H_2$ (shown in FIG. 8), which defines the height or extent of structure 150. The distance $H_1$ of distraction device 136 is less than the distance $H_2$ Of the structure 150, and the height of structure 150 is determined generally by multiplying the number of turns or windings by the height $H_1$ of the elongated distraction device. After structure 150 has been formed, if desired, the guide member 154 can be removed from the deployed distraction device 136. The removal of the guide member 154 can be accomplished by holding the pusher 162 in place while pulling the proximal end 158 of the guide member 154 in a proximal direction. Optionally, depending on the treatment, the guide member 154 can remain in place with the distraction device 136 to further strengthen and stabilize the support structure 150. In such usage, the proximal end 158 of the guide member 154 could be severed from the remainder of the guide member by cutting, unscrewing or other means as it is known in the art.

It should therefore be apparent from the above that the present invention is particularly advantageous and conducive to minimally invasive surgical procedures for treatment of the spine. In accordance with this aspect of the present invention only a single access opening is required, which may be made transcutaneously and through the appropriate spinal bone or other tissue. Through this single opening a relatively large three-dimensional support structure can be built within the confined space of an individual vertebra or between adjoining vertebrae. Insertion of the distraction device may be aided by an introduction cannula or sheath, or the distraction device itself may be directly advanced through an access opening without the need for a cannula or other advancing aid. In any event, in the illustrated embodiment a relatively large support structure is built or formed in situ through a relatively much smaller access opening, providing the benefits of more drastic and invasive surgical approaches with the safety and ease of minimally invasive techniques.

FIGS. 9-19 illustrate examples of possible profiles of the distraction device and the multi-tiered support structures that can be formed by such distraction devices. The various profiles can aid in shape retention so as to keep the distraction device in the shape of the deployed support structure and substantially accommodate resistance to both compressive and lateral forces, among other advantageous features. All of the embodiments in these figures preferably include a channel or passageway generally designated 172a-172i for mounting the distraction device onto the guide member. The central channel in some embodiments also can be utilized for directing the flow of bone filler or the delivery of drugs or other fluid materials.

In FIG. 9, the cross-sectional profile is generally square and in FIG. 10, the cross-sectional profile is generally rectangular. In both of these embodiments, the top surfaces 174a, 174b and bottom surfaces 176a, 176b of the distraction devices are substantially flat surfaces and are in contact when the distraction device is in the deployed configuration. The contact between the top and bottom surfaces results in a support structure that is very good at resisting compressive forces. Additionally, as illustrated in FIG. 9 the distraction device can have a porous coating 178 throughout or at least on the sides of the distraction device for better integration into the tissue to be treated.

In FIG. 11, the cross-sectional shape is a custom tongue and groove profile having a corrugated shape in which the top surface 174c and the bottom surface 176c of the distraction device each include a plurality of peaks 180 and valleys 182. The peaks 180 and valleys 182 of the top surface 174c engage the peaks 180 and valleys 182 of the bottom surface 176c to provide interfering surfaces that add stability and resists lateral slippage.

In FIG. 12, the cross-sectional shape is a custom profile with a single tongue and groove configuration. The distraction device has a groove 184 formed in the top surface 174d of the distraction device and a raised rib or tongue 186 extending from the bottom surface 176d of the distraction device. When the distraction device is curved into the deployed configuration, tongue 186 extends into groove 184 to provide interfering surfaces that add stability and resists slippage and shifting due to lateral forces.

In FIG. 13, the cross-sectional shape is a custom profile in which the top surface 174e has a convex configuration and bottom surface 176e has a concave configuration. When the distraction device forms a support structure the concave and convex surfaces 174e and 176e engage to add stability and reduce slippage and shifting due to lateral forces.

FIGS. 5 and 14-17 illustrate embodiments of the distraction device that include features which add flexibility to the device and assist in directing and limiting the direction of flowable bone filler material injected into the treatment site. In the illustrated embodiments, materials, such as bone filler or medications, can be injected into any of the channels 172f-172i. The material will flow through the channel and into slots or recesses located in the distraction device. The slots direct and/or limit the flow of the material to a specific region within the treatment site.

As mentioned above, the illustrated embodiments also include features that aid in the insertion of the distraction device and assist in flexing or curving of the distraction device as it is guided over the guide member. For example, the absence of material between the teeth, i.e., slots, allows the material to bend, thereby enhancing the flexibility of the distraction device and making it easier for the distraction device to follow the contour of the guide member as the guide member shapes the distraction device into the deployed shape.

FIG. 5 illustrates a distraction device wherein the distraction device includes upward directed slots 146. When bone filler is injected into the channel 156, the boner filler flows out of the slots 188 and into areas on both the inside and outside of the distraction device support structure.

Figure 14:
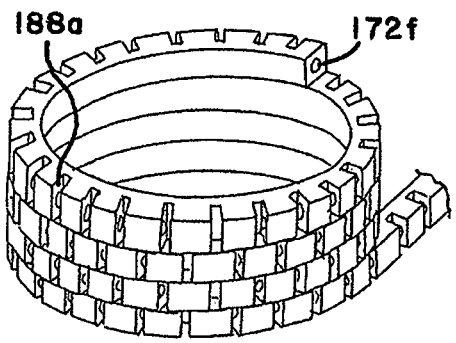

In FIG. 14, the distraction device includes outwardly facing slots 188a. When bone filler is injected into the channel 172f, the bone filler flows out of the slots 188a into the area outside of the distraction device support structure. Thus, the slots 188a direct the flow of bone filler toward the outside of the distraction device, and the distraction device support structure acts as a barrier, leaving the inner area defined by the distraction device substantially free of bone filler material.

Figure 15:
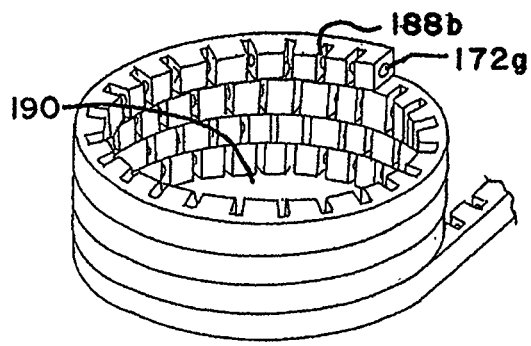

In FIG. 15, the distraction device includes inwardly facing slots 188b. When bone filler is injected into the channel 172g, the bone filler flows out of the slots 188b and into the inner space 190 defined by the distraction device. Thus, the slots 188b direct and limit the flow of bone filler toward the inside of the distraction device, and the distraction device acts like a container that contains the bone filler within the distraction device, leaving the outside region of the distraction device substantially free of bone filler material.

Figure 16:
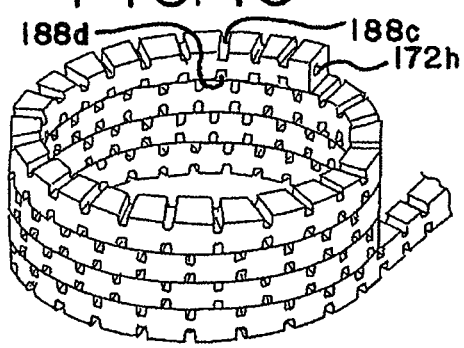

In FIG. 16, the distraction device has upwardly and downwardly facing slots 188c, 188d, which allows bone filler to flow into regions inside and outside of the distraction device.

Figure 17:
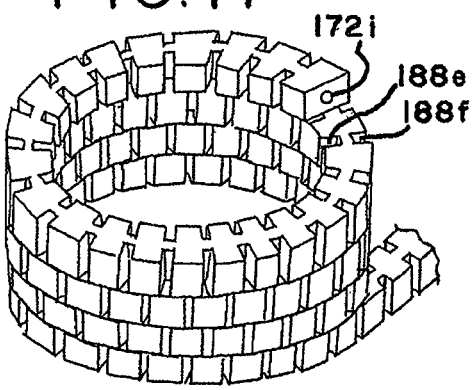

In FIG. 17, the distraction device has inwardly and outwardly facing slots 188e, 188f. In this embodiment, the inwardly and outwardly facing slots 188e, 188f direct the bone filler toward both the inner space defined by the distraction device and the region outside of the distraction device.

The size and dimension of the distraction device when used for the treatment of vertebral compression fracture is preferably of a size that can be inserted through a cannula no larger that about a 6 gauge size (working diameter about 0.173 inches (about 4.39 mm)) which would allow the distraction device to have a generally square profile of about 0.118 inches×0.118 inches (about 3 mm×3 mm). Other sizes and dimensions could be used depending on the application. The length of the distraction device could be pre-determined or could be cut to fit during the treatment.

Figure 18:
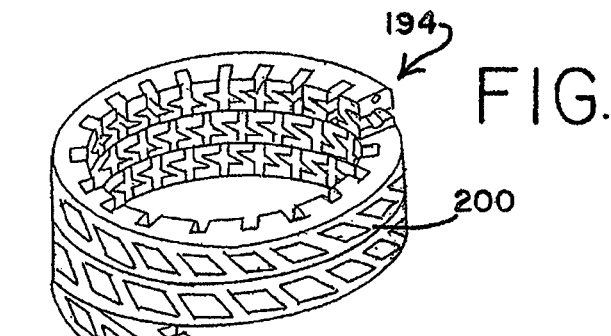
Figure 19:
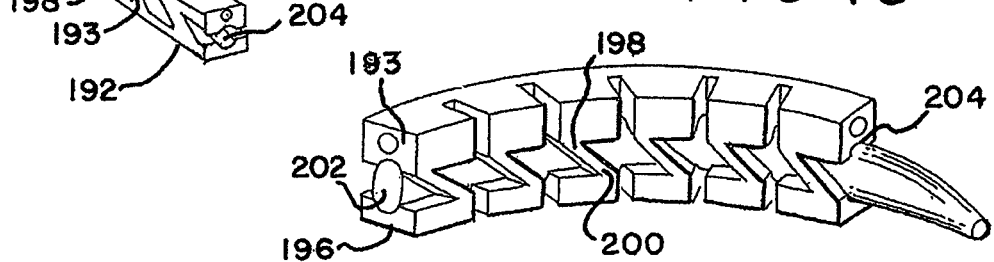

FIGS. 18 and 19 illustrate another embodiment of distraction device 192 that comprises a generally elongated member which can be configured to form a distraction device support structure 194. Distraction device 192 includes a top portion 193 and a bottom portion 196 connected to each other by deformable sidewalls 198. The deformable sidewalls 198 include a plurality of connection members 200 spaced along each of the sidewalls. The connection members 200 are biased to hold the top portion 193 and bottom portion 196 in a relatively tight configuration.

Referring to FIG. 19, a distraction member 202, such as the illustrated elongated member, can be inserted into and through a passageway 204 extending along the center of the distraction device 192. When distraction member 202 is inserted into passageway 204, the distraction member 202 contacts and forces the upper and lower portions 193, 196 of the distraction device 192 apart, and the deformable sidewalls 198 deform or stretch, i.e., the connection members 200 deform or stretch, to accommodate the separation of the upper and lower portions 193, 196. The separation of the upper and lower portions 193, 196 increases the height of the distraction device and support structure.

Other devices, systems and methods particularly useful with medical devices and procedures described herein are described in U.S. patent application Ser. No. 12/035,298, filed Feb. 21, 2008, entitled "Devices for Treating the Spine" filed on the same day as the present application, which is incorporated herein by reference.

FIGS. 20-24 illustrate one embodiment of the deployment of the distraction device 136 into a vertebral body 206. Referring to FIG. 20, an introducer sheath or working cannula 208 is introduced through the back of a patient while the patient is lying in a prone position. Fluoroscopic guidance using a biplane imaging system for better visualization of the spine may be used to help guide the delivery system to the desired location. Working cannula 208 can be introduced into vertebral body 206 using a transpedicular access approach. Once working cannula 208 is inserted through an access port 210 and is in the desired position, a delivery cannula 212 is inserted into working cannula 208 and the guide member 154 is advanced forward through the delivery cannula 212. Alternatively, the delivery cannula may be inserted into the vertebra without an introducer sheath.

As explained above, the guide member 154 is preferably made of a shape memory material that has an initial or free state in the shape of a coil or spring. As the guide member 154 is inserted into the delivery cannula 212, the cannula constrains the guide member into a generally elongated linear configuration, allowing an easy and minimally invasive deployment of the guide member into the treatment site. Because of the shape memory properties, the guide member 154 will return to its coil-shaped free state once the constraint is removed, i.e., as the guide member exits the distal end portion 214 of the delivery cannula 212 and enters the vertebral body 206. The guide member 154 can be advanced through delivery cannula 212 manually or with the aid of an advancing mechanism.

As the guide member 154 exits the distal end portion 214 of the delivery cannula 212 and enters the vertebral body 206, the distal end portion 160 of the guide member begins to return to its unconstrained shape, i.e., the distal end portion of the guide member begins to wind into its coil shape. Guide member 154 is advanced and deployed into cancellous bone of the vertebral body 206 until the coil shape reaches the desired height or has the desired number of loops or windings 161. As noted earlier, the guide member itself may function to distract or separate the endplates of a damaged vertebra.

After the guide member 154 has achieved a desired deployed configuration, distraction device 136 is advanced over the proximal end portion 158 of the guide member 154 by pusher member 162. As the pusher member 162 is advanced, it contacts the distraction device 136 and advances it forward or distally over the guide member 154. A drive mechanism can be employed to advance the pusher member 162.

Referring to FIG. 22, as the distraction device 136 is advanced forward (distally) over the guide member 154, the guide member guides the distraction device through delivery cannula 212 and into vertebral body 206. As noted above, the distal end 164 of the distraction device 136 can be tapered, ramped or otherwise shaped to aid in passing through tissue.

In the vertebral body, the distraction device 136 follows along the coiled shaped distal end portion 160 of the guide member 154 and winds into a coil shaped support structure 150 as shown in FIGS. 22 and 23. The side slots in the distraction device facilitate curving of the distraction device so that it follows the contour of the guide member. With each formation of an additional coil or windings 151 of the support structure 150, the support structure increases in height. As the support structure 150 increases in height, it distracts and supports the endplates of the vertebra, restoring or partially restoring vertebral height and stabilizing the vertebral body 206. When treating a fractured vertebral body, the distraction of the endplates stabilizes the fracture because the load is no longer applying pressure onto the fractured section or onto the fragmented pieces that can pressure the nerve endings surrounding the vertebral body, and thus back pain is reduced.

One advantage of this embodiment of the distraction device, as noted above, is that it can be inserted through a small access hole and a much larger three dimensional support structure, such as a multi-tiered arrangement or scaffolding, can be built within a limited or confined space between or within the tissue layers. For instance the distraction device 136 can be inserted through a small access hole and the support structure 150 can be built one loop at the time by adding one thickness of the distraction device over another one. As an example, the average vertebral body is 18 mm in height. As illustrated in FIG. 2, after a vertebral body compression fracture, the vertebral body can be about half of the height of a normal vertebral body, which would result in a compressed body of about 9 mm. By way of example, a guide wire in the form a wire with a 1 mm in diameter with a pitch about half of the wire size would require about 5 loops to span from endplate to endplate. When the distraction device is inserted onto the guide member, it will start winding along the loops and distract or push up and down in the axial direction which may benefit from the mechanical advantage of advancing over a coil. Because the fractured body has less resistance, it will expand the distance between the two endplates until they are preferably at the pre-fractured position, as illustrated in FIG. 24.

After the distraction device 136 has been deployed, the guide member 154 can be retracted from the distraction device and removed from the system. This can be accomplished by holding the pusher member 162 in place while retracting the guide member 154 in a proximal direction. For example, the guide member 154 can be retracted proximally by reversing the advancing mechanism.

FIGS. 25-29 illustrate one method of deploying a distraction device 136 over a guide member 154 wherein the distraction device and the guide member are deployed incrementally. The incremental method described herein can be used to deploy the distraction device into tissue or between tissue layers at any desired location within the body and is particularly useful in treating spinal tissue, such as vertebrae and intervertebral disks.

Referring to FIG. 25, a portion 216 of the guide member 154 is advanced out of the distal end portion 218 of a cannula 220 and into a treatment site. Next, the distraction device 136 is advanced over the portion 216 of the guide member 154 (FIG. 26). The guide member 136 is then further advanced out of the cannula 220 (FIG. 27) to extend portion 216 of the guide member 154 past the distal end portion 164 of the distraction device 136, and the distraction device 136 is then further advanced over the guide member 154 (FIG. 28). The incremental deployment of the guide member 154 and distraction device 136 continues until the support structure 150 attains the desired height (FIG. 29).

One of the benefits of incremental deployment is that the distraction device aids in maintaining the shape of the guide member as the guide member is deployed. For example, the distraction device supports the guide member and aids in preventing radial dilation of the guide member. Another benefit is that the distraction device provides a path for the guide member, which reduces the amount of friction between the guide member and the tissue in which it is inserted.

During deployment of the guide member and the distraction device, it is advantageous to have the ability to control the placement and orientation of the guide member and spinal implant within the treatment site. For example, if the guide member and distraction device are deployed at an undesired trajectory or orientation, the surgeon must retract the guide wire and/or the distraction device, reorient the deployment system and redeploy the guide member and/or the distraction device. Additionally, when the guide member is being deployed at a location that is surrounded by sensitive tissue, such as nerves and blood vessels, it is highly advantageous to be able to predict and control the trajectory and/or orientation of the guide member during deployment.

Figure 33:
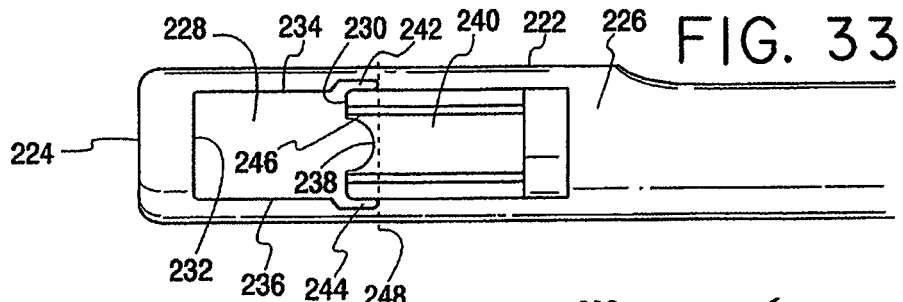
FIG. 33 is a side view of one embodiment of a distal end portion of a deployment cannula.
Figure 34:
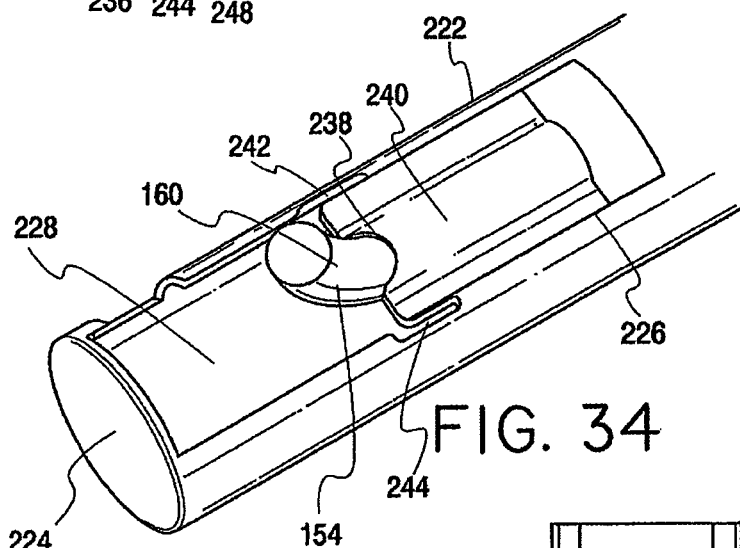
FIG. 34 is a perspective view of the distal end portion of the deployment cannula of FIG. 33, shown with a guide member being deployed from therefrom.

FIGS. 33-42 illustrate various embodiments of the distal end portion of the delivery cannula that include features and elements for controlling the trajectory and orientation of the guide member during deployment. Referring to FIGS. 33 and 34, delivery cannula 222 includes an end wall 224 and a sidewall 226. Sidewall 226 includes an opening 228 therethrough, which communicates with the internal passageway of cannula 222. Opening 228 is defined by proximal edge 230, a distal edge 232 and top and bottom edges 234, 236. The proximal edge 230 includes a recess or "keyhole" 238 that is configured to accept and mate with guide member 154 as it is advanced out of window 228. Referring to FIG. 34, as guide member 154 is advanced out of opening 228, the guide member engages recess 238, which constrains and controls guide member's location within opening 228, thus controlling its trajectory.

Optionally, sidewall 226 also can include a guide channel or "keyway" 240 that orientates guide member 154 within the internal passageway of the cannula 222 and guides the guide member 154 toward recess 238 as the guide member is advanced through the cannula 222. Furthermore, in the event that the proximal end portion 160 of guide member 154 is required to be retracted into cannula 222 so that the distal end portion 160 of guide member 154 is below-flush relative to proximal edge 230 or completely retracted into cannula, distal end portion 160 of guide member 154 will remain in contact with guide channel 240, thus, keeping the guide member aligned with recess 238. When guide member 154 is once again advance toward and out of window 228, guide channel 240 will direct the guide member 154 toward recess 238, thus ensuring that guide member 154 will exit out of window 228 at the desired location.

Figure 35:
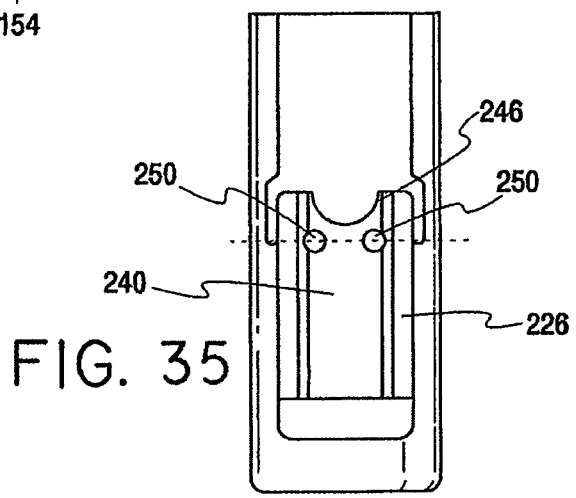
FIG. 35 is a side view of another embodiment of a distal end portion of a deployment cannula.
Figure 36:
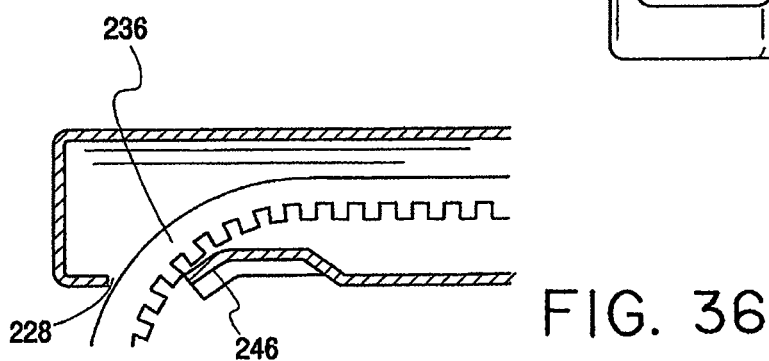
FIG. 36 is a cross-sectional view of the distal end portion of the deployment cannula of FIG. 33, shown with a distraction device being deployed therefrom.

In one embodiment, sidewall 226 includes cut outs 242, 244 located on either side of proximal edge 230 of window 228. Cut outs 242, 244 allow a portion of the sidewall or flap 246, adjacent proximal edge 230, to defect outwardly along line 248 of FIG. 33, as distraction device 136 is deployed through opening 228, as shown in FIG. 36. Flap 246 provides a bearing surface for distraction device 136 to ride against, which reduces friction, and thus reduces the drive force required to deploy the distraction device. In one embodiment, the material of sidewall 226 has sufficient strength so that flap 246 does not deflect outwardly under the force applied to it during the deployment of guide member 136 (as shown in FIG. 34), but has sufficient flexibility so that flap 246 deflects outwardly under the force applied to it during the deployment of distraction device 136 (as shown in FIG. 36). Referring to FIG. 35, to assist the deflection flap 246, sidewall 226 can include stress relief holes 250 that allow the material to more easily bend or flex along line 251 as the distraction device is deployed.

It will be understood that the distal end portion of the cannula can include any of these features, i.e., the keyhole, keyway, and flap, individually or in any combination.

Figure 37A:
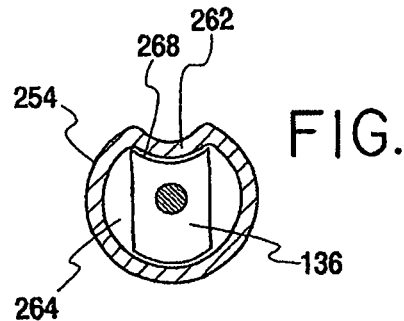
FIG. 37A is a cross-sectional view of the deployment cannula of FIG. 37, shown with a distraction device located therein.
Figure 37:
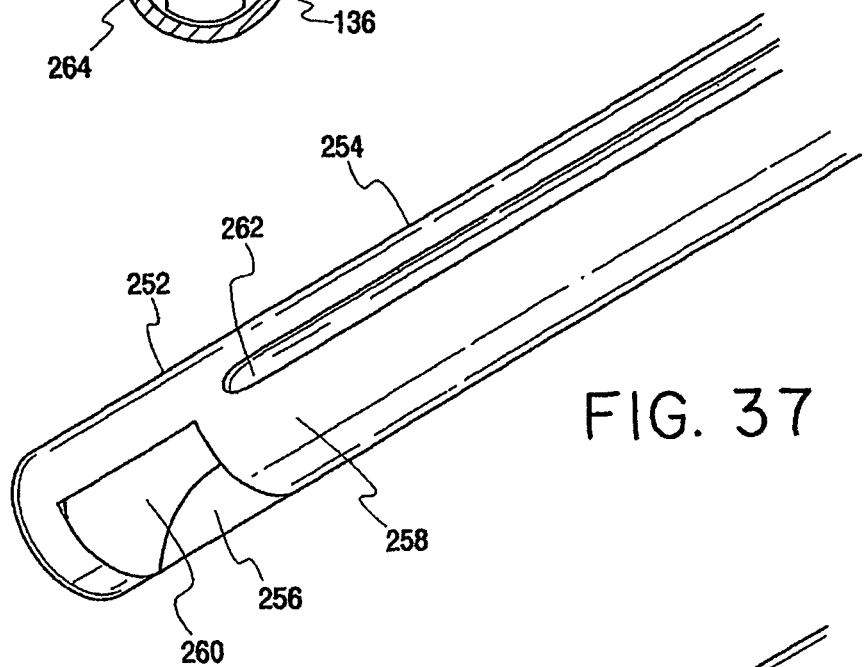
FIG. 37 is a perspective view of another embodiment of a distal end portion a deployment cannula.

FIG. 37 illustrates another embodiment of a distal end portion 252 of a deployment cannula 254. Deployment cannula 254 includes an opening 256 in the sidewall 258 of the cannula. In this embodiment, cannula 254 includes a curved internal wall 260 located within the internal passageway of cannula 254. Curved internal wall 260 is sloped so that when the guide member and the distraction device are advanced through the internal passageway of cannula 254, the distal end portions of the guide member and the distraction device will contact curved internal wall 260 and be directed toward opening 256. In other words, the slope of the curved internal wall 260 guides the advancing guide member and distraction device toward opening 256, providing a smooth transition and exit of such members out of opening 256.

Also, as illustrated in FIGS. 37 and 37A, a portion 262 of the sidewall 258 can be curved so that it protrudes into internal passageway 264 of cannula 254 to provide a guide element within the cannula that orients and maintains the alignment of the distraction device 136 within deployment cannula 254. Referring to FIG. 37A, as distraction device 136 is advanced through internal passageway 264 of deployment cannula 254, protruding portion 262 of sidewall 258 engages a recess or groove 268 in one of the surfaces of distraction device 136. This engagement aligns distraction device 136 within deployment cannula 254 and maintains the orientation of the distraction device within the deployment cannula as the distraction device is advanced therethrough.

Figure 38:
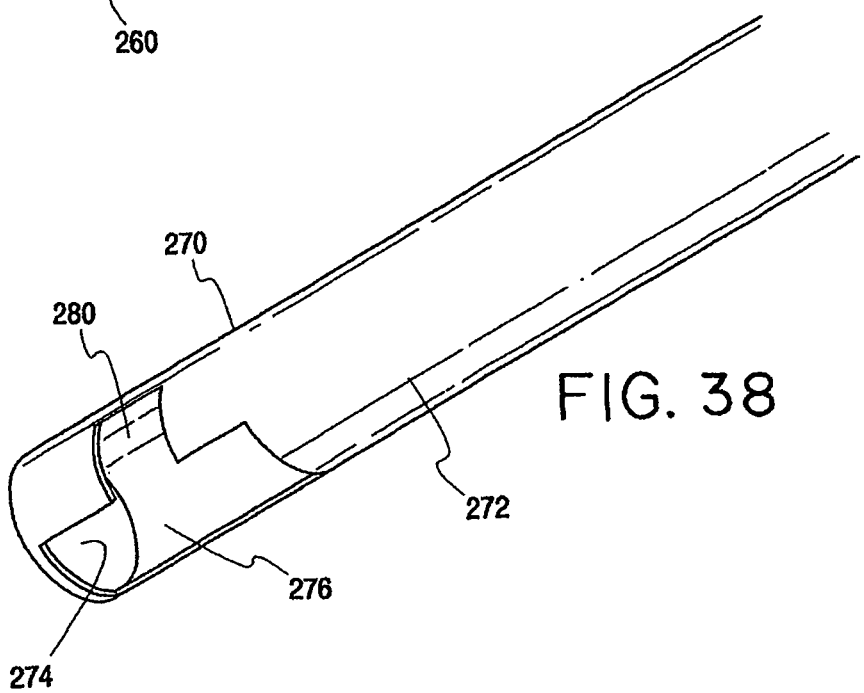
FIG. 38 is a perspective view of one embodiment of a distal end portion of a working cannula.

FIG. 38 illustrates one embodiment of a working cannula 270 that can be used in conjunction with a deployment cannula to deploy a guide member and a distraction device between tissue layers. Working cannula 270 includes a sidewall 272 and an end wall 274. Working cannula 270 also includes an opening 276 in sidewall 272 that communicates with internal passageway of working cannula 270. Opening 276 varies in size and includes a wide portion 278 and a narrow portion 280.

Figure 39:
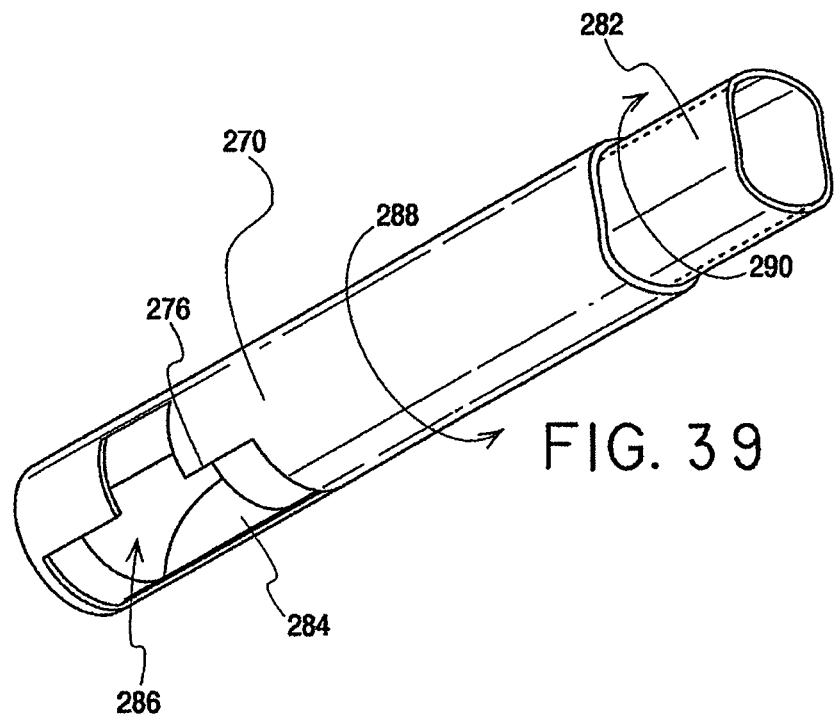
FIG. 39 is a perspective view of the working cannula of FIG. 38 with the deployment cannula of FIG. 37 inserted therein and, shown with the deployment cannula and working cannula in a first position.

Referring to FIG. 39, in use, a deployment cannula 282, which may be any of the deployment cannulas described above, is inserted into the internal passageway of working cannula 270 so that opening 284 of deployment cannula 282 is aligned with opening 276 of working cannula 270, collectively defining a deployment window 286. As indicated by arrows 288 and 290 working cannula 270 and deployment cannula 282 are rotatable relative to one another. As used herein "relative rotation" is intended to include the situation in which one of the cannulas is rotated relative to the other cannula, i.e., one cannula is held in place while the other is rotated, and the situation where both cannulas are rotated simultaneously. As will be explained in more detail below, the size of window 286 can be adjusted by rotating the cannulas relative to one another.

Figure 40:
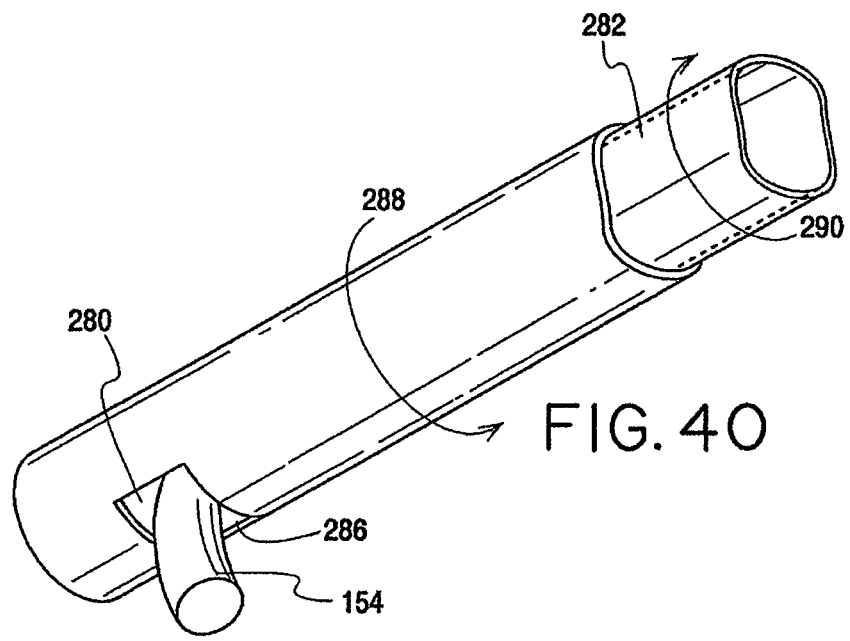
FIG. 40 is a perspective view of the combination of the deployment cannula and working cannula of FIG. 39, shown in a second position and having a guide member extending therefrom.

Referring to FIG. 40, deployment cannula 282 and working cannula 270 are rotated relative to one another so that narrow portion 280 of opening 276 of working cannula 270 is aligned or located over opening 284 of deployment cannula 282. Narrow portion 280 of opening 276 of working cannula 270 is smaller in size than opening 284 of deployment cannula 282, which results in a relatively small deployment window 286 that is large enough to allow deployment of the guide member 154, but small enough to prevent deployment of the distraction device. One advantage of such a configuration is it that is prevents inadvertent or premature deployment of the distraction device because the relatively small size of deployment window 286 prevents such deployment. When deployment window 286 is in such a configuration, guide member 154 is advanced through deployment cannula 282 and deployed out of deployment window 286. In one embodiment, the dimensions of deployment window 286 in the relatively smaller configuration are slightly larger than the dimensions of guide member 154, so that window 286 constrains guide member 154 and control its orientation and trajectory as it exits the window.

Figure 41:
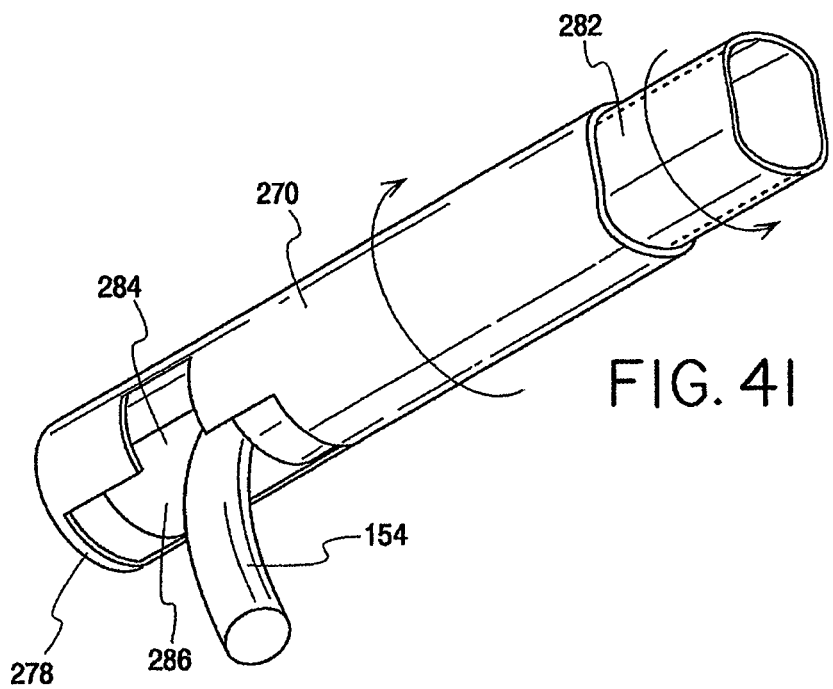
FIG. 41 is a perspective view of the combination of the deployment cannula and working cannula of FIG. 40, shown in the first position and having a guide member extending therefrom.
Figure 42:
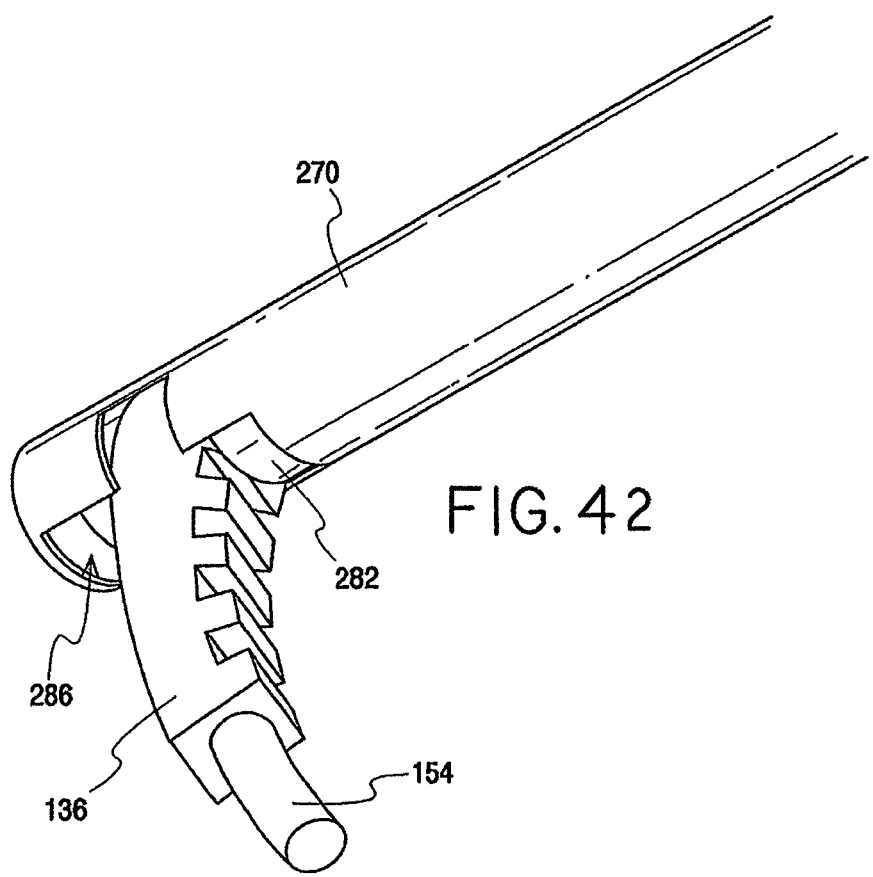
FIG. 42 is a perspective view of the combination of the deployment cannula and working cannula of FIG. 40, shown in the first position and having a distraction device being deployed therefrom.

After a desired amount of guide member 154 has been deployed, working cannula 270 and deployment cannula 282 are again rotated relative to one another to adjust the dimensions of the deployment window 286. Specifically, the cannulas are rotated so that the wide portion 278 of opening 276 of working cannula 270 is aligned with opening 284 of deployment cannula 282, as illustrated in FIG. 41. Wide portion 278 of opening 276 of working cannula 270 preferably is the same size as or larger than opening 284 of deployment cannula 282, and in any event is large enough to allow the advancement of distraction device 136 through the window 286. Referring to FIG. 42, after window 286 has been adjusted to the larger configuration, distraction device 136 is advance along guide member 154, through deployment cannula 282 and out of window 286.

As discussed above, the distraction device of the disclosure is preferably but not exclusively used with flowable material, such as curable bone filler material, to add stability to the distraction device and support structure between the distracted tissue, i.e., the endplates of the vertebra. Flowable filler material can be introduced into the treatment site using a variety of different methods and techniques. For example, bone filler material can be introduced by the methods and techniques described in co-owned U.S. patent application Ser. No. 11/464,782, filed Aug. 15, 2006, which has been incorporated by reference above, and U.S. Provisional Patent Application No. 61/030,287, filed Feb. 21, 2008, entitled "Methods of Interdigitating Flowable Material with Bone Tissue" filed on the same day as the present application, which is herein incorporated by reference.

FIGS. 30-32 illustrate another embodiment a device and method for injecting flowable material into the treatment site and methods of use thereof. FIG. 30 illustrates a flowable material injection device 300. Device 300 includes a supply of flowable material 302, such as a syringe containing flowable material 304, and a flowable material delivery tube or needle 306. Delivery tube 306 has a proximal end portion 308, a distal end portion 310 and a fluid passageway therebetween. Proximal end portion 308 is configured to be operatively connected to and receive flowable material from flowable material supply 302.

Distal end portion 310 includes an opening 312 for delivering flowable material into a treatment site. Distal end portion 310 preferably is comprised of a shape memory material, such as Nitinol or other shape memory alloy, and in its initial or free-state configuration, distal end portion 310 has a curved portion 314, which permits directional delivery of the flowable material from opening 312. Additionally, distal end portion 310 can be constrained in a generally linear or straight configuration, as illustrated in FIG. 31. For example, in use, delivery tube 306 can be inserted into a cannula, such as a working cannula, to access a treatment site. When delivery tube 306 is inserted into the working cannula, distal end portion 310 of the delivery tube is constrained in the generally linear configuration, shown in FIG. 31, for passage through the cannula. When distal end portion 310 of delivery tube 306 exits out of the cannula, the distal end portion returns to its curved configuration to permit directional deployment of flowable material.

FIG. 32 illustrates one method of employing delivery device 300 to deliver flowable material 304 into a resident volume 316 defined by a distraction device 318. In FIG. 32, distraction device 318 has been deployed into a vertebral body 320 in accordance with any of the methods described above. After distraction device 318 has been deployed, the working cannula 322 is positioned within vertebral body 320 so that distal end opening 324 of working cannula 322 is located adjacent resident volume 316 of distraction device 318. Delivery tube 306 is inserted into working cannula 322 and distal end portion 310 of the delivery tube is constrained in the generally linear configuration as it is advanced through the working cannula. When distal end portion 310 of delivery tube 306 exits opening 324 of working cannula 322, the constraining force is removed from distal end portion 310 of delivery tube 306 and the delivery tube returns to its original curved configuration. Preferably, the delivery tube 306 curves so that opening 312 in distal end portion 310 of the delivery tube is located in or oriented toward resident volume 316. Once distal end portion 310 of delivery tube 306 is in the desired location, flowable material 304 is injected into delivery tube 306 from fluid supply 302 and delivered through delivery tube 306 into resident volume 316. If cancellous bone material is located within the resident volume, the flowable material interdigitates with the cancellous bone tissue.

FIG. 90 illustrates another embodiment of injecting flowable material into a vertebral body. In this embodiment flowable material 304 is injected on the superior side 326 of distraction device support structure 318, the inferior side 328 of distraction device support structure 318 or on both sides 326, 328. For example, in the illustrated embodiment, a vertebra 330 has a distraction device support structure 318 deployed therein, and flowable material 304 is injected only on the superior side 326 of support structure 318. The flowable material 304 can cover the superior side 326 of support structure 318 to create a cap-like structure that fills any portions of the cancellous bone between the superior side 326 of the support structure 318 and the superior vertebral endplate 332. The flowable material 304 can be injected by any method know in the art or by any of the methods previously described in the above referenced co-owned patent applications.

In a further embodiment, the flowable material can be injected into a selected number of loops or windings of the distraction device support structure. For example, after the distraction device has been deployed to form the distraction device support structure, cement could be injected into the resident volume of the support structure so that a portion of the resident volume defined by a selected number of loops is filled with cement and a portion of the resident volume defined by the rest of the windings remains unfilled by cement. Filling only a portion of the resident volume of the distraction device support structure results in a distraction device support structure having portions of varying levels of flexibility and stiffness.

FIGS. 107-112 illustrate an optional compressible feature of the distraction device. As explained above, the distraction device is preferably made of a substantially rigid biocompatible material, such as a substantially rigid thermoplastic material, for example PEEK. Because of the natural characteristics of such materials, the distraction device is substantially rigid or incompressible in the dimension or direction between the top surface and the bottom surface of the distraction device. As used herein the terms "substantially rigid" and "substantially incompressible" are intended to mean that the material and the device do not substantially deflect under loading. The rigidity of the distraction device in this dimension results in the creation of a substantially rigid or incompressible support structure formed by the distraction device. While a substantially rigid support structure is highly advantageous in many applications, there are some applications where having an elastically compressible support structure has some advantages. As used herein the term "elastically compressible" is intended to mean that the device compresses or substantially deflects when loading is applied to the device, and the device elastically returns to a less compressed state as the load is reduced and/or substantially returns to its original uncompressed state when the load is removed.

FIG. 107 is an exemplary embodiment of a cross-sectional view of any of the distraction devices described herein. For example, FIG. 107 can be a cross-sectional view of the distraction device shown in FIG. 10 and taken along line 107-107. The distraction device 334 preferably comprises a substantially rigid thermoplastic material, such as PEEK, and includes stress relief chambers 336 located on either side of a center passageway 338. The stress relief chambers can be lumens that extend along the length of the distraction device or honeycombs or voids that are spaced along the distraction device. Additionally, although the illustrated embodiment only shows two chambers 336, there can be any number of chambers contained within the device.

As illustrated in FIG. 108, when a load or force F is applied to the top and bottom surfaces 340, 342 of distraction device 334, stress relief chambers 336 translate the force to the sidewalls 346, 348. Because there is no material, i.e. voids, between the sidewalls 346, 348 and the center wall 350, the sidewalls and center wall are allowed to bow of flex, which results in an elastic compression of distraction device 334 in the dimension or direction between the top and bottom surface 340, 342. As the load or compression forces are reduced, distraction device 334 elastically returns to a less compressed state, or in the situation wherein the load is completely removed, distraction device 334 elastically substantially returns to its original uncompressed state.

The amount of compression that the distraction device 334 will exhibit and the load under which the distraction device will substantially deflect or elastically compress largely depends on the size and configuration of stress relief chambers 336. In one embodiment, distraction device 334 is configured to substantially elastically compress under normal physiological loading endured by tissue of the human spine, and be substantially rigid or does not exhibit substantial deflection under loads less than those normally endured by tissue of the human spine.

For example, the normal range of physiological loading that tissue of the human spine endures is about 300 Newtons (N) to about 1000 N. In one embodiment, the stress relief chambers 336 are configured so that distraction device 334 is substantially incompressible or does not exhibit substantial deflection when it is place under a loading of less then 300 N, but is elastically compressible or exhibits a substantial deflection when it is place under a loading of about 300 N or greater. In another embodiment, distraction device 334 is substantially incompressible or remains rigid under a loading of less then 300 N and is substantially elastically compressible under a loading between about 300N to about 1000 N.

Compressible distraction device 334 can be used to treat damaged vertebral bodies and can also be used in nucleus replacement and fusion procedures to treat intervertebral disks. FIGS. 109-112 illustrate one method of treating an intervertebral disk with a compressible distraction device.

Figure 111:
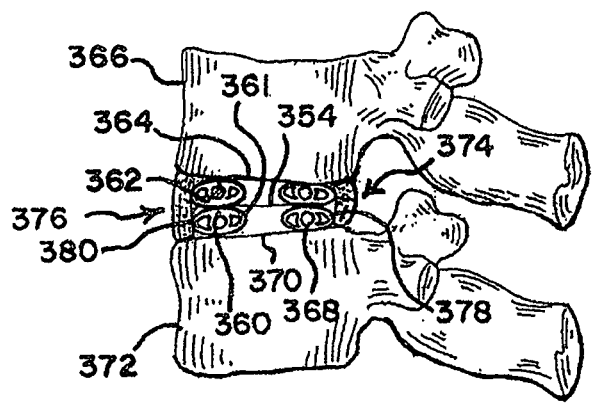
FIG. 111 is a side partial cross-sectional view of the intervertebral disk of FIG. 109, shown with the distraction device deployed therein and under a compressive load.
Figure 112:
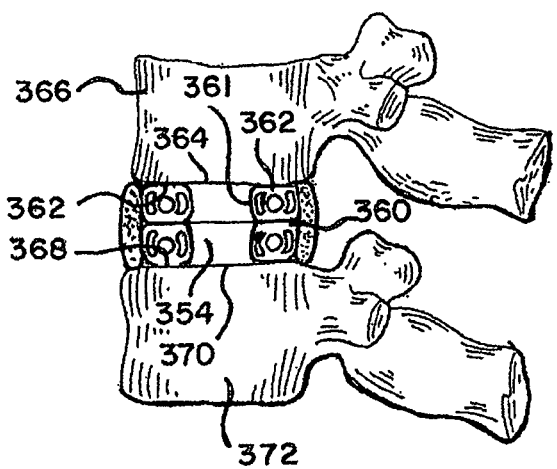
FIG. 112 is a side partial cross-sectional view of the intervertebral disk of FIG. 109, shown with the distraction device deployed therein.

FIG. 109 is a top view of an intervertebral disk 352 in which the nucleus material has been removed the disk, using standard techniques and procedures know in the art, leaving a nuclear space 354 within annulus 356. A guide member 358, such as any of guide members disclosed herein, is deployed into nuclear space 354 and compressible distraction device 334 having the elastically compressible feature is deployed over guide member 358 to form a support structure 360 within nuclear space 354, as illustrated in FIG. 110. Because nucleus disk space 354 is relatively small, the support structure includes about two or three loops or windings 361, as illustrated in FIGS. 111 and 112. However, the support structure can include more or less windings depending on the size of the distraction device and the size of the nucleus disk space.

After support structure 360 has been formed, guide member 358 is removed leaving the support structure in the nuclear space 354. Referring to FIGS. 111 and 112, when deployed within nuclear space 354, the top surface 362 of the support structure 360 contacts and supports the inferior endplate 364 of the superior vertebra 366, and the bottom surface 368 of the support structure 360 contacts and supports the superior endplate 370 of the inferior vertebra 372. As the spinal column moves during normal activities, the endplates 364, 370 apply loading to support structure 360. Comparing FIGS. 111 and 112, FIG. 112 illustrates support structure 360 under an at-rest loading of about 300 N or less, wherein support structure 360 has very little or no compression, i.e., does not exhibit substantial deflection. In contrast, FIG. 111 illustrates support structure 360 under a loading of greater than about 300 N. Under this loading, support structure 360 substantially deflects or yields to the force and elastically compresses. Additionally, as exemplified by FIG. 111, when there is uneven loading between the posterior side 374 and anterior side 376 of the spinal column, i.e., the posterior side 374 of the spinal column applies a greater loading than the anterior side 376, the posterior side 378 and anterior side 380 of support structure 360 can elastically compress in different amounts to accommodate such uneven loading.

As explained above, when the loading is remove or returns to the loading of an at rest state, support structure 360 returns to the less compressed state as shown if FIG. 112. Additionally, the above described distraction device can be used in a fusion procedure in which bone graft material can be inserted in and around the distraction device.

Depending on the procedure, sometimes it is necessary for the distraction device to channel or bore through tissue, such as cancellous bone. For such applications, the distal end portion of the distraction can be configured to reduce the amount of penetration force required for insertion of the distraction device. For example, the distal end portion can be designed to reduce the amount of friction between the tissue and the distraction device, or the distal end portion can be designed to weaken the structural integrity of the tissue by breaking or cutting through the tissue.

Figure 43:
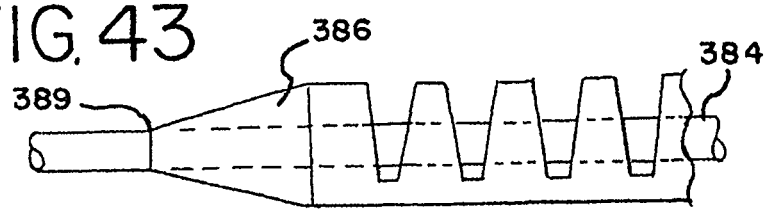

FIGS. 43-64 illustrate several different embodiments of distal end portions of distraction devices. FIG. 43 illustrates a distraction device 382 mounted on a guide member 384 where the distal end portion 386 of distraction device 382 includes a taper. The tapered distal end portion 386 minimizes the surface area of the frontal face 389 of distraction device 382 to reduce the bluntness of the frontal face and to provide a generally pointed distal end portion 386 that is more conducive to piercing tissue.

Figure 44:
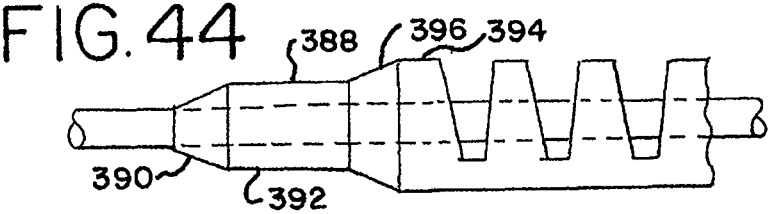

FIG. 44 illustrates a distal end portion 388 that includes a first tapered section 390 followed by a thin walled section 392 located proximal the first tapered section. The thin walled section 392 has a cross-sectional width or diameter that is generally smaller than that of the proximal end portion 394 of the distraction device. The thin walled section 392 provides flexibility to the distal end portion and a relatively longer tissue penetrating portion. The distal portion 388 also can include a second tapered section 396 proximal the thin walled section 394. The second tapered section 396 provides an angled surface leading to the proximal portion 394 of the distraction device.

Figure 45:
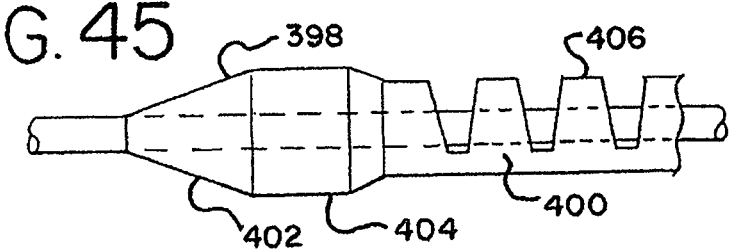

FIG. 45 illustrates a distal end portion 398 of a distraction device 400 that can be generally described as a flared nose. The distal end portion 398 includes a tapered section 402 that leads into a section 404 which has a diameter or cross-sectional width that is larger than the majority of the proximal portion 406 of distraction device 400. The flared nose creates a pathway that is larger than the remaining portion of the distraction device, which reduces drag as the proximal portion 406 of the device is inserted through tissue.

Figure 46:
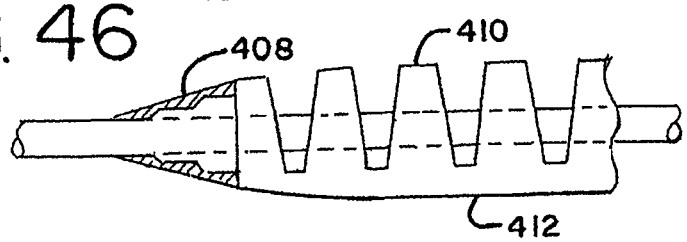

FIG. 46 illustrates a distal end portion 408 that is comprised of a material that is more rigid than the proximal end portion 410 of distraction device 412. In one embodiment, distal end portion 408 is comprised of a metal, such as stainless steel, titanium, platinum or any other suitable metal or metal alloy. The distal end portion 408 can also be comprised of any other suitable material that is more rigid than the proximal end portion 410 of distraction device 412, such as a rigid plastic or polymer. Optionally, the distal end portion 408 can include a radiopaque marker.

Figure 47:
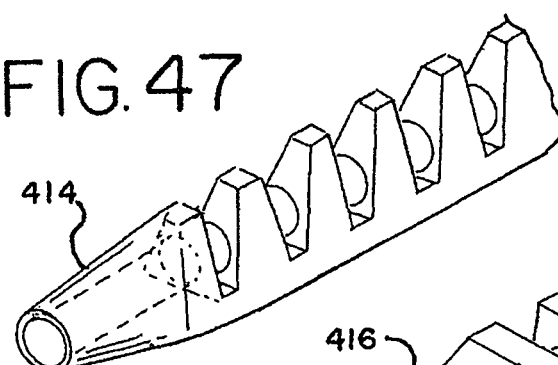

FIGS. 47-64 illustrate distal end portions of a distraction device that reduce the amount of penetrating force required to insert the distraction device into tissue by providing features that are adapted for cutting or breaking through tissue. For example, FIG. 47 illustrates a distal end portion 414 that has a tapered section adapted for piercing and breaking through tissue.

Figure 48:
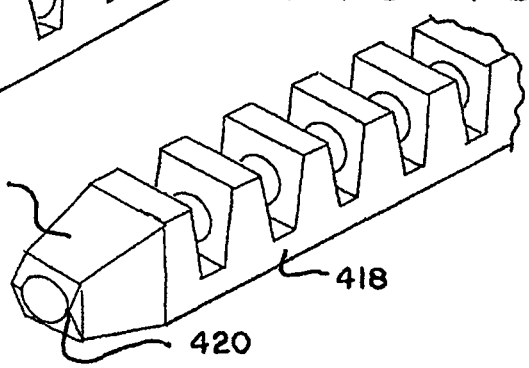

FIG. 48 illustrates a distal end portion 416 of a distraction device 418 that has a flat chisel or duckbill edge 420 that extends horizontally across the front face of the device.

Figure 49:
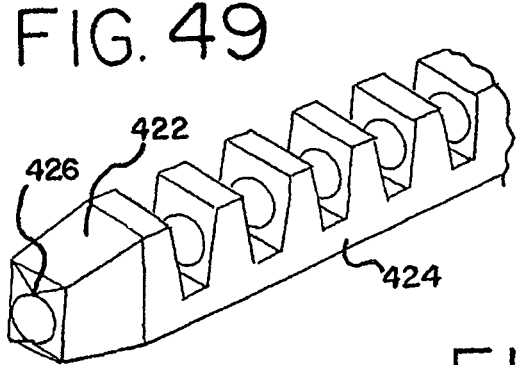

FIG. 49 illustrates a distal end portion 422 of a distraction device 424 that has a vertical chisel or duckbill edge 426 that extends vertically across the front face of the distraction device.

Figure 50:
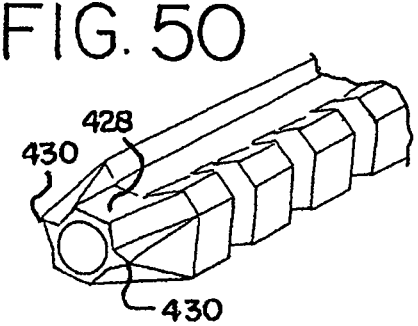

FIG. 50 illustrates a distal end portion 428 that has a star shaped configuration which includes multiple cutting edges 430.

Figure 51:
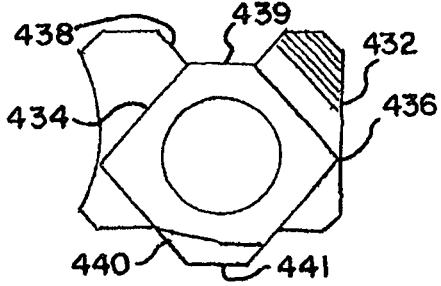
Figure 52:
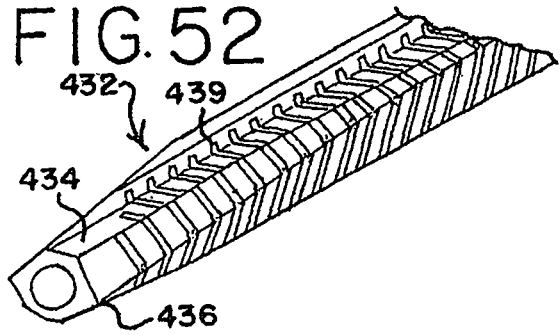

FIGS. 51 and 52, illustrate a distraction device 432 including a distal end portion 434 having a tapered polygonal shape with multiple cutting edges 436. Distraction device 432 also includes a top surface 438 that has a groove 439 extending along the distraction device, and a bottom surface 440 that includes a protruding portion 441 extending therefrom. When the distraction device is formed into the support structure, the protruding portion 441 mates with or seats within the groove 439 to give the structure strength and integrity to the support structure.

Figure 53:
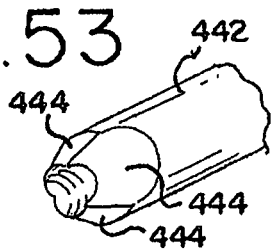
Figure 54:
Figure 56:

FIGS. 53, 54 and 56 illustrate distal end portions of a distraction device that have multi-faced cutting surfaces. For example, FIGS. 53 and 54 illustrate a distal end portion 442 that have three cutting faces 444, and FIG. 56 illustrates an embodiment that has four concave faces 446.

Figure 55:
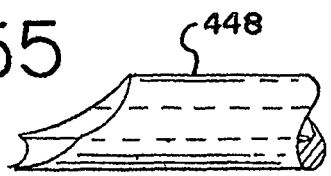
Figure 57:

FIGS. 55 and 57 illustrate a distal end portion 448 of a distraction device that has multiple cutting faces and edges in a complex configuration.

Figure 58:
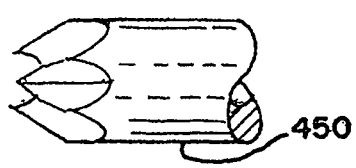
Figure 59:
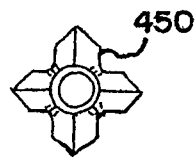

FIGS. 58 and 59 illustrates a distal end portion 450 of a distraction device that has multiple cutting faces and edges in a cross-shaped configuration.

FIGS. 60 and 61 illustrate a distal end portion 452 of a distraction device 454 that has a chiseled cutting edge 456 including a notch or groove 458. The notch 458 is configured to correspond to the shape and size of the guide member so that the distal end portion 452 of the distraction device nests against the guide member as the distraction device is advanced along a guide member and into tissue. Because the notch 458 nests against the guide member, the distal end portion 452 does not need to be as flexible as it follows along the guide member. Additionally, the notch 458 allows the longer distal end portion 452 to follow along the guide member without bending or flexing. Accordingly, the distal end portion 452 can be made of a longer, more rigid material that provides added stiffness for inserting the distal end portion into tissue.

Additionally, as illustrated in FIG. 62, the passageway 460 of distraction device 454 can be configured or keyed to the shape of the guide member 462. In the illustrated embodiment, the guide member has a square cross-sectional shape 40- and the passageway 460 includes flat surfaces 464 that mate with surfaces 466 of guide member 462. The keying of the distraction device 454 to the guide wire ensures proper orientation of distraction device 454 and prevents the distraction device from rotating about guide member 462. Prevention of distraction device rotation about the guide member reduces the amount of insertion force lost to such rotation, thus providing a greater insertion force for passage through tissue.

FIGS. 63 and 64 illustrate a distraction device 468 that includes a distal end portion 470, which is tapered to point and includes a surface that has serrated edges 472. The serrated edges cut and break tissue as the distraction 468 is inserted into the tissue.

The distraction devices of the present invention can also include surfaces that frictionally or mechanically engage each other during and after the formation of the distraction device support structure. The frictionally engaging surfaces can provide several benefits, such as eliminating or reducing movement between adjacent windings of the support structure, providing better rotational movement and transmission of torque during deployment and preventing unwinding or dilation of the windings under axial loading.

FIG. 65 illustrates one embodiment of a distraction device 474 that has frictionally engaging surface. The distraction device 474 includes top wall 476 and a bottom wall 478 both of which include a textured surface 480 at least partially extending along the distraction device. The textured surfaces of the top wall 476 and the bottom wall 478 are preferably configured to fictionally engage and interlock with each other when the distraction device is configured to define the distraction device support structure.

In the illustrated embodiment, the top wall 476 and the bottom wall 478 include knurls 482 that extend perpendicular to the axis X of the distraction device 474 when the distraction device is in a generally linear configuration. The knurls 482 can be similar to the knurls commonly found on plastic poker chips. However, it will be understood that the top and bottom surfaces could have a variety of differently configured frictionally engaging surfaces without departing from the present invention.

Referring to FIG. 66, as the distraction device 478 is wound to form the distraction device support structure 484, by the use of a guide member or other method, the knurls 482 on the top and bottom walls 476, 480 of the distraction device 474 frictionally or mechanically engage each other to interlock adjacent windings 486 together. During deployment of the distraction device 474 and while forming the support structure 484, the knurls 482 can function as a gear-like system that allows the force applied to the proximal end of the distraction device 478 to be efficiently translated to the distal end of the distraction device. Furthermore, during deployment, the distraction device 474 rotates as a single cylindrical unit rather than multiple independent windings.

Additionally, after the distraction device 474 has been implanted and the distraction device support structure 484 has been formed, the interlocking of the adjacent windings 486 reduced the amount of unwinding or radial dilation that can be caused by axial loading. For example, if the adjacent windings 486 are not interlocked, loading or force in the axial direction can cause the top and bottom ends of the distraction device support structure to dilate or unwind. The engagement between the knurls 482 of the top and bottom walls 476, 478 interlock the adjacent windings, which assists in reducing such dilation.

FIG. 67 illustrates another embodiment of a distraction device 488 that has surfaces that interlock as the distraction device forms the support structure 490. In this embodiment, the distraction device 488 has a generally wavy configuration wherein the distraction device includes peaks 492 and valleys 494 that are spaced apart by a pitch "P". As the distraction device 488 is deployed and winds or coils to form the support structure 490, the peaks 492 of one winding 496 align with and engage the valleys 494a of an adjacent winding 496a and the valleys 494 of the winding 494 align with and engage the peaks 492a of the adjacent windings 496a. During deployment, the mating of the adjacent peaks and valleys can function as a self-locating or self-aligning feature which assists in properly aligning each winding with the adjacent winding. Additionally, the wavy-shaped distraction device preferably has a rounded or smooth peaks and valleys that reduce friction as the distraction device is inserted into tissue.

In addition to the wavy construction, the distraction device 488 has a generally V-shaped or chevron shaped cross-section that has a groove 498 in the top wall and a protruding portion 500 bottom wall that mate when the distraction device 488 is formed into support structure 490. The mating of the groove 498 and protrusion 500 of the chevron shaped distraction device 488 assists stabilizing the distraction device support structure.

Figure 68:
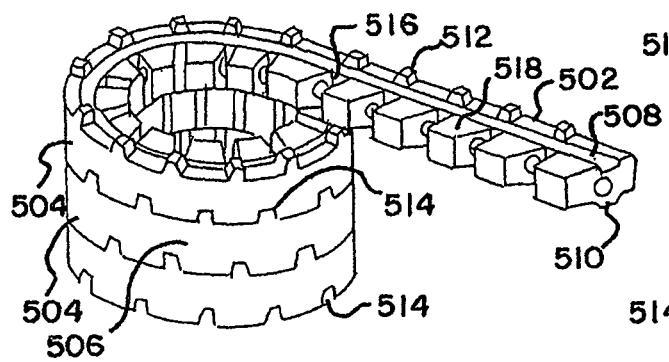
FIG. 68 is a perspective view of another embodiment of a distraction device and distraction device support structure.
Figure 69:
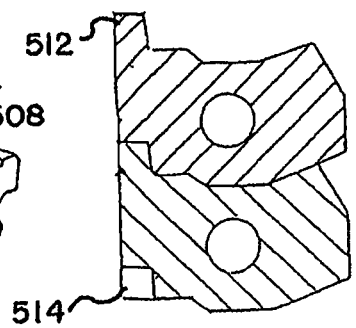
FIG. 69 is a partial cross-sectional view of the distraction device support structure of FIG. 68.

FIGS. 68 and 69 illustrate one embodiment of a distraction device 502 that is configured to provide interlocking windings or tiers 504 when the distraction device forms the distraction device support structure 506. The distraction device 502 includes a top wall 508 and a bottom wall 510. The top wall 508 includes a plurality of protrusions 512 that extend from the top wall and are spaced along the distraction device. The bottom wall 510 includes a plurality of recesses 514 that are configured to accept the protrusions 512 when the distraction device 502 is configured to form the support structure 506.

When the distraction device 502 is wound or configured to form the distraction device support structure 506, the protrusions 512 initially enter the slots 516 between the teeth 518. As the distraction device 502 continues to wind, the protrusions 512 move further into the slots 316 and eventually into the recesses 514 located in the bottom wall 510 of the distraction device 502 to interlock the adjacent windings 504 as illustrated in FIG. 69.

Figure 70:
FIGS. 70, 71 and 72 are illustrations of various embodiments of protrusions that can extent from the distraction device.
Figure 71:
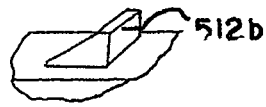
Figure 72:
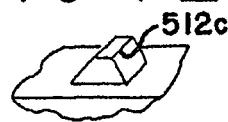

The protrusions 512 and the recesses 514 can have a variety of configurations. For example, FIG. 70 illustrates a protrusion 512a shaped like a cylindrical peg. FIG. 71 illustrates a protrusion 512b having one angled surface, and FIG. 72 illustrates a protrusion 512c having two angled surfaces.

Figure 73:
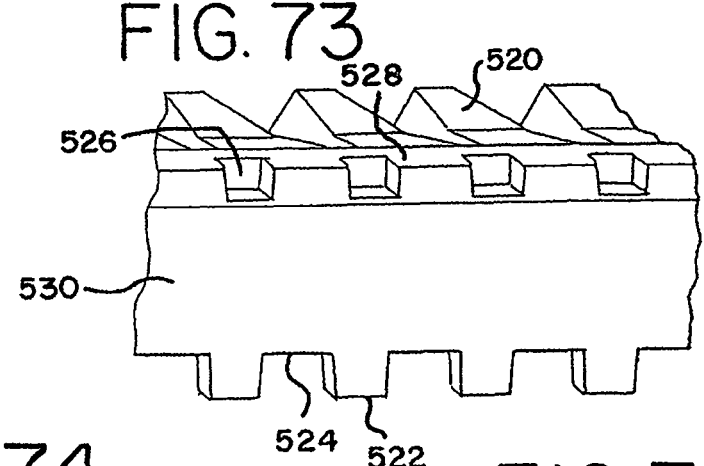
FIG. 73 is a perspective view of another embodiment of a distraction device.
Figure 74:
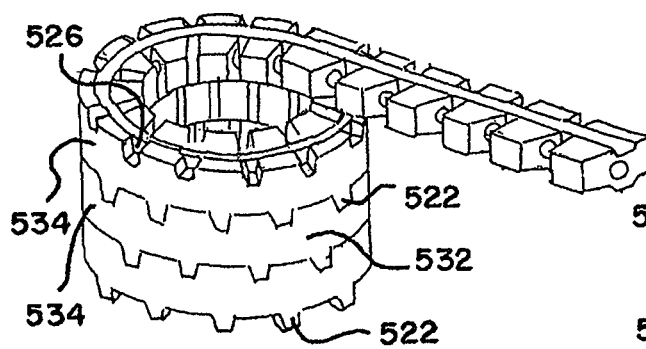
FIG. 74 is a perspective view of a distraction device support structure defined by the distraction device of FIG. 73.
Figure 75:
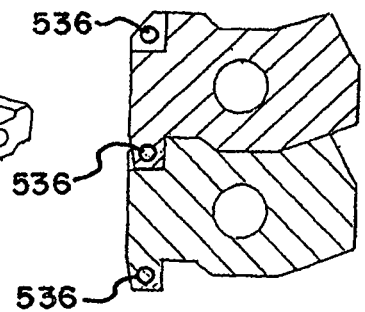
FIG. 75 is a partial cross-sectional view of the distraction device support structure of FIG. 74.

Referring to FIGS. 73-75, in an alternative embodiment of the distraction device 520, the protrusions 522 can extent from the bottom wall 524 and the recesses 526 can be located in the top wall 528 and in part of the back wall 530. As the distraction device 520 is wound to form the distraction device support structure 532, the protrusions 522 engage the recesses 526 and interlock the adjacent windings 534 (FIG. 74). Optionally, the protrusions 522 and the portions of the distraction devices between the recesses 526 could include a hole 536 (FIG. 75) extending therethrough and for receiving a retaining member. When the protrusions 522 engage the recesses 526, the holes 536 align to form a passageway in which a retaining member, such as a wire, can be inserted through the holes 536 to secure the adjacent windings 534 together and prove added stability to the support structure 532.

FIGS. 76-83c illustrate further embodiments of the distraction device wherein the distraction device includes hinged tabs that are movable between a first unlocked position and a second, locked position.

Figure 76:
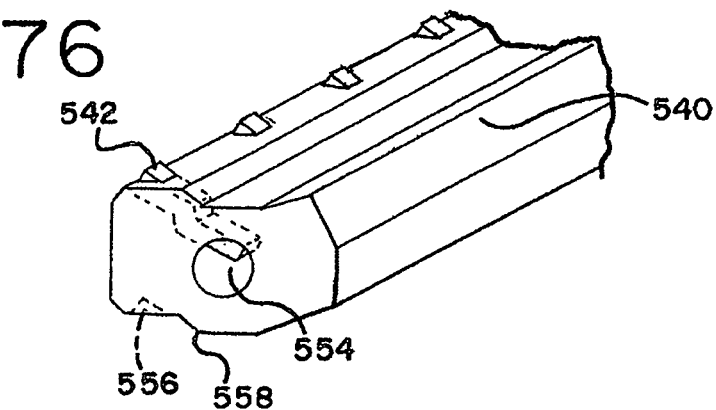
FIG. 76 is a perspective view of another embodiment of a distraction device.
Figure 77:
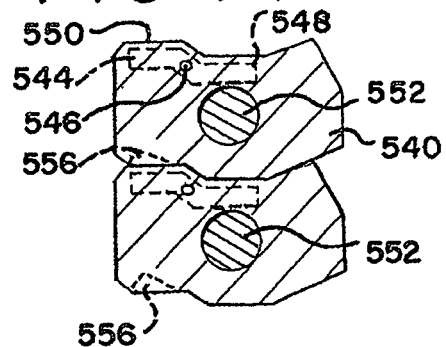
FIG. 77 is a cross-sectional view of a support structure defined by the distraction device of FIG. 76.
Figure 78:
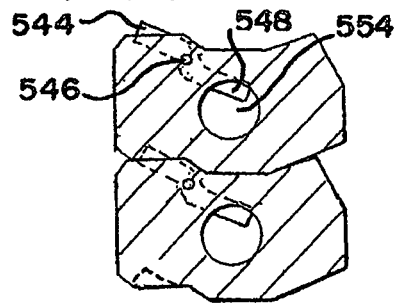
FIG. 78 is a cross-sectional view of the support structure of FIG. 77.

Referring to FIGS. 76 and 77 distraction device 540 includes movable tabs 542. Tabs 542 include a locking member 544, an activation member 546 and a hinge member 548, such as a pin, therebetween. As will be explained in greater detail below, the tab rotates about the hinge between an unlocked and a locked position. As shown in FIG. 77, when tab 542 is in the unlocked position, the locking member 544 is situated in a recess located in the top surface 550 of the distraction device 540, so that locking member 544 is level or below level with top surface 550 of distraction member 540. During deployment of the distraction device over a guide member 552, the guide member is located with passage 554 (shown in FIGS. 76 and 78) and in contact with the activation member 548, keeping tab 542 in the locked position. After the windings have been stacked one on top of the other to form the support structure, guide member 552 is removed from central passage 554 of the distraction device 540 and out of contact with activation member 548. Referring to FIG. 78, after guide member 552 has been removed from passageway 554, the activation member 548 moves into the passageway, and the tab 542 rotates about hinge 546 to move the tab into the locked position. Tabs 542 are biased to the locked position, by for example, weighting the tabs or employing a leaf spring, so that the tabs move to the locked position when the guide member is removed.

In the locked position, the locking member 544 extends above top surface 550 of distraction device 540 and is in locking engagement with a recess or pocket 556 (shown in FIGS. 76 and 77) located in the bottom surface 558 of the distraction device 540, thereby securing the adjacent windings and providing added support and integrity to the support structure.

Figure 79:
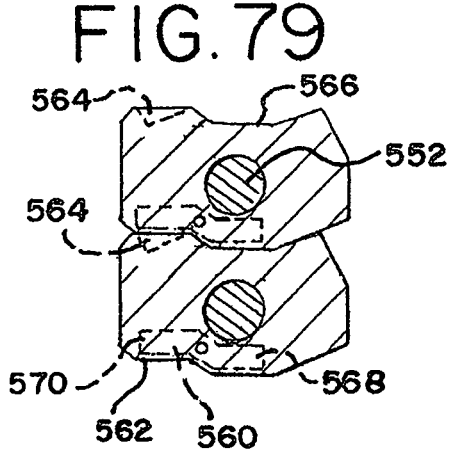
FIG. 79 is a cross-sectional view of a support structure defined by another embodiment of a distraction device.
Figure 80:
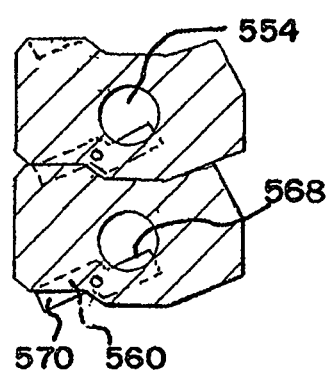
FIG. 80 is a cross-sectional view of the support structure of FIG. 79.

In the embodiments illustrated in FIGS. 79 and 80, tab 560 is located in the bottom surface 562 of the distraction device and recess or engagement pocket 564 is located in the top surface 566 of the distraction device. Similar to the embodiment above, when the guide member 552 is located within the passageway 554, the guide member contacts the activation member 568 to bias the tab 560 to the unlocked position. After the structure has been formed, the guide member 552 is removed and the locking member 570 of tab 560 extends from the bottom surface 562 and engages the recess 564 located in the top surface 566.

The embodiments illustrated in FIGS. 81 and 82 are similar to those described above except that the locking tab 572 is located in a wall 574 that defines a groove 576 in the top surface 578 and the recesses or engagement pocket 580 is located in a wall 582 defining a projection 584 of the bottom wall 586 that mates with groove when the distraction device is formed into the support structure.

The embodiments of FIGS. 83A-83C are similar to those described above except that the locking tabs 588 and recesses 592 extend in a direction that is parallel with the longitudinal axis of the distraction device 590, as shown in FIG. 83B. When guide member 552 is located with in the central passageway of distraction device 590, guide member 552 contacts activation member 593, biasing tab 588 in the unlocked position. Referring to FIG. 83C, when guide member 552 is removed from the passageway and out of contact will activation member 593, tab 588 rotates so that locking element 595 is received into and engages recess 592, thereby interlocking the adjacent windings.

FIGS. 84-87 illustrate further embodiments of the distraction device. In these embodiments, the distraction devices include interlocking projections or teeth that interlock to provide stability to the support structure.

Referring to FIG. 84, similar to the above described embodiments, distraction device 594 includes alternating projections or teeth 596 and intervening slots or recesses 598. The projections 596 include a proximal wall portion 599 and a distal wall portion 600. In this embodiment, the proximal wall portions 599 of projections 596 include a downwardly extending friction fit element 602 and the distal wall portions 600 of projections 596 include an upwardly extending friction fit element 604. Referring to FIG. 85, when distraction device 594 is curved to from a support structure, the downwardly extending friction fit elements 602 of the proximal wall portions 599 frictionally engage the upwardly extending friction fit elements 604 of the adjacent distal wall portions 600 to interlock the projections together. For example, the downwardly extending friction fit element 602 extending from proximal wall portion 599a of projection 596a frictionally engages the upwardly extending friction fit element 604 extending from distal wall portion 600b of projection 596b, thereby securing projection 596a to 596b to provide structural support to the support structure and prevents dilation of the support structure when it is exposed to axial forces.

FIGS. 86 and 87 illustrate another embodiment of a distraction device 606. In this embodiment, the distal wall portions 608 of the projections 610 include a protruding friction fit element 612, and the proximal wall portions 614 include recesses 616 for receiving and frictionally engaging the friction fit elements 612. In one embodiment, the protruding friction fit elements 612 and the recesses 616 each have a generally T-shaped configuration. In another embodiment, the distal wall portion 608 includes multiple protruding friction fit elements 611 and the proximal wall portion 614 includes multiple recesses 617. It should be understood that the protruding friction fit elements and the recess could be located on either the proximal wall portion or the distal wall portion.

Referring to FIG. 87, when distraction device 606 is curved to form a support structure, the protruding friction fit elements 612 of distal wall portions 608 are received into and frictionally engage the recesses 616 of the adjacent distal wall portions 614 to interlock the projections together. For example, the protruding friction fit element 612a extending from distal wall portion 608a of projection 610a is received into and frictionally engages recess 616b of proximal wall portion 614b of projection 610b, thereby securing projection 610a to projection 610b to provide structural support to the support structure.

FIG. 87A illustrates another embodiment of a distraction device 615. In this embodiment, the distraction device includes a reinforcing or retaining member 623 (shown in phantom) extending through the central passageway 619 of the device. The reinforcing member is configured into the shape of the support structure 621 and assists in maintaining the shape of the support structure. The reinforcing member can be a wire or a ribbon made from a metal or metal alloy, such as steel or Nitinol, or a polymer material. Additionally, the reinforcing member can be inserted into the passage 619 of the distraction device 615 after the distraction device has been formed into the support structure 621 and the guide member has been removed.

Alternatively, the reinforcing member can be a tube, such as a metal hypotube, that is inserted into and attached to the central passageway 619 of distraction device 616 prior to deployment over the guide member. In this instance, the guide member would be received into the tubular reinforcing member, which is located in passageway 616, and the tubular reinforcing member and distraction device are jointly deployed over the guide member.

FIGS. 88 and 89 illustrate a distraction device 620 that includes at least one anchor 622 extending from the back wall or spine 624 of the distraction device, such as the illustrated thread-like projection. The anchor 622 can be one continuous elongated projection extending the length of the distraction device, or the anchor 622 can be a plurality of individual projections spaced apart along the back wall 624. As illustrated in FIG. 89, when the distraction device 620 is implanted into tissue, such as cancellous bone 626 of a vertebra 628, and is wound to form the distraction device support structure 630, the anchor 622 imbeds into the cancellous bone 626 surrounding the support structure 630. When a compressive load is placed on the support structure 630 in the axial direction, the anchor 622 bears a portion of the load, which aids in the support structure maintaining its position within the tissue.

As discussed above, the distraction device can include teeth and slots that assist in adding flexibility to the distraction device. The teeth and slots of the distraction device can be configured to include features that, among other things, reduce friction as the distraction device is inserted into tissue, increase the compressive strength of the support structure in the axial direction and prevent radial dilation.

In FIGS. 91 and 92, the distraction device 632 includes teeth 634 that extend at an angle from the back wall or spine 636 of the distraction device. The teeth 634 are preferably angled at about 30 degrees to about 90 degrees relative to the spine 636, and more preferably angled at about 60 degrees relative to the spine 636. Between the angled teeth 634 are slots 638. Each slot 638 has an opening or pitch of about 5 degrees to about 35 degrees as measured between the proximal wall 640 of one tooth 634a and the distal wall 642 of an adjacent tooth 634b, and more preferably about 20 degrees, as illustrated in FIG. 92.

The angled teeth 634 are angled in a proximal direction or in a direction away from the tissue in which it is inserted. Because the teeth 634 are angled away from the tissue, the angled teeth slide smoothly past the tissue as the distraction device 632 is inserted, thereby reducing the risk of the distraction device getting caught or being hung-up on tissue during insertion. The angle teeth 634 also can function to resist retraction or withdrawal of the distraction device 632 once it is deployed into tissue. For instance, if the distraction device 632 is moved in a direction to retract the distraction device from tissue, the teeth 634 engage the tissue to resist such retraction. This resistance to retraction or reverse movement aids in preventing radial dilation of the distraction device after the distraction device has been deployed.

As illustrate in FIG. 91, as the distraction device 632 is wound to form the distraction device support structure 640, the tips 633 of the teeth 634 of the distraction device move closer together and close down or reduce the size or pitch of the slots 638 in between the teeth. The moving of the teeth 634 into a closer configuration results in the distraction device 632 being more dense (more material, less open space) towards the middle portion of the support structure 640. The denser distraction device 632 adds stability to the center of the support structure 640 and aids in increasing the support structure's ability to withstand higher compressive forces in the axial direction.

FIGS. 93 and 94 illustrate an alternative embodiment of a distraction device 642 having teeth 644 and slots 646. In this embodiment, the opening or pitch of the slots 646 are reduced to about 14 degrees (as shown in FIG. 94). As illustrated in FIG. 93, as the distraction device 642 curves to form the distraction device support structure 648, the tips 647 of the teeth 644 are optimized to almost completely close slots 646. In one embodiment, the tips of the teeth contact adjacent teeth to completely close slots 646. Such a configuration results in a distraction device 642 that is denser than the immediate previous embodiment and provides more stability to the center portion of the support structure 648.

FIGS. 95-98 illustrates another embodiment of a distraction device 650 that can include features that result in the distraction device forming a distraction device support structure 652 that has a uniform or flat end surface 654. Referring to FIG. 96, in one embodiment of the distraction device 650, the distal end portion 656 of the distraction device includes an angled or sloped first section 658 that has a length that is equal to the length required for one revolution or to form one winding. The distal tip 660 of the first angled section 658 is preferably generally smaller than about half the height of the majority of the distraction device, and the proximal end portion 662 of the first angle section 658 is preferably the same height of the majority of the distraction device. Proximal to the first angled section 658 is a second angled or sloped section 664 that has generally the same size and shape as the first angled section 658.

Turning to FIG. 97, the distraction device 650 is advanced over a coiled guide member 668, and as the first winding or loop 670 of the distraction device is formed, the distal tip 660 of the first angled section 658 nests into the second angled section 664 so that the end 654 of the support structure 652 will be uniform or flat. After the first winding 670 is formed, the distraction device 650 is further advanced along the guide member 668 to form the rest of the distraction device support structure 652 with the end surface 654 remaining in a flat or uniform configuration as illustrated in FIG. 98. The uniform or flat configuration of the end 654 of the support structure 652 provides for even distraction of the tissue layers and uniform or even contact between the distraction device support structure and the tissue layers.

Depending on the procedure, sometimes it is necessary for the guide member to traverse or bore through tissue, such as cancellous bone. For such applications, the distal end portion of the guide member can be configured to reduce the amount of penetration force required for insertion of the guide member. For example, the distal end portion of the guide member can be designed to reduce the amount of friction between the tissue and the guide member.

Referring to FIG. 99, in one embodiment, the guide member 676 includes an outer elongated member 678 that has a lumen therethrough. An inner or central elongated member 680 extends through the lumen and past the distal end portion 682 of the outer elongated member 678. Both the outer elongated member 678 and the inner elongated members 680 can be made of a shape memory material that has a natural coil or spring-like shape. Alternatively, either the outer elongated member 678 or the inner elongated member 680 can be made of a shape memory material. As such, the guide member can have a linear configuration for deployment and a non-linear configuration in-situ.

The inner member 680 is rotatable within the lumen of outer member 678, and the proximal end portion 684 of the inner member 680 is operatively connected to a rotational driving motor 686. The rotational driving motor 686 drives the inner member 680 to rotate relative to the outer member 678. The distal end portion 688 of the inner member 680 can also include a pointed tip for penetrating tissue.

To deploy the guide member 676, the distal end portion 688 of the inner member 680 is inserted into tissue, and the rotational driving motor 686 is activated to cause the inner member 680 to rotate relative to the outer member 678. The rotational movement of the inner member 680 is translated to distal end portion 688 of the inner member to create a drilling action for penetrating the tissue. Because the inner member 680 is cover by the outer member 678, the tissue adjacent the outer member 678 is substantially unaffected by the rotational movement of the inner member 680. The guide member 676 is advanced into tissue or between tissue layers until the guide member has formed the desired number of loops or has reached the desired height.

The immediately above-described guide member, as well as, any of the other guide members described herein can have a distal end portion that is configured easily penetrate tissue. For example, FIG. 100 illustrates a distal end portion 690 of a guide member 692 that includes a ball or spherically shaped distal end portion that has a cross-section that is larger than the cross-section of the remaining portion of the guide member.

FIG. 101 illustrates a distal end portion 696 of a guide member 698 that has a generally pointed or spear-like shape.

FIG. 102 illustrates a distal end portion 700 of a guide member 702 that has a generally duck-billed shape.

FIGS. 103 and 104 illustrate an embodiment of a guide member 704 that includes a cutting surface 708 located at the distal tip 710 of the guide member and an extendable/retractable cutting member 706. The extendable/retractable cutting member 706 includes a catch 712 and a cutting edge 714. Prior to advancement through tissue, the cutting member 706 is in a first or retracted position in which the cutting member is located in a recess or pocket 720 of the guide member 704. When guide member 704 is advanced through tissue, catch 712 contacts or catches on the tissue, causing cutting member 706 to rotate about hinge 716 and extend outwardly out of recess 720, as shown in phantom in FIG. 104.

As the guide member 704 is further advanced through the tissue, the cutting edge 714 of extendible member 706 cuts the tissue adjacent the path of the guide member, thereby weakening the structural integrity of the tissue surrounding the guide member. After a desired amount of the guide member 704 has been deployed, an implant, such as a distraction device, can be deployed over the guide member. Because extendible member 706 has weakened the structural integrity of the tissue surrounding guide member 704, less drive force is required to advance the implant through the tissue and along the guide member.

After deployment of the implant, the guide member 704 is withdrawn from the tissue. As the guide member 704 is withdrawn, the back wall 718 of extendible member 706 contacts the implant and/or the surrounding tissue, which forces the extendible member 706 to retract back into recess 720. With extendible member 706 retracted, the guide member is easily removed from the tissue and implant without any interference from the extendible member.

FIG. 105 illustrates a cutting device 730 that is adapted to be advanced along a guide member that has been previously deployed within tissue. Cutting device 730 includes a passageway 732 extending along an axis $X_1$ of the cutting device. Passageway 732 is adapted to receive a guide member for mounting and advancing cutting device 730 along the guide member. Cutting device 730 also includes at least one cutting edge or blade 734 that extends from cutting device 730 in a direction perpendicular to axis $X_1$.

Referring to FIG. 106, a guide member 736 is deployed into the cancellous bone 738 of a vertebral body 740. After guide member 736 has been deployed, cutting member 730 is distally advanced over guide member 736. In one embodiment, cutting member 730 can be advanced and retracted by a pusher member 743 operatively connected to a proximal end portion 742 of the cutting member 730. As cutting member 730 is advanced along guide member 736, cutting edges 734 cut the cancellous bone tissue adjacent the guide member, thereby weakening the structural integrity of the surrounding bone tissue. After cutting member 730 has been advanced along guide member 736 a desired distance, the cutting member 730 is retracted back along the guide member 736 and removed. For example, pusher member 743 can be retracted or pulled distally to retract the cutting member 730 back along the guide member. A spinal implant, such as any of the spinal implants described herein, can be deployed along guide member 736. Because cutting member 730 has weakened the structural integrity of the tissue surrounding guide member 736, less drive force is required to advance the implant through the tissue and along the guide member.

The normal intervertebral disk has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion.

Figure 113:
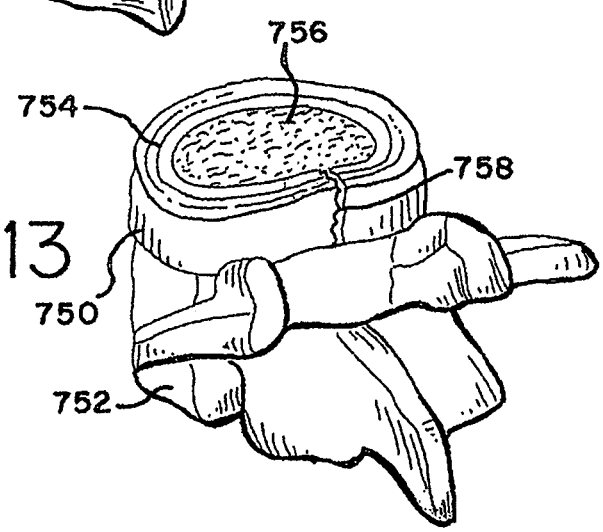
FIG. 113 is a perspective view of a damaged intervertebral disk having an annular fissure.

Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disk. FIG. 113 illustrates an intravertebral disk 750 shown above a vertebral body 752. Disk 750 includes an annulus 754 and a nucleus 756 contained therein. The annulus 754 has a rupture or fissure 758 that could lead to a nucleus herniation. As explained in greater detail below, the devices and methods disclosed herein can be used as a containment device for containing the nucleus of within the disk and to prevent herniation or bulging of the nucleus through the annulus of the disk.

Figure 114:
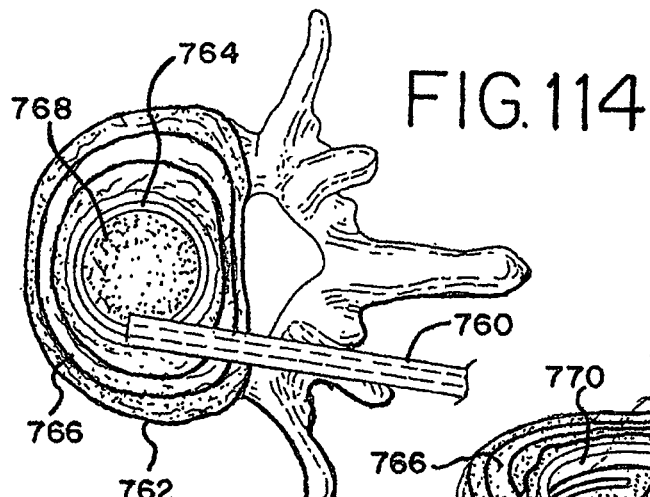
FIG. 114 is a top view of an intervertebral disk, shown with a guide member deployed therein.

Referring to FIG. 114, in one method of treating an intervertebral disk 762, a cannula 760 is placed through an access port into the disk 762 and a guide member 764 is deployed through the cannula 760 into the disk. As in the previous embodiments, the guide member 764 forms a coiled or spring-like shape within the disk. The coil-like configuration of guide member 764 substantially surrounds the disk nucleus 768. Preferably, the guide member is inserted in or along the outer perimeter of the nucleus 768 or the inner perimeter of the annulus 766. More preferably, the guide member is inserted substantially between the nucleus 768 and the annulus 766 and forms the coil-like shape therebetween.

Figure 115:
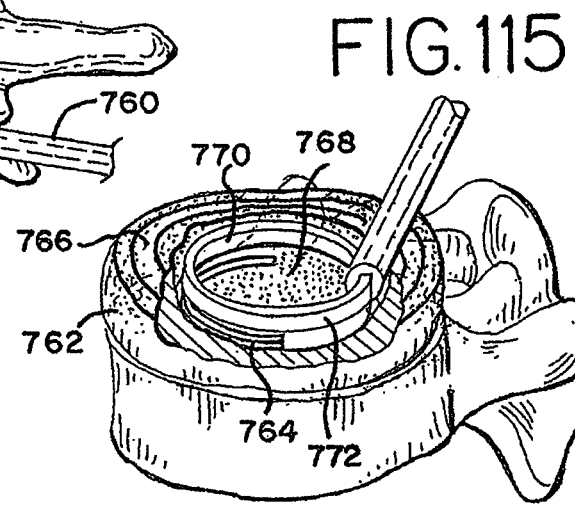
FIG. 115 is a perspective view of the intervertebral disk of FIG. 114, shown with a containment device deployed over the guide member.
Figure 116:
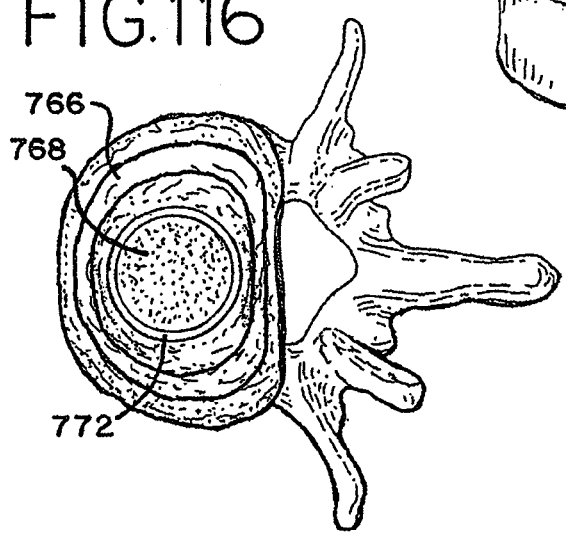
FIG. 116 is a top view of the intervertebral disk of FIG. 114, shown with the containment device deployed therein.

After the guide member 764 has been deployed, a containment device 770 is inserted along the guide member 764 and into disk 762 to form a coil or spring-shaped barrier 772 that substantially surrounds and contains at least a portion of the nucleus 768, and preferably substantially surrounds and contains the entire nucleus, as illustrated in FIG. 115. The containment device 770 is advanced over the guide member 764 until the desired height or the desired number of windings is attained. After the barrier 772 has been formed, the guide member 764 may be withdrawn from the barrier or may be cut or otherwise detach and left within the barrier to add extra support and stability to the barrier. Referring to FIG. 116, the deployed barrier 772 substantially encircles the nucleus 768 to contain the nucleus and prevent it from bulging or extruding through the annulus 766.

Figure 117:
FIGS. 117-120 illustrate different embodiment of cross-sectional profiles of the containment device.
Figure 118:
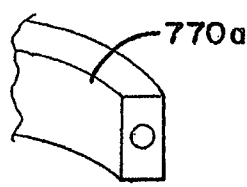
Figure 119:
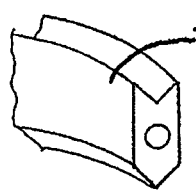
Figure 120:
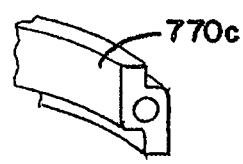

The containment device 770 can have a variety of shapes and configurations. For example, the containment device 770a could have a rectangular cross-section as illustrated in FIG. 118. In another embodiment, the containment device has frictionally engaging surfaces that engage to add in maintaining the shape of the barrier formed by the containment device. For example, the containment device 770b may have a generally V-shaped cross-section, as illustrated in FIG. 119, or the containment device 770c may have the interlocking design illustrated in FIGS. 117 and 120.

The containment device of the present invention also can be used for annulus repair. Instead of treating a herniated disk by enclosing the nucleus, the containment device can be positioned along a damaged annulus to provide supported to the nucleus and annulus.

Figure 121:
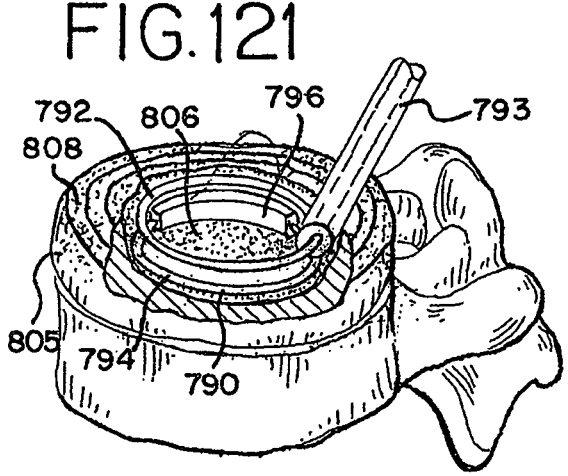
FIG. 121 is a perspective view of an intervertebral disk, shown with a guide member and containment device deployed over the guide member.
Figure 122:
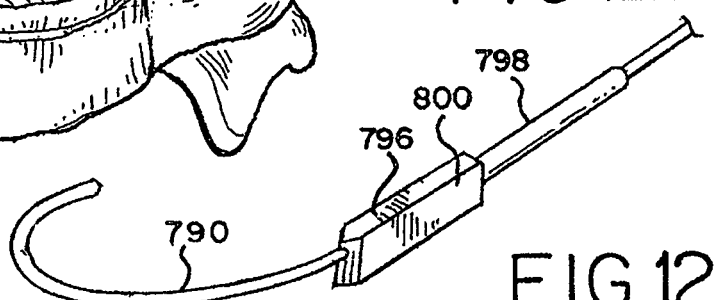
FIG. 122 is a perspective view of a guide member and containment device.

Referring to FIG. 121, a guide member 790 can be deployed through a cannula 793 into the intervertebral disk 805 to form a coil-like structure substantially around at portion of the nucleus 806. Preferably, the guide member 790 is inserted in or along the outer perimeter of the nucleus 806 or the inner perimeter of the annulus 808. More preferably, the guide member is inserted substantially between the nucleus 806 and the annulus 808 and forms the coil-like shape therebetween. The guide member 790 forms a first winding 792 and a second winding 794 within the disk 805. After the guide member 790 is deployed, a containment device 796 is advanced along the guide member 790, preferably by a pusher 798, as illustrated in FIG. 122. In this embodiment, the containment device 796 is preferably smaller than about one full winding of the coil-like guide member, and can be substantially smaller than one full winding of the guide member. The containment device 796 is advanced along the guide member into the disk 805 and is positioned at a desired location along the second winding 794. The containment device is positioned along the guide member 790 at a location adjacent disk tissue in need of treatment or support. For example, in one embodiment, the containment device 796 is positioned adjacent a fissured portion of the annulus.

Optionally, the containment device can include a radiopaque marker so that the positioning of the containment device can be monitored through fluoroscopy. Furthermore, referring to FIG. 122, the pusher member 798 can be a catheter like member that is also advanced over the guide member 790. The pusher member 798 can also include a grasping or holding groove (not shown) that engages proximal end portion 800 of the containment member 796 and can control the orientation of the containment member by rotation of the pusher member. The pusher member 798 could also include a releasable locking mechanism that secures the pusher member to the containment device 796 until the containment device is in the desired location.

Figure 123:
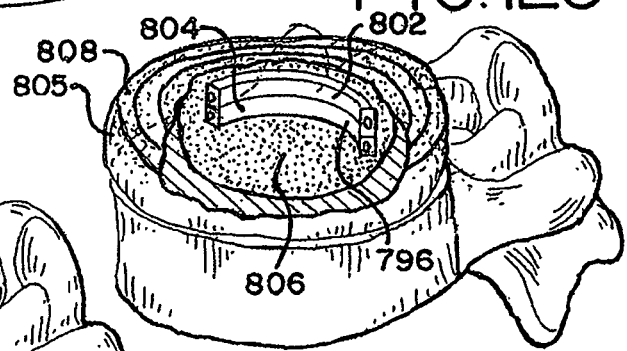
FIG. 123 is a perspective view of the intervertebral disk of FIG. 121, shown with a containment device deployed therein.
Figure 124:
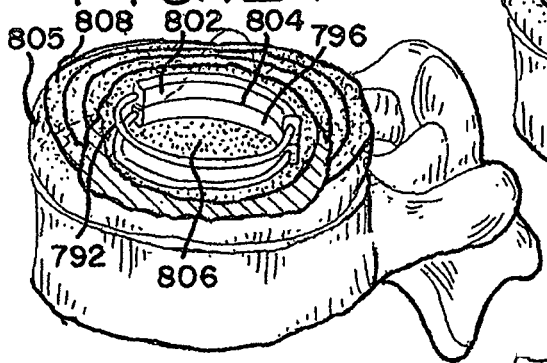
FIG. 124 is a perspective view of the intervertebral disk of FIG. 121, shown with a containment device deployed over a guide member.
Figure 125:
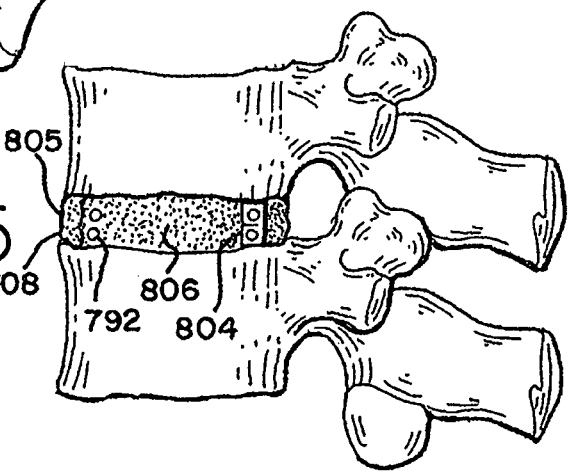
FIG. 125 is a perspective view of the intervertebral disk of FIG. 121, shown with a containment device deployed therein.

After the containment device 796 is in the desired location along the second winding 794, optionally, a second containment device 802 is advanced along the guide member 790 and positioned at a location on the first winding 792 which is above or beneath the first containment device 796, depending of the orientation of the guide member, as illustrated in FIG. 124. When a second containment device is employed, the first and second containment devices 796, 802 engage each other to form a barrier 804 that supports the nucleus 806 and annulus 808 and prevents the nucleus 806 from bulging through the damaged annulus 808. The guide member 790 may be cut or otherwise detached and left in the disk as illustrated in FIGS. 124 and 125. Alternatively, the guide member 790 may be removed from the barrier 804 as illustrated in FIG. 123.

In another embodiment of the present subject matter, a containment wire can be employed to repair a ruptured annulus. Referring to FIG. 126, a cannula 810 is introduced into the annulus 811 from a posterolateral approach (or any other applicable approaches) on the inferior side of the annulus. Containment wire 812 is then deployed through the cannula 810 and thread into and through the annulus 811, as illustrated in FIG. 127. The containment wire is made of a shape memory material that has a natural coiled configuration when deployed through the cannula, the containment wire takes on a generally linear or constrained configuration. As shown, the containment wire device 812 is advanced into the annulus and through the annulus. As the containment wire 812 is advanced out of the cannula and through the annulus, it returns to its coiled configuration and creates several loops in annulus. The number of loops depending on the height of the disk. The containment device 812 provides a fence like structure that reinforces rupture line 814 to prevent any further bulging or herniation of the nucleus 816.

In another method of treating disk with the containment wire, the containment wire is deployed to form a coil shaped structure around at least a portion of the nucleus, and preferably substantially around the entire nucleus. Similar to the deployment of the guide member of FIG. 114, the containment wire can be deployed in or along the outer perimeter of the nucleus or the inner perimeter of the annulus. Preferably, the containment wire is deployed between the nucleus and the annulus. The containment device forms several loops that substantially surround the nucleus to create coil shaped fence-like structure that substantially contains the nucleus within the annulus.

FIG. 132 illustrates another embodiment of the containment wire in which the containment wire comprises wavy wire 818. FIGS. 128-131 illustrate one embodiment of a method of introducing a wavy containment wire into an annulus of a disk. FIG. 128 illustrates one embodiment of a deployment system 820 for deployment of the wavy containment wire 818. Deployment system 820 includes a deployment cannula 822, a guide member 824 and a guide catheter 826. Referring to FIG. 129, the guide member 824 is similar to the guide member described above and has a linear deployment configuration and coil shaped deployed configuration. The guide member 824 is deployed through the cannula 822 to from a coiled shaped portion 828 within a treatment site. After a desired amount of the guide member 824 has been deployed, the guide catheter 824 is advanced over the guide member 824, as illustrated in FIGS. 129 and 130. The guide member 824 then is removed from the guide catheter 826, leaving the guide catheter in the treatment site.

The wavy containment wire 818 also is comprised of a shape memory material and includes a straight deployment configuration and the coiled wavy configuration illustrated in FIG. 132. The wavy containment wire 818 is deployed through the deployment catheter 826 in the generally straight deployment configuration. The wavy containment wire 818 is held or constrained in the straight configuration by the guide catheter 826. Once the desired amount of the wavy containment wire 818 has been advanced into the guide catheter 826, the guide catheter is withdrawn distally, as shown in FIG. 131, to allow the containment wire 818 to return to its wavy configuration in-situ.

Although the present invention is described in light of the illustrated embodiments, it is understood that this for the purposes illustration and not limitation. Other applications, modifications or use of the support or distraction device may be made without departing from the scope of this invention, as set forth in the claims now or hereafter filed.

What is claimed is:

1. A spinal implant, comprising:
a generally elongated member having a longitudinal axis and a plurality of alternating projections and slots spaced along at least a portion of the longitudinal axis wherein each projection includes a proximal wall and a distal wall and slots are defined between the proximal wall of one projection and the distal wall of an adjacent projection and extends through upper and lower surfaces of the elongated member, the slots facilitating curving of the elongated member relative to the longitudinal axis;
the elongated member having a first generally linear configuration for insertion between spinal tissue layers and a second configuration in-situ wherein the generally elongated member curves relative to the longitudinal axis to form a generally helical distraction structure for distracting spinal tissue, the helical distraction structure having a plurality of windings extending about a generally central axis, and when in the second configuration, proximal walls of a plurality of projections are spaced apart from distal walls of respective adjacent projections; and
the helical distraction structure having an extent along the central axis, which extent increases as the elongated member is linearly inserted between spinal tissue layers and curves to define the second configuration.

2. The spinal implant of claim 1 in which the generally elongated member is configured to be guided by a guide member into the second configuration in-situ.

3. The spinal implant of claim 1 wherein the generally elongated member includes a passageway therethrough for receiving flowable material.

4. The spinal implant of claim 3 wherein the passageway is in fluid communication with the slots such that flowable material may flow through the passageway and out of the slots.

5. The spinal implant of claim 1 in which the generally elongated member includes interfering surfaces that are configured such that when the generally elongated member is in the second configuration engagement between the surfaces assists in retaining the generally elongated member in the second configuration.

6. The spinal implant of claim 5 in which at least one of the interfering surfaces or elements is selectively moveable between a non-interfering position and an interfering position.

7. The spinal implant of claim 5 in which interfering surfaces are configured to resist lateral shifting between adjacent windings.

8. The spinal implant of claim 5 in which interfering surfaces are configured to resist longitudinal shifting between adjacent windings.

9. The spinal implant of claim 5 in which interfering surfaces are configured to resist lateral and longitudinal shifting between adjacent windings.

10. The spinal implant of claim 1 in which the generally elongated member includes opposed first and second surfaces, wherein the first surface includes a first interfering surface and the second surface has a second interfering surface for cooperatively engaging the the first interfering surface when the generally elongated member is in the second configuration to assist in preventing relative shifting between adjacent windings.

11. The spinal implant of claim 10 in which the first and second interfering surfaces comprise elongated shoulders, concave and convex surfaces, corrugated surfaces, raised ribs or ridges and receiving slots, or knurled surfaces.

12. The spinal implant of claim 1 in which the generally elongated member includes an anchor member configured to extend from the implant in the second configuration to anchor the generally elongated member in spinal tissue.

13. The spinal implant of claim 1 in which the generally elongated member includes an elongated passageway extending longitudinally therethrough for receiving a guide member.

14. A spinal implant system, comprising:
a generally elongated member having a longitudinal axis and a plurality of alternating projections and slots spaced along at least a portion of the longitudinal axis, and wherein the projections and slots are located along a side of the elongated member and the slots extend through upper and lower surfaces of the elongated member;
the elongated member having a first generally linear configuration for insertion between spinal tissue layers and a second configuration in-situ in which the generally elongated member curves relative to the longitudinal axis to form a generally helical distraction structure for distracting spinal tissue wherein the projections of the elongated member project generally radially toward a center axis of the helical structure, and projections of the elongated member being closer to adjacent projections than in the linear configuration but spaced apart from adjacent proximal and distal projections in the second configuration.

15. The spinal implant of claim 14 in which the generally elongated member is configured to be guided by a guide member into the second configuration situ.

16. The spinal implant of claim 14 wherein the generally elongated member includes a passageway therethrough for receiving flowable material.

17. The spinal implant of claim 16 wherein the passageway is in fluid communication with a plurality of the slots such that flowable material may flow through the passageway and the plurality of slots.

18. The spinal implant of claim 14 in which the generally elongated member includes interfering surfaces that are configured such that when the generally elongated member is in the second configuration, engagement between the surfaces assists in retaining the generally elongated member in the second configuration.

19. The spinal implant of claim 18 in which at least one of the interfering surfaces is selectively moveable between a non-interfering position and an interfering position.

20. The spinal implant of claim 18 in which interfering surfaces are configured to resist lateral shifting between adjacent windings.

21. The spinal implant of claim 18 in which interfering surfaces are configured to resist longitudinal shifting between adjacent windings.

22. The spinal implant of claim 18 in which interfering surfaces are configured to resist lateral and longitudinal shifting between adjacent windings.

23. The spinal implant of claim 14 in which the generally elongated member includes opposed first and second surfaces, wherein the first surface includes a first interfering surface and the second surface has a second interfering surface cooperatively engageable with the first interfering surface when the generally elongated member is in the second configuration to assist in preventing relative shifting between adjacent windings.

24. The spinal implant of claim 14 in which the generally elongated member includes an anchor member configured to extend from the implant in the second configuration to anchor the generally elongated member in spinal tissue.

25. The spinal implant of claim 14 in which the generally elongated member includes an elongated passageway extending longitudinally therethrough for receiving a guide member.

26. A spinal implant deployment system, comprising:
a cannula including a proximal end portion, a distal end portion and a passageway therethrough, said distal end portion of the first cannula including an opening in communication with the passageway, and the distal end portion being insertable between spinal tissue layers;
a guide member having a distal end portion, the distal end portion of the guide member being advanceable through the passageway and the opening of the cannula for deployment between spinal tissue layers, and at least the distal end portion of the guide member being formable in-situ into a generally helical configuration;
a generally elongated member adapted for advancement along the guide member and through the passageway and the opening of the cannula for deployment between tissue layers, the generally elongated member having a longitudinal axis and a plurality of alternating projections and slots along at least a portion of the longitudinal axis wherein each of the projections has a proximal wall and a distal wall and each slot is defined at least in part by the proximal wall of one projection and the distal wall of an adjacent projection;
the elongated member having a first configuration for insertion between spinal tissue layers and having a second configuration in-situ wherein the generally elongated member curves relative to the longitudinal axis to form a generally helical structure, and wherein proximal walls of projections are spaced apart from distal walls of respective adjacent projections; and
the elongated member being configured to be guided by the guide member into the second configuration to form the helical structure in-situ to separate support or both separate and support spinal tissue layers.

27. The spinal implant deployment system of claim 26 wherein the generally elongated member includes a passageway therethrough for receiving flowable material.

28. The spinal implant deployment system of claim 27 wherein the passageway is in fluid communication with a plurality of the slots such that flowable material may flow through the passageway and the plurality of slots.

29. The spinal implant deployment system of claim 26 in which the generally elongated member includes interfering surfaces that are configured such that when the generally elongated member is in the second configuration engagement between the surfaces assists in retaining the generally elongated member in the second configuration.

30. The spinal implant deployment system of claim 29 in which at least one of the interfering surfaces is selectively moveable between a non-interfering position and an interfering position.

31. The spinal implant deployment system of claim 29 in which interfering surfaces are configured to resist lateral shifting between adjacent windings.

32. The spinal implant deployment system of claim 29 in which interfering surfaces are configured to resist longitudinal shifting between adjacent windings.

33. The spinal implant deployment system of claim 29 in which interfering surfaces are configured to resist lateral and longitudinal shifting between adjacent windings.

34. The spinal implant deployment system of claim 26 in which the generally elongated member includes opposed first and second surfaces, wherein the first surface includes a first interfering surface and the second surface has a second interfering surface for cooperatively engageable with the first interfering surface when the generally elongated member is in the second configuration to assist in preventing relative shifting between adjacent windings.

35. The spinal implant deployment system of claim 26 in which the generally elongated member includes an anchor member configured to extend from the implant in the second configuration to anchor the generally elongated member in spinal tissue.

36. The spinal implant deployment system of claim 26 in which the generally elongated member includes an elongated passageway extending longitudinally therethrough for receiving the guide member.

37. A method of treating the human spine, comprising:
inserting a generally elongated member in a substantially linear configuration between tissue layers of the spine, the elongated member having a longitudinal axis and a plurality of alternating projections and slots along at least a portion of the longitudinal axis wherein each projection includes a proximal wall and a distal wall and wherein proximal walls of the projections are spaced from distal walls of respective adjacent projections to define slots therebetween and wherein slots extend through upper and lowers surfaces of the elongated member;
curving the elongated member relative to the longitudinal axis in-situ to form the elongated member into a generally helical structure circumferentially surrounding spinal tissue and wherein proximal walls of a plurality of projections remain spaced apart from distal walls of respective adjacent projections when the elongated member forms the helical structure; and
separating, supporting or both separating and supporting the tissue layers with the helical structure.

38. The method of claim 37 further including inserting flowable material between the tissue layers.

39. The method of claim 37 in which the inserting and curving of the generally elongated member includes advancing the elongated member along a guide member.

40. The method of claim 39 wherein the generally elongated member includes a passageway therethrough for receiving the guide member and the method further includes inserting the guide member through the passageway.

41. The method of claim 37 in which the generally helical structure circumferentially surrounds a volume.

42. The method of the claim 41 further including injecting flowable material into the volume.

43. The method of claim 42 wherein the flowable material includes bone filler.

44. The method of claim 42 wherein the flowable material includes bone cement.

45. The method of claim 41 wherein the generally elongated member includes a passageway therethrough for receiving flowable material and the method further includes delivering flowable material through the passageway and into the volume.

46. The method of claim 37 in which inserting the generally elongated member between tissue layers comprises inserting the generally elongated member into a vertebral body, the helical structure including a generally central axis extending substantially between endplates of the vertebral body and the generally helical structure circumferentially surrounding cancellous bone.

47. The spinal implant of claim 37 in which the generally elongated member includes interfering surfaces that are configured such that when the generally elongated member forms the helical structure, engagement between the surfaces or elements assists in retaining the generally elongated member in the form of the helical structure.

48. The method of claim 37 wherein the generally elongated member includes a passageway therethrough for receiving flowable material, and the passageway is in fluid communication with a plurality of the slots so flowable material can flow through the passageway and the slots.

49. A method of treating the human spine, comprising:
inserting a generally elongated member in a substantially linear configuration between tissue layers of the spine, the elongated member having a longitudinal axis and a plurality of alternating projections and slots spaced along at least a portion of the longitudinal axis wherein each projection includes a proximal wall and a distal wall and the slots are defined between the proximal wall of one projection and the distal wall of an adjacent projection and wherein the slots extend through upper and lower surfaces of the elongated member;
curving the elongated member relative to the longitudinal axis in-situ to form the elongated member into a generally helical structure having a plurality of windings extending about a generally central axis and wherein the proximal walls of a plurality of projections are spaced apart from the distal walls of the respective adjacent projections; and
increasing an extent of the helical structure along the central axis as the elongated member is linearly inserted between spinal tissue and curves to define the generally helical structure.

50. The method of claim 49 further including inserting flowable material between the tissue layers.

51. The method of claim 49 in which the inserting and curving of the generally elongated member include advancing the elongated member along a guide member.

52. The method of claim 51 wherein the generally elongated member includes a passageway therethrough for receiving the guide member and the method further includes inserting the guide member through the passageway.

53. The method of claim 49 in which the generally helical structure circumferentially surrounds a volume.

54. The method of claim 53 further including injecting flowable material into the volume.

55. The method of claim 54 in which the flowable material includes bone filler.

56. The method of claim 54 in which the flowable material includes bone cement.

57. The method of claim 49 in which inserting the generally elongated member between tissue layers comprises inserting the generally elongated member into a vertebral body such that the generally central axis of the generally helical structure extends substantially between endplates of the vertebral body and the generally helical structure circumferentially surrounds cancellous bone.

58. The method of claim 49 in which the generally elongated member includes interfering surfaces that are configured such that when the generally elongated member forms the helical structure, engagement between the surfaces assists in retaining the generally elongated member in the form of the helical structure.

59. The spinal implant of claim 49 in which the generally elongated member includes opposed first and second surfaces, wherein the first surface includes a first interfering surface and the second surface includes a second interfering surface, the first interfering surface on one winding cooperatively engageable with the second interfering surface on an adjacent winding when the generally elongated member is formed into the helical structure to assist in preventing relative shifting between adjacent windings.

60. The method of claim 49 wherein the generally elongated member includes a passageway therethrough for receiving flowable material and the method further includes delivering flowable material into the passageway.

61. The method of claim 60 wherein the passageway is in fluid communication with a plurality of the slots so the flowable material can flow through the passageway and the plurality of slots.

62. A method of treating the human spine, comprising:
inserting a generally elongated member in a substantially linear configuration between tissue layers of the spine, the elongated member having a longitudinal axis and a plurality of alternating projections and slots spaced along at least a portion of the longitudinal axis wherein each projection includes a proximal wall and a distal wall and wherein the proximal and distal walls of adjacent projections define a slot therebetween and wherein the slots extend through upper and lowers surfaces of the elongated member;
curving the elongated member relative to the longitudinal axis in-situ to form the elongated member into a generally helical structure having a generally central axis, the projections of the elongated member projecting generally radially inwardly toward the central axis and the proximal wall of at least one projection being spaced apart from the distal wall of a respective adjacent projection when the elongated member defines the generally helical structure; and
separating, supporting or both separating and supporting the tissue layers with the helical structure.

63. The method of claim 62 further including inserting flowable material between the tissue layers.

64. The method of claim 62 in which the inserting and curving of the generally elongated member include advancing the elongated member along a guide member.

65. The method of claim 64 wherein the generally elongated member includes a passageway therethrough for receiving the guide member and the method further includes inserting the guide member through the passageway.

66. The method of claim 62 in which the generally helical structure circumferentially surrounds a volume.

67. The method of claim 66 further including injecting flowable material into the volume.

68. The method of claim 67 in which the flowable material includes bone filler.

69. The method of claim 67 in which the flowable material includes bone cement.

70. The method of claim 62 in which inserting the generally elongated member between tissue layers comprises inserting the generally elongated member into a vertebral body such that the generally central axis of the generally helical structure extends substantially between endplates of the vertebral body and the generally helical structure circumferentially surrounds cancellous bone.

71. The method of claim 62 in which the generally elongated member includes interfering surfaces that are configured such that when the generally elongated member is formed into the generally helical structure, engagement between the surfaces assists in retaining the generally elongated member in the form of the generally helical structure.

72. The spinal implant of claim 62 in which the generally helical structure includes a plurality of windings and the generally elongated member includes opposed first and second surfaces, wherein the first surface includes a first interfering surface and the second surface includes a second interfering surface, the first interfering surface on one winding cooperatively engageable with the second interfering surface on an adjacent winding when the generally elongated member is formed into the generally helical structure to assist in preventing relative shifting between adjacent windings.

73. The method of claim 62 wherein the generally elongated member includes a passageway therethrough for receiving flowable material and the method further includes delivering flowable material into the passageway.

74. The method of claim 73 wherein the passageway is in fluid communication with a plurality of the slots so the flowable material can flow through the passageway and the plurality of slots.

75. A spinal implant comprising:
a generally elongated member having a longitudinal axis and a plurality of projections spaced along at least a portion of the longitudinal axis, each projection including a proximal wall and a distal wall and wherein proximal and distal walls of adjacent projections define a slot therebetween wherein slots extend through upper and lower surfaces of the elongated member;
the elongated member having a first linear configuration for insertion between spinal tissue layers and a second configuration in-situ in which the generally elongated member curves relative to the longitudinal axis to form a generally helical distraction structure including a plurality of windings extending about a generally central axis;
when in the second configuration a plurality of the projections of the elongated member projecting generally radially inwardly toward the central axis and proximal walls of projections being spaced apart from distal walls of respective adjacent projections; and
the helical distraction structure having an extent along the central axis, which extent increases as the elongated member is linearly inserted between spinal tissue layers and curves to define the second configuration.

76. The spinal implant of claim 75 in which the generally elongated member is configured to be guided by a guide member into the second configuration in-situ.

77. The spinal implant of claim 75 wherein the generally elongated member includes a passageway therethrough for receiving flowable material.

78. The spinal implant of claim 77 wherein the passageway is in fluid communication with a plurality of the slots such that flowable material may flow through the passageway and the plurality of slots.

79. The spinal implant of claim 75 in which the generally elongated member includes interfering surfaces that are configured such that when the generally elongated member is in the second configuration, engagement between the surfaces assists in retaining the generally elongated member in the second configuration.

80. The spinal implant of claim 79 in which at least one of the interfering surfaces is selectively moveable between a non-interfering position and an interfering position.

81. The spinal implant of claim 79 in which interfering surfaces are configured to resist lateral shifting between adjacent windings.

82. The spinal implant of claim 79 in which interfering surfaces are configured to resist longitudinal shifting between adjacent windings.

83. The spinal implant of claim 79 in which interfering surfaces are configured to resist lateral and longitudinal shifting between adjacent windings.

84. The spinal implant of claim 75 in which the generally elongated member includes opposed first and second surfaces, wherein the first surface includes a first interfering surface and the second surface has a second interfering surface cooperatively engageable with the first interfering surface when the generally elongated member is in the second configuration to assist in preventing relative shifting between adjacent windings.

85. The spinal implant of claim 75 in which the generally elongated member includes an anchor member configured to extend from the implant in the second configuration to anchor the generally elongated member in spinal tissue.

86. The spinal implant of claim 75 in which the generally elongated member includes an elongated passageway extending longitudinally therethrough for receiving a guide member.

* * * * *

UNITED STATES PATENT AND TRADEMARK OFFICE
CERTIFICATE OF CORRECTION

PATENT NO. : 8,591,583 B2
APPLICATION NO. : 12/034853
DATED : November 26, 2013
INVENTOR(S) : Laurent Schaller et al.

It is certified that error appears in the above-identified patent and that said Letters Patent is hereby corrected as shown below:

In the Claims

In Claim 47, col. 40, ln. 11, after "The" delete "spinal implant" and insert -- "method" --.

In Claim 59, col. 41, ln. 7, after "The" delete "spinal implant" and insert -- "method" --.

In Claim 72, col. 42, ln. 9, after "The" delete "spinal implant" and insert -- "method" --.

Signed and Sealed this
Eighth Day of July, 2014

Michelle K. Lee
*Deputy Director of the United States Patent and Trademark Office*